US008530475B2

(12) United States Patent
Creighton et al.

(10) Patent No.: US 8,530,475 B2
(45) Date of Patent: Sep. 10, 2013

(54) BRIDGED ARYL PIPERAZINES DERIVATIVES USEFUL FOR THE TREATMENT OF CNS, GI-URINARY AND REPRODUCTIVE DISORDERS

(75) Inventors: Christopher J. Creighton, San Diego, CA (US); Tina Morgan Ross, Royersford, PA (US); Allen B. Reitz, Lansdale, PA (US); Cheryl P. Kordik, Johnsburg, IL (US); Steven Paget, Hillsborough, NJ (US); Gregor J. MacDonald, Beerse (BE)

(73) Assignee: Janssen Pharmaceutica NV

( * ) Notice: Subject to any disclaimer, the term of this patent is extended or adjusted under 35 U.S.C. 154(b) by 1610 days.

(21) Appl. No.: 11/750,629

(22) Filed: May 18, 2007

(65) Prior Publication Data
US 2008/0070919 A1 Mar. 20, 2008

Related U.S. Application Data

(60) Provisional application No. 60/801,439, filed on May 18, 2006.

(51) Int. Cl.
*A61K 31/497* (2006.01)
*C07D 295/00* (2006.01)
(52) U.S. Cl.
USPC ........................ 514/252.1; 544/358

(58) Field of Classification Search
USPC .................................. 544/358; 514/252.12
See application file for complete search history.

(56) References Cited

FOREIGN PATENT DOCUMENTS
WO WO 03/086315 10/2003

OTHER PUBLICATIONS

International Search Report, PCTUS2007/069256, dated Jul. 11, 2008.
Paradisi, et al., "Stereoselective Synthesis of Alpha, Alph—Diamino-Dicarboxylic acids Part 2" Tetrahedron: Asymmetry, 2000, pp. 4617-4622, vol. 11 No. 22 & pp. 4618, compounds 2 and 3.
Du, et al., "Noncovalent Self-assembly of Bicyclo[4.2.2. 2]diketopiperazines: Influence of Saturation I the Bridging Carbacyclic Ring", Organic Letters, 2004, pp. 309-312, vol. 6.
Creighton, et al., "Synthesis of an Eight-Membered Cyclic Pseudo-Dipeptide Using Ring Closing Metathesis" Organic Letters, pp. 893-895, 2001, vol. 3(6).
Perez, et al., "Randomised, Double-Blind, Placebo-Controlled Trial of Pindolol in Combination with Fluoxetine Antidepressant Treatment", The Lancet, pp. 1594-1597, 1997 vol. 349.

*Primary Examiner* — Paul V. Ward
(74) *Attorney, Agent, or Firm* — Yuriy P. Stercho

(57) ABSTRACT

The present invention is directed to bridged aryl piperazine derivatives, pharmaceutical compositions containing them and their use in the treatment of depression and related disorders. The compounds of the present invention are serotonin transport inhibitors and/or modulators of $5HT_{1A}$.

18 Claims, No Drawings

BRIDGED ARYL PIPERAZINES DERIVATIVES USEFUL FOR THE TREATMENT OF CNS, GI-URINARY AND REPRODUCTIVE DISORDERS

CROSS REFERENCE TO RELATED APPLICATIONS

This application claims the benefit of U.S. Provisional Application 60/801,439, filed on May 18, 2006, which is incorporated by reference herein in its entirety.

FIELD OF THE INVENTION

The present invention is directed to bridged aryl piperazine derivatives, pharmaceutical compositions containing them and their use in the treatment of, CNS disorders such as depression, Alzheimer's disease, mild cognitive impairment, anxiety, bipolar disorder, etc.; gastrointestinal disorders such as constipation-predominant IBS, chronic constipation, colonic inertia, idiopathic colonic pseudo-obstruction, etc.; and reproductive disorders such as hot flashes, premature ejaculation, etc.

BACKGROUND OF THE INVENTION

Major depression is a serious health problem affecting more than 5% of the population, with a lifetime prevalence of 15-20%.

Selective serotonin reuptake inhibitors have produced success in depression and related illnesses and have become among the most prescribed drugs. However, they have a slow onset of action, often taking several weeks to produce their full therapeutic effect. Furthermore, they are effective in less than ⅔ of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptor.

However, although a single dose of an SSRI can inhibit the neuronal serotonin transporter which would be expected to increase synaptic serotonin, long term treatment is required before clinical improvement is achieved.

It has been suggested that the SSRIs increase the serotonin levels in the vicinity of the serotonergic cell bodies and that the excess serotonin activates somatodendritic autoreceptors, $5HT_{1A}$ receptors, causing a decrease in serotonin release in major forebrain areas. This negative feedback limits the increment of synaptic serotonin that can be induced by antidepressants such as SSRIs.

A $5HT_{1A}$ antagonist would limit the negative feedback and should improve the efficacy of the serotonin reuptake mechanism (Perez, V., et. al., *The Lancet*, 349:1594-1597 (1997)). Such a combination therapy would be expected to speed up the effect of the serotonin reuptake inhibitor.

Thus, there remains a need for compounds which inhibit serotonin reuptake and which are antagonists of the $5HT_{1A}$ receptor, useful for the treatment of, for example, depression, preferably wherein the compounds produce a rapid onset of action.

SUMMARY OF THE INVENTION

The present invention is directed to compounds of formula (I) and compounds of formula (II)

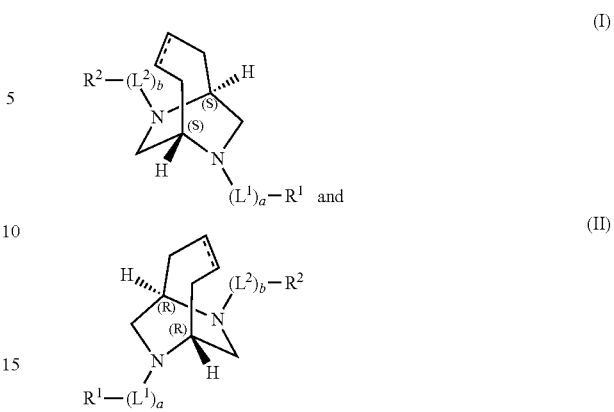

wherein
⎓ is a single or double bond;
a is an integer from 0 to 1;
$L^1$ is selected from the group consisting of —$C_{1-4}$alkyl-, —$CH_2$—$C_{2-4}$alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)O—, —($C_{2-4}$alkyl)-$NR^A$, —($C_{1-4}$alkyl)-$SO_2$—, —C(O)—($C_{1-4}$alkyl)-, —O—($C_{1-4}$alkyl), —C(O)O—($C_{1-4}$ alkyl)-, —$NR^A$—($C_{1-4}$alkyl)-, —($C_{1-4}$alkyl)-O—($C_{1-4}$alkyl)-, —($C_{1-4}$alkyl)-C(O)—($C_{1-4}$alkyl)-, —($C_{1-4}$alkyl)-OC(O)—($C_{1-4}$alkyl)-, —($C_{1-4}$alkyl)-C(O)O—($C_{1-4}$alkyl)-, —($C_{2-4}$alkyl)-$NR^A$—($C_{1-4}$alkyl)-, —($C_{1-4}$alkyl)-$SO_2$—($C_{1-4}$alkyl)-, —C(O)—$NR^A$—, —C(O)—$NR^A$—($C_{1-4}$alkyl)-, —$NR^A$—C(O)— and —$NR^A$—C(O)—($C_{1-4}$alkyl)-;
wherein the —$C_{1-4}$alkyl- or $C_{2-4}$alkyl, whether alone or as part of a substituent group is optionally substituted with one or more substituents independently selected from the group consisting of hydroxy, $C_{1-4}$alkoxy, amino, ($C_{1-4}$alkyl)amino, di($C_{1-4}$alkyl)amino, phenyl, SH and S($C_{1-4}$alkyl);
wherein $R^A$ is selected from the group consisting of hydrogen, —$C_{1-4}$alkyl phenyl, —C(O)—($C_{1-4}$alkyl), —C(O)-carbocyclyl, —C(O)-heterocyclyl, —$SO_2$—($C_{1-4}$alkyl)-$SO_2$-carbocyclyl and —$SO_2$-heterocyclyl;
provided that the chain length of $L^1$, not counting branching, is one to six atoms;
$R^1$ is selected from the group consisting of hydrogen, $C_{1-4}$alkyl, cycloalkyl, partially unsaturated carbocyclyl, aryl, biphenyl, heteroaryl and heterocycloalkyl;
wherein the cycloalkyl, partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, $C_{1-4}$alkyl, $C_{1-4}$alkoxy, halogenated $C_{1-4}$alkyl, halogenated $C_{1-4}$alkoxy, hydroxy substituted $C_{1-4}$alkyl, cyano, nitro, amino, $C_{1-4}$alkylamino, di($C_{1-4}$alkyl)amino, [1,3]dioxolanyl, alkoxy-C(O)—, $NR^BR^C$—C(O)— and —$SO_2$—$NR^BR^C$;
wherein $R^B$ and $R^C$ are each independently selected from the group consisting of hydrogen and $C_{1-4}$alkyl;
b is an integer from 0 to 1;
$L^2$ is selected from the group consisting of —$C_{1-4}$alkyl-, —$CH_2$—$C_{2-4}$alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)O—, —($C_{2-4}$alkyl)-$NR^D$, —($C_{1-4}$alkyl)-$SO_2$—, —C(O)—($C_{1-4}$alkyl)-, —O—($C_{1-4}$alkyl), —C(O)O—($C_{1-4}$ alkyl)-, —$NR^D$—($C_{1-4}$alkyl)-, —($C_{1-4}$alkyl)-O—($C_{1-4}$alkyl)-, —($C_{1-4}$alkyl)-C(O)—($C_{1-4}$alkyl)-, —($C_{1-4}$alkyl)-OC(O)—($C_{1-4}$alkyl)-, —($C_{1-4}$alkyl)-

C(O)O—(C$_{1-4}$alkyl)-, —(C$_{2-4}$alkyl)-NR$^D$—(C$_{1-4}$alkyl)-, —(C$_{1-4}$alkyl)-SO$_2$—(C$_{1-4}$alkyl)-, —C(O)—NR$^D$—, —C(O)—NR$^D$—(C$_{1-4}$alkyl)-, —NR$^D$—C(O)— and —NR$^D$—C(O)—(C$_{1-4}$alkyl)-;

wherein the —C$_{1-4}$alkyl- or C$_{2-4}$alkyl, whether alone or as part of a substituent group is optionally substituted with one or more substituents independently selected from the group consisting of hydroxy, C$_{1-4}$alkoxy, amino, (C$_{1-4}$alkyl)amino, di(C$_{1-4}$alkyl)amino, phenyl, SH and S(C$_{1-4}$alkyl);

wherein R$^D$ is selected from the group consisting of hydrogen, —C$_{1-4}$alkyl phenyl, —C(O)—(C$_{1-4}$alkyl), —C(O)-carbocyclyl, —C(O)-heterocyclyl, —SO$_2$—(C$_{1-4}$alkyl)-SO$_2$-carbocyclyl and —SO$_2$-heterocyclyl;

provided that the chain length of L$^2$, not counting branching, is one to six atoms;

R$^2$ is selected from the group consisting of hydrogen, C$_{1-4}$alkyl, cycloalkyl, partially unsaturated carbocyclyl, aryl, biphenyl, heteroaryl and heterocycloalkyl;

wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, C$_{1-4}$alkyl, C$_{1-4}$alkoxy, halogenated C$_{1-4}$alkyl, halogenated C$_{1-4}$alkoxy, hydroxy substituted C$_{1-4}$alkyl, cyano, nitro, amino, C$_{1-4}$alkylamino, di(C$_{1-4}$alkyl)amino, [1,3]dioxolanyl, —C$_{1-4}$alkoxy-C(O)—, NR$^E$R$^F$—C(O)— and —SO$_2$—NR$^E$R$^F$;

wherein R$^E$ and R$^F$ are each independently selected from the group consisting of hydrogen and C$_{1-4}$alkyl;

provided that the chain length of L$^1$, not counting branching, plus the chain length of L$^2$, not counting branching, is not greater than about 12 atom;

provided further that when a is 0 and b is 0 then R$^1$ and R$^2$ are not each hydrogen;

and pharmaceutically acceptable salts thereof.

The present invention is further directed to compounds of formula (CI) and (CII)

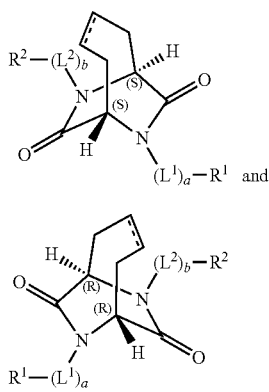

wherein
─ is a single or double bond;
a is an integer from 0 to 1;
L$^1$ is selected from the group consisting of —C$_{1-4}$alkyl-, —CH$_2$—C$_{2-4}$alkenyl-, —CH$_2$—C$_{2-4}$alkynyl-, —SO$_2$—, —C(O)—, —C(O)O—, —(C$_{1-4}$alkyl)-C(O)—, —(C$_{1-4}$alkyl)-O—, —(C$_{1-4}$alkyl)-C(O)O—, —(C$_{2-4}$alkyl)-NR$^A$—, —(C$_{1-4}$alkyl)-SO$_2$—, —C(O)—(C$_{1-4}$alkyl)-, —O—(C$_{1-4}$alkyl), —C(O)O—(C$_{1-4}$alkyl)-, —NR$^A$—(C$_{1-4}$alkyl)-, —(C$_{1-4}$alkyl)-O—(C$_{1-4}$alkyl)-, —(C$_{1-4}$alkyl)-C(O)—(C$_{1-4}$alkyl)-, —(C$_{1-4}$alkyl)-OC(O)—(C$_{1-4}$alkyl)-, —(C$_{1-4}$alkyl)-C(O)O—(C$_{1-4}$alkyl)-, —(C$_{2-4}$alkyl)-NR$^A$—(C$_{1-4}$alkyl)-, —(C$_{1-4}$alkyl)-SO$_2$—(C$_{1-4}$alkyl)-, —C(O)—NR$^A$—, —C(O)—NR$^A$—(C$_{1-4}$alkyl)-, —NR$^A$—C(O)— and —NR$^A$—C(O)—(C$_{1-4}$alkyl)-;

wherein the —C$_{1-4}$alkyl- or C$_{2-4}$alkyl, whether alone or as part of a substituent group is optionally substituted with one or more substituents independently selected from the group consisting of hydroxy, C$_{1-4}$alkoxy, amino, (C$_{1-4}$alkyl)amino, di(C$_{1-4}$alkyl)amino, phenyl, SH and S(C$_{1-4}$alkyl);

wherein R$^A$ is selected from the group consisting of hydrogen, —C$_{1-4}$alkyl phenyl, —C(O)—(C$_{1-4}$alkyl), —C(O)-carbocyclyl, —C(O)-heterocyclyl, —SO$_2$—(C$_{1-4}$alkyl)-SO$_2$-carbocyclyl and —SO$_2$-heterocyclyl;

provided that the chain length of L$^1$, not counting branching, is one to six atoms;

R$^1$ is selected from the group consisting of hydrogen, C$_{1-4}$alkyl, cycloalkyl, partially unsaturated carbocyclyl, aryl, biphenyl, heteroaryl and heterocycloalkyl;

wherein the cycloalkyl, partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, C$_{1-4}$alkyl, C$_{1-4}$alkoxy, halogenated C$_{1-4}$alkyl, halogenated C$_{1-4}$alkoxy, hydroxy substituted C$_{1-4}$alkyl, cyano, nitro, amino, C$_{1-4}$alkylamino, di(C$_{1-4}$alkyl)amino, [1,3]dioxolanyl, alkoxy-C(O)—, NR$^B$R$^C$—C(O)— and —SO$_2$—NR$^B$R$^C$;

wherein R$^B$ and R$^C$ are each independently selected from the group consisting of hydrogen and C$_{1-4}$alkyl;

b is an integer from 0 to 1;

L$^2$ is selected from the group consisting of —C$_{1-4}$alkyl-, —CH$_2$—C$_{2-4}$alkenyl-, —CH$_2$—C$_{2-4}$alkynyl-, —SO$_2$—, —C(O)—, —C(O)O—, —(C$_{1-4}$alkyl)-C(O)—, —(C$_{1-4}$alkyl)-O—, —(C$_{1-4}$alkyl)-C(O)O—, —(C$_{2-4}$alkyl)-NR$^D$—, —(C$_{1-4}$alkyl)-SO$_2$—, —C(O)—(C$_{1-4}$alkyl)-, —O—(C$_{1-4}$alkyl), —C(O)O—(C$_{1-4}$alkyl)-, —NR$^D$—(C$_{1-4}$alkyl)-, —(C$_{1-4}$alkyl)-O—(C$_{1-4}$alkyl)-, —(C$_{1-4}$alkyl)-C(O)—(C$_{1-4}$alkyl)-, —(C$_{1-4}$alkyl)-OC(O)—(C$_{1-4}$alkyl)-, —(C$_{1-4}$alkyl)-C(O)O—(C$_{1-4}$alkyl)-, —(C$_{2-4}$alkyl)-NR$^D$—(C$_{1-4}$alkyl)-, —(C$_{1-4}$alkyl)-SO$_2$—(C$_{1-4}$alkyl)-, —C(O)—NR$^D$—, —C(O)—NR$^D$—(C$_{1-4}$alkyl)-, —NR$^D$—C(O)— and —NR$^D$C(O)—(C$_{1-4}$alkyl)-;

wherein the —C$_{1-4}$alkyl- or C$_{2-4}$alkyl, whether alone or as part of a substituent group is optionally substituted with one or more substituents independently selected from the group consisting of hydroxy, C$_{1-4}$alkoxy, amino, (C$_{1-4}$alkyl)amino, di(C$_{1-4}$alkyl)amino, phenyl, SH and S(C$_{1-4}$alkyl);

wherein R$^D$ is selected from the group consisting of hydrogen, —C$_{1-4}$alkyl phenyl, —C(O)—(C$_{1-4}$alkyl), —C(O)-carbocyclyl, —C(O)-heterocyclyl, —SO$_2$—(C$_{1-4}$alkyl)-SO$_2$-carbocyclyl and —SO$_2$-heterocyclyl;

provided that the chain length of L$^2$, not counting branching, is one to six atoms;

R$^2$ is selected from the group consisting of hydrogen, C$_{1-4}$alkyl, cycloalkyl, partially unsaturated carbocyclyl, aryl, biphenyl, heteroaryl and heterocycloalkyl;

wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, C$_{1-4}$alkyl, C$_{1-4}$alkoxy, halogenated C$_{1-4}$alkyl, halogenated C$_{1-4}$alkoxy, hydroxy substituted C$_{1-4}$alkyl, cyano, nitro, amino, C$_{1-4}$alkylamino, di(C$_{1-4}$alkyl)amino, [1,3]dioxolanyl, —C$_{1-4}$alkoxy-C(O)—, NR$^E$R$^F$—C(O)— and —SO$_2$—NR$^E$R$^F$;

wherein R$^E$ and R$^F$ are each independently selected from the group consisting of hydrogen and C$_{1-4}$alkyl;

provided that the chain length of $L^1$, not counting branching, plus the chain length of $L^2$, not counting branching, is not greater than about 12 atom;

provided further that when a is 0 and b is 0 then $R^1$ and $R^2$ are not each hydrogen;

provided further than when ---- is a double bond, X and Y are each =O, a is 0, $R^1$ is hydrogen, b is 1 and $L^2$ is —$CH_2$—, then $R^2$ is other than 2,4-dimethoxyphenyl;

provided further than when ---- is a double bond, X and Y are each=O, a is 1, $L^1$ is —$CH_2$—, b is 0 and $R^2$ is hydrogen, then $R^1$ is other than 2,4-dimethoxyphenyl;

provided further than when ---- is a single bond, X and Y are each =O, a is 1, $L^1$ is —$CH(CH_3)$—, b is 1 and $L^2$ is —$CH(CH_3)$—, then $R^1$ and $R^2$ are not each phenyl;

or a pharmaceutically acceptable salt thereof. The compound s of formula (CI) and (CII) are useful as intermediates in the synthesis of compounds of formula (I) and compounds of formula (II), respectively.

The present invention is further directed to compounds of formula (CIII) and compounds of formula (CIV)

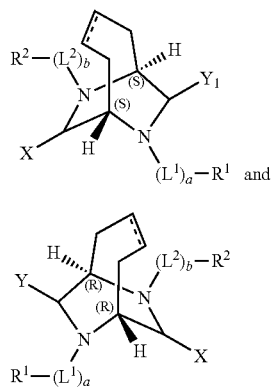

(CIII)

(CIV)

wherein

---- is a single or double bond;

X and Y are each independently selected from the group consisting of hydrogen and =O;

a is an integer from 0 to 1;

$L^1$ is selected from the group consisting of —$C_{1-4}$alkyl-, —$CH_2$—$C_{2-4}$alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)O—, —($C_{2-4}$alkyl)-$NR^A$, —($C_{1-4}$alkyl)-$SO_2$—, —C(O)—($C_{1-4}$alkyl)-, —O—($C_{1-4}$alkyl), —C(O)O—($C_{1-4}$alkyl)-, —$NR^A$—($C_{1-4}$alkyl)-, —($C_{1-4}$alkyl)-O—($C_{1-4}$alkyl)-, —($C_{1-4}$alkyl)-C(O)—($C_{1-4}$alkyl)-, —($C_{1-4}$alkyl)-OC(O)—($C_{1-4}$alkyl)-, —($C_{1-4}$alkyl)-C(O)O—($C_{1-4}$alkyl)-, —($C_{2-4}$alkyl)-$NR^A$($C_{1-4}$alkyl)-, —($C_{1-4}$alkyl)-$SO_2$—($C_{1-4}$alkyl)-, —C(O)—$NR^A$—, —C(O)—$NR^A$—($C_{1-4}$alkyl)-, —$NR^A$—C(O)— and —$NR^A$—C(O)—($C_{1-4}$alkyl)-;

wherein the —$C_{1-4}$alkyl- or $C_{2-4}$alkyl, whether alone or as part of a substituent group is optionally substituted with one or more substituents independently selected from the group consisting of hydroxy, $C_{1-4}$alkoxy, amino, ($C_{1-4}$alkyl)amino, di($C_{1-4}$alkyl)amino, phenyl, SH and S($C_{1-4}$alkyl);

wherein $R^A$ is selected from the group consisting of hydrogen, —$C_{1-4}$alkyl phenyl, —C(O)—($C_{1-4}$alkyl), —C(O)-carbocyclyl, —C(O)-heterocyclyl, —$SO_2$—($C_{1-4}$alkyl)-$SO_2$-carbocyclyl and —$SO_2$-heterocyclyl;

provided that the chain length of $L^1$, not counting branching, is one to six atoms;

$R^1$ is selected from the group consisting of hydrogen, $C_{1-4}$alkyl, cycloalkyl, partially unsaturated carbocyclyl, aryl, biphenyl, heteroaryl and heterocycloalkyl;

wherein the cycloalkyl, partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, $C_{1-4}$alkyl, $C_{1-4}$alkoxy, halogenated $C_{1-4}$alkyl, halogenated $C_{1-4}$alkoxy, hydroxy substituted $C_{1-4}$alkyl, cyano, nitro, amino, $C_{1-4}$alkylamino, di($C_{1-4}$alkyl)amino, [1,3]dioxolanyl, alkoxy-C(O)—, $NR^BR^C$—C(O)— and —$SO_2$—$NR^BR^C$;

wherein $R^B$ and $R^C$ are each independently selected from the group consisting of hydrogen and $C_{1-4}$alkyl;

b is an integer from 0 to 1;

$L^2$ is selected from the group consisting of —$C_{1-4}$alkyl-, —$CH_2$—$C_{2-4}$alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)O—, —($C_{2-4}$alkyl)-$NR^D$, —($C_{1-4}$alkyl)-$SO_2$—, —C(O)—($C_{1-4}$alkyl)-, —O—($C_{1-4}$alkyl), —C(O)O—($C_{1-4}$alkyl)-, —$NR^D$—($C_{1-4}$alkyl)-, —($C_{1-4}$alkyl)-O—($C_{1-4}$alkyl)-, —($C_{1-4}$alkyl)-C(O)—($C_{1-4}$alkyl)-, —($C_{1-4}$alkyl)-OC(O)—($C_{1-4}$alkyl)-, —($C_{1-4}$alkyl)-C(O)O—($C_{1-4}$alkyl)-, —($C_{2-4}$alkyl)-$NR^D$—($C_{1-4}$alkyl)-, —($C_{1-4}$alkyl)-$SO_2$—($C_{1-4}$alkyl)-, —C(O)—$NR^D$—, —C(O)—$NR^D$($C_{1-4}$alkyl)-, —$NR^D$—C(O)— and —$NR^D$—C(O)—($C_{1-4}$alkyl)-;

wherein the —$C_{1-4}$alkyl- or $C_{2-4}$alkyl, whether alone or as part of a substituent group is optionally substituted with one or more substituents independently selected from the group consisting of hydroxy, $C_{1-4}$alkoxy, amino, ($C_{1-4}$alkyl)amino, di($C_{1-4}$alkyl)amino, phenyl, SH and S($C_{1-4}$alkyl);

wherein $R^D$ is selected from the group consisting of hydrogen, —$C_{1-4}$alkyl phenyl, —C(O)—($C_{1-4}$alkyl), —C(O)-carbocyclyl, —C(O)-heterocyclyl, —$SO_2$—($C_{1-4}$alkyl)-$SO_2$-carbocyclyl and —$SO_2$-heterocyclyl;

provided that the chain length of $L^2$, not counting branching, is one to six atoms;

$R^2$ is selected from the group consisting of hydrogen, $C_{1-4}$alkyl, cycloalkyl, partially unsaturated carbocyclyl, aryl, biphenyl, heteroaryl and heterocycloalkyl;

wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, $C_{1-4}$alkyl, $C_{1-4}$alkoxy, halogenated $C_{1-4}$alkyl, halogenated $C_{1-4}$alkoxy, hydroxy substituted $C_{1-4}$alkyl, cyano, nitro, amino, $C_{1-4}$alkylamino, di($C_{1-4}$alkyl)amino, [1,3]dioxolanyl, —$C_{1-4}$alkoxy-C(O)—, $NR^ER^F$—C(O)— and —$SO_2$—$NR^ER^F$;

wherein $R^E$ and $R^F$ are each independently selected from the group consisting of hydrogen and $C_{1-4}$alkyl;

provided that the chain length of $L^1$, not counting branching, plus the chain length of $L^2$, not counting branching, is not greater than about 12 atom;

provided further that when a is 0 and b is 0 then $R^1$ and $R^2$ are not each hydrogen;

provided further than when ---- is a double bond, X and Y are each=O, a is 0, $R^1$ is hydrogen, b is 1 and $L^2$ is —$CH_2$—, then $R^2$ is other than 2,4-dimethoxyphenyl;

provided further than when ---- is a double bond, X and Y are each=O, a is 1, $L^1$ is —$CH_2$—, b is 0 and $R^2$ is hydrogen, then $R^1$ is other than 2,4-dimethoxyphenyl;

provided further than when ---- is a single bond, X and Y are each =O, a is 1, $L^1$ is —$CH(CH_3)$—, b is 1 and $L^2$ is —$CH(CH_3)$—, then $R^1$ and $R^2$ are not each phenyl;

or a pharmaceutically acceptable salt thereof. The compounds of formula (CIII) and (CIV) are useful as intermediates in the synthesis of compounds of formula (I) and compounds of formula (II), respectively.

The present invention is further directed to compounds of formula (CV) and (CVI)

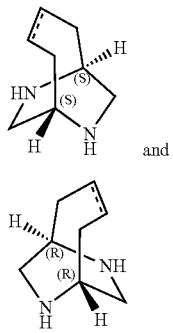

(H,H) useful in preparation of the compounds of formula (I) and (II).

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating unipolar depression, depression, major depressive disorder, childhood depression, dysthymia, bipolar disorder, mild cognitive impairment, Alzheimer's disease, epilepsy, schizophrenia, obsessive compulsive disorder, anxiety, panic disorder, post-traumatic stress disorder, premenstrual dysphoric disorder, vasomotor symptoms associated with menopause (i.e. hot flashes), premature ejaculation, sexual dysfunction, urinary incontinence, constipation-predominant IBS, chronic constipation, colonic inertia, idiopathic colonic pseudoobstruction, comprising administering to a subject in need thereof, a therapeutically effective amount of any of the compounds or pharmaceutical compositions described above.

Another example of the invention is the use of any of the compounds described herein in the preparation of a medicament for treating: (a) unipolar depression, (b) major depressive disorder, (c) childhood depression, (d) dysthymia, (e) bipolar disorder, (f) mild cognitive impairment, (g) Alzheimer's disease, (h) epilepsy, (i) schizophrenia, (j) obsessive compulsive disorder, (k) anxiety, (l) panic disorder, (m) post-traumatic stress disorder, (n) premenstrual dysphoric disorder, (o) vasomotor symptoms associated with menopause, (p) premature ejaculation, (q) sexual dysfunction, (r) urinary incontinence, (s) constipation-predominant IBS, (t) chronic constipation, (u) colonic inertia, (v) idiopathic colonic pseudoobstruction, in a subject in need thereof.

DETAILED DESCRIPTION OF THE INVENTION

The present invention is directed to compounds of formula (I) and compounds of formula (II)

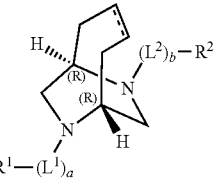

wherein ═══ a, $L^1$, $R^1$, b, $L^2$ and $R^2$ are as herein defined.

The compounds of the present invention are either serotonin transport inhibitors or $5HT_{1A}$ antagonists or $5HT_{1A}$ agonist or $5HT_{1A}$ partial agonists or dual activity serotonin transport inhibitors and $5HT_{1A}$ modulators.

The compounds of the present invention, depending on their activity against the $5HT_{1A}$ receptor and serotonin transport, include, but are not limited to depression (including unipolar depression, major depressive disorder, childhood depression, dysthymia), manic depression (bipolar disorder), mild cognitive impairment, Alzheimer's disease, epilepsy, schizophrenia, obsessive compulsive disorder, anxiety, panic disorder, post-traumatic stress disorder, premenstrual dysphoric disorder, vasomotor symptoms associated with menopause (i.e. hot flashes), premature ejaculation, sexual dysfunction, urinary incontinence, constipation-predominant IBS, chronic constipation, colonic inertia, idiopathic colonic pseudoobstruction and related disorders.

Compounds of the present invention which are serotonin transport inhibitors are useful in the treatment of, for example, depression. Compounds of the present invention which are $5HT_{1A}$ antagonists are useful in the treatment of, for example, Alzheimer's disease and mild cognitive impairment. Compounds of the present invention which are $5HT_{1A}$ agonists are useful in the treatment of, for example, anxiety. Compounds of the present invention which are $5HT_{1A}$ partial agonists are useful in the treatment of, for example, anxiety. Compounds of the present invention which are dual activity serotonin transport inhibitors and $5HT_{1A}$ modulators are useful in the treatment of, for example, depression.

Preferably, the compounds of the present invention are useful for the treatment of depression and related disorders. More preferably, the compounds of the present invention are useful for the treatment of depression and related disorders, with a rapid onset of action (e.g. wherein the onset of action, as measured by in vivo assays is less than about 4 weeks, preferably less than about 2 weeks, more preferably, less than about 1 week.)

In an embodiment, the present invention is directed to compounds of formula (I) wherein ═══ is a double bond. In another embodiment, the present invention is directed to compounds of formula (I) wherein ═══ is a single bond.

In an embodiment, the present invention is directed to compounds of formula (II) wherein ═══ is a double bond. In another embodiment, the present invention is directed to compounds of formula (II) wherein ═══ is a single bond.

In an embodiment of the present invention, ═══ is a double bond. In another embodiment of the present invention, ═══ is a single bond.

In an embodiment of the present invention, a is 0. In another embodiment of the present invention, a is 1. In an embodiment of the present invention, b is 0. In another embodiment of the present invention b is 1. In an embodiment of the present invention, a and b are each 1. In another embodiment of the present invention one of a and b is 1 and the other of a and b is 0.

In an embodiment of the present invention, $L^1$ is selected form the group consisting of $C_{1-4}$alkyl-, —C(O)O— —C(O)—$C_{1-4}$alkyl- (wherein the $C_{1-4}$alkyl is optionally substituted with phenyl) and —C(O)—N(phenyl)-. In another embodiment of the present invention, $L^1$ is selected form the group consisting of —CH$_2$—, —C(O)O—, —C(O)—, —C(O)—CH(phenyl)-, —C(O)—N(phenyl)- and —C(O)—CH$_2$CH$_2$—.

In an embodiment of the present invention, $L^2$ is selected form the group consisting of $C_{1-4}$alkyl-, —C(O)O— —C(O)—$C_{1-4}$alkyl- (wherein the $C_{1-4}$alkyl is optionally substituted with phenyl) and —C(O)—N(phenyl)-. In another embodiment of the present invention, $L^2$ is selected form the group consisting of —CH$_2$—, —C(O)O—, —C(O)—, —C(O)—CH(phenyl)-, —C(O)—N(phenyl)- and —C(O)—CH$_2$CH$_2$—.

In an embodiment of the present invention, $L^1$ is selected from the group consisting of —C$_{1-4}$alkyl-, —C$_{1-4}$alkyl- (wherein the C$_{1-4}$alkyl is substituted with a hydroxy group), —C$_{1-4}$alkyl-O—, —C$_{1-4}$alkyl-O— (wherein the C$_{1-4}$alkyl is substituted with a hydroxy group), —C$_{2-4}$alkyl-NH—, —C$_{2-4}$ alkyl-NH—C$_{1-4}$alkyl- (wherein the C$_{2-4}$alkyl is substituted with a hydroxy group), —CH$_2$—C$_{2-4}$alkynyl- and —C(O)O—. In another embodiment of the present invention, $L^1$ is selected from the group consisting of —CH$_2$—, —CH$_2$—CH$_2$—, —CH$_2$—CH$_2$—CH(OH)—, —CH$_2$—CH$_2$—CH$_2$—O—, —CH$_2$—CH$_2$—NH—, —CH$_2$—CC—, —CH$_2$—CH(S—OH)—CH$_2$—O—, CH$_2$—CH(R—OH)—CH$_2$—O—, —CH$_2$—CH(S—OH)—CH$_2$—NH—CH$_2$— and —C(O)O—.

In an embodiment of the present invention, $L^2$ is selected from the group consisting of —C$_{1-4}$alkyl-, —C$_{1-4}$alkyl- (wherein the C$_{1-4}$alkyl is substituted with a hydroxy group), —C$_{1-4}$alkyl-O—, —C$_{1-4}$alkyl-O— (wherein the C$_{1-4}$alkyl is substituted with a hydroxy group), —C$_{2-4}$alkyl-NH—, —C$_{2-4}$ alkyl-NH—C$_{1-4}$alkyl- (wherein the C$_{2-4}$alkyl is substituted with a hydroxy group), —CH$_2$—C$_{2-4}$alkynyl- and —C(O)O—. In another embodiment of the present invention, $L^2$ is selected from the group consisting of —CH$_2$—, —CH$_2$—CH$_2$—, —CH$_2$—CH$_2$—CH(OH)—, —CH$_2$—CH$_2$—CH$_2$—O—, —CH$_2$—CH$_2$—NH—, —CH$_2$—CC—, —CH$_2$—CH(S—OH)—CH$_2$—O—, CH$_2$—CH(R—OH)—CH$_2$—O—, —CH$_2$—CH(S—OH)—CH$_2$—NH—CH$_2$— and —C(O)O—.

In an embodiment of the present invention, $R^1$ is selected from the group consisting of hydrogen, t-butyl, phenyl, 4-methylphenyl, 4-t-butyl-phenyl, 2-methoxy-phenyl, 2-chlorophenyl, 3-chlorophenyl, 4-chlorophenyl, 3,4-dichlorophenyl, 2,4-dimethoxy-phenyl, 3-trifluoromethylphenyl, 4-trifluoromethylphenyl, 3-trifluoromethyl-4-chloro-phenyl, 3-methyl-4-fluoro-phenyl, 1-naphthyl, 2-naphthyl, 2-(6-methoxy-naphthyl), 2-(1,2,3,4-tetrahydro-naphthyl), 2-(9H-fluorenyl), 1-biphenyl, 2-biphenyl, 3-biphenyl, 3-quinolinyl, 5-quinolinyl, 6-quinolinyl, 6-(2,3-dihydro-benzo[1,4]dioxinyl), 5-(benzo[1,3]doxolyl), 1-(2-[1,3]dioxolanyl)-phenyl and 3-(2-[1,3]dioxolanyl)-phenyl.

In another embodiment of the present invention, $R^1$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chlorophenyl, 3-fluoro-4-methoxy-phenyl, 2-ethoxy-carbonyl-phenyl, 4-ethoxy-carbonyl-phenyl, 2-naphthyl, 1-(8-methyl-naphthyl), 2-(6-methoxy-naphthyl), 4-(9H-carbazolyl), 2-biphenyl, 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In an embodiment of the present invention, $R^2$ is selected from the group consisting of hydrogen, t-butyl, phenyl, 4-methylphenyl, 4-t-butyl-phenyl, 2-methoxy-phenyl, 2-chlorophenyl, 3-chlorophenyl, 4-chlorophenyl, 3,4-dichlorophenyl, 2,4-dimethoxy-phenyl, 3-trifluoromethylphenyl, 4-trifluoromethylphenyl, 3-trifluoromethyl-4-chloro-phenyl, 3-methyl-4-fluoro-phenyl, 1-naphthyl, 2-naphthyl, 2-(6-methoxy-naphthyl), 2-(1,2,3,4-tetrahydro-naphthyl), 2-(9H-fluorenyl), 1-biphenyl, 2-biphenyl, 3-biphenyl, 3-quinolinyl, 5-quinolinyl, 6-quinolinyl, 6-(2,3-dihydro-benzo[1,4]dioxinyl), 5-(benzo[1,3]doxolyl), 1-(2-[1,3]dioxolanyl)-phenyl and 3-(2-[1,3]dioxolanyl)-phenyl.

In another embodiment of the present invention, $R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 3-fluoro-4-methoxy-phenyl, 2-ethoxy-carbonyl-phenyl, 4-ethoxy-carbonyl-phenyl, 2-naphthyl, 1-(8-methyl-naphthyl), 2-(6-methoxy-naphthyl), 4-(9H-carbazolyl), 2-biphenyl, 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In an embodiment of the present invention, $L^1$ is selected from the group consisting of —C$_{1-4}$alkyl-, —CH$_2$—C$_{2-4}$alkenyl-, —CH$_2$—C$_{2-4}$alkynyl-, —C(O)—, —C(O)O—, —(C$_{1-4}$ alkyl)-C(O)—, —(C$_{1-4}$alkyl)-O—, —(C$_{1-4}$alkyl)-C(O)O—, —(C$_{2-4}$alkyl)-NR$^A$—, —C(O)—(C$_{1-4}$alkyl)-, —C(O)O—(C$_{1-4}$alkyl)-, —(C$_{1-4}$alkyl)-O—(C$_{1-4}$alkyl)-, —C(O)—NR$^A$—, —C(O)—NR$^A$—(C$_{1-4}$alkyl)-, —NR$^A$—C(O)— and —NR$^A$—C(O)—(C$_{1-4}$alkyl)-; wherein the —C$_{1-4}$alkyl-, whether alone or as part of a substituent group is optionally substituted with one to two substituents independently selected from the group consisting of hydroxy, C$_{1-4}$alkoxy, amino, ($C_{1-4}$alkyl)amino, di($C_{1-4}$alkyl)amino and phenyl; and wherein $R^A$ is selected from the group consisting of hydrogen, —$C_{1-4}$alkyl phenyl and —C(O)—($C_{1-4}$alkyl).

In another embodiment of the present invention, $L^1$ is selected from the group consisting of —$C_{1-4}$alkyl-, —C(O)O—, —C(O)—, —C(O)—$C_{1-4}$alkyl-, —C(O)—$NR^A$— and —C(O)—$C_{1-4}$alkyl-; wherein the $C_{1-4}$alkyl, whether alone or as part of a substituent group, is optionally substituted with phenyl; and wherein $R^A$ is phenyl.

In another embodiment of the present invention, $L^1$ is selected from the group consisting of —$CH_2$—, —C(O)O—, —C(O)—, —C(O)—CH(phenyl)-, —C(O)—N(phenyl)- and —C(O)—$CH_2$—$CH_2$—. In another embodiment of the present invention, $L^1$ is selected from the group consisting of —C(O)O—, —C(O)—, —C(O)—CH(phenyl)-, —C(O)—N(phenyl)- and —C(O)—$CH_2$—$CH_2$—. In another embodiment of the present invention, $L^1$ is selected from the group consisting of —C(O)—, —C(O)—CH(phenyl)-, —C(O)—N(phenyl)- and —C(O)—$CH_2$—$CH_2$—.

In another embodiment of the present invention, $L^1$ is selected from the group consisting of —$CH_2$— and —C(O)O—. In another embodiment of the present invention, $L^1$ is —$CH_2$—. In another embodiment of the present invention, $L^1$ is —C(O)O—.

In an embodiment of the present invention, $L^2$ is selected from the group consisting of —$C_{1-4}$alkyl-, —$CH_2$—$C_{2-4}$alkenyl-, —$CH_2$—$C_{2-4}$alkynyl-, —C(O)—, —C(O)O—, —($C_{1-4}$ alkyl)-C(O)—, —($C_{1-4}$alkyl)-O—, —($C_{1-4}$alkyl)-C(O)O—, —($C_{2-4}$alkyl)-$NR^D$—, —C(O)—($C_{1-4}$alkyl)-, —C(O)O—($C_{1-4}$alkyl)-, —($C_{1-4}$alkyl)-O—($C_{1-4}$alkyl)-, —($C_{2-4}$alkyl)-$NR^D$—($C_{1-4}$alkyl)-, —C(O)—$NR^D$—, —C(O)—$NR^D$—($C_{1-4}$alkyl)-, —$NR^D$—C(O)— and —$NR^D$—C(O)—($C_{1-4}$alkyl)-; wherein the —$C_{1-4}$alkyl-, whether alone or as part of a substituent group is optionally substituted with one to two substituents independently selected from the group consisting of hydroxy, $C_{1-4}$alkoxy, amino, ($C_{1-4}$alkyl)amino, di($C_{1-4}$alkyl)amino and phenyl; and wherein $R^D$ is selected from the group consisting of hydrogen, —$C_{1-4}$alkyl phenyl and —C(O)—($C_{1-4}$alkyl).

In another embodiment of the present invention, $L^2$ is selected from the group consisting of —$C_{1-4}$alkyl-, —$CH_2$—$C_{2-4}$alkynyl-, —$C_{1-4}$alkyl-O—, —$C_{2-4}$alkyl-NH—, —$C_{2-4}$alkyl-NH—$C_{1-4}$alkyl- and —C(O)O—; wherein the $C_{1-4}$alkyl or $C_{2-4}$alkyl, whether alone or as part of a substituent group is optionally substituted with hydroxy.

In another embodiment of the present invention, $L^2$ is selected from the group consisting of —C(O)O—, —$CH_2$—, —$CH_2$—$CH_2$—, —$CH_2$—CC—, —$CH_2$—$CH_2$—O—, —$CH_2$—$CH_2$—$CH_2$—O—, —$CH_2$—$CH_2$—CH(OH)—, —$CH_2$—$CH_2$—NH—, —$CH_2$—CH(S—OH)—$CH_2$—O—, —$CH_2$—CH(R—OH)—$CH_2$—O— and —$CH_2$—CH(S—OH)—$CH_2$—NH—$CH_2$—. In another embodiment of the present invention, $L^2$ is selected from the group consisting of —$CH_2$—, —$CH_2$—$CH_2$—, —$CH_2$—CC—, —$CH_2$—$CH_2$—O—, —$CH_2$—$CH_2$—$CH_2$—O—, —$CH_2$—$CH_2$—CH(OH)—, —$CH_2$—$CH_2$—NH—, —$CH_2$—CH(S—OH)—$CH_2$—O—, —$CH_2$—CH(R—OH)—$CH_2$—O— and —$CH_2$—CH(S—OH)—$CH_2$—NH—$CH_2$—.

In another embodiment of the present invention, $L^2$ is selected from the group consisting of —C(O)O—, —$CH_2$—, —$CH_2$—CH(R—OH)—$CH_2$—O— and —$CH_2$—CH(S—OH)—$CH_2$—O—. In another embodiment of the present invention, $L^2$ is selected from the group consisting of —C(O)O—, —$CH_2$—CH(R—OH)—$CH_2$—O— and —$CH_2$—CH(S—OH)—$CH_2$—O—.

In another embodiment of the present invention, $L^2$ is selected from the group consisting of —$CH_2$—, —C(O)O— and —$CH_2$—CH(S—OH)—$CH_2$—O—. In another embodiment of the present invention, $L^2$ is —$CH_2$—.

In an embodiment of the present invention, $R^1$ is selected from the group consisting of hydrogen, $C_{1-4}$alkyl, cycloalkyl, aryl, biphenyl, heteroaryl and heterocycloalkyl; wherein the aryl, heteroaryl or heterocycloalkyl, whether alone or as part of a substituent group is optionally substituted with one to three substituents independently selected from the group consisting of halogen, hydroxy, carboxy, oxo, $C_{1-4}$alkyl, $C_{1-4}$alkoxy, fluorinated $C_{1-4}$alkyl, fluorinated $C_{1-4}$alkoxy, hydroxy substituted $C_{1-4}$alkyl, cyano, nitro, amino, $C_{1-4}$alkylamino, di($C_{1-4}$alkyl)amino, [1,3]dioxolanyl, $C_{1-4}$alkoxy-C(O)— and $NR^BR^C$—C(O)—; and wherein $R^B$ and $R^C$ are each independently selected from the group consisting of hydrogen and $C_{1-4}$alkyl.

In another embodiment of the present invention, $R^1$ is selected from the group consisting of hydrogen, $C_{1-4}$alkyl, aryl, biphenyl, heteroaryl and heterocycloalkyl; wherein the aryl is optionally substituted with one to two substituents independently selected from the group consisting of halogen, $C_{1-4}$alkyl and $C_{1-4}$alkoxy.

In another embodiment of the present invention, $R^1$ is selected from the group consisting of hydrogen, t-butyl, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl), 1-biphenyl, 2-biphenyl, 3-quinolinyl, 5-quinolinyl and 6-(2,3-dihydro-benzo[1,4]dioxinyl). In another embodiment of the present invention, $R^1$ is selected from the group consisting of hydrogen, t-butyl, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl), 2-biphenyl, 3-quinolinyl, 5-quinolinyl and 6-(2,3-dihydro-benzo[1,4]dioxinyl). In another embodiment of the present invention, $R^1$ is selected from the group consisting of hydrogen, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl), 2-biphenyl, 3-quinolinyl, 5-quinolinyl and 6-(2,3-dihydro-benzo[1,4]dioxinyl).

In another embodiment of the present invention, $R^1$ is selected from the group consisting of hydrogen, t-butyl, phenyl, 1-biphenyl, 1-naphthyl, 2-naphthyl and 2-(1,2,3,4-tetrahydro-naphthyl). In another embodiment of the present invention, $R^1$ is selected from the group consisting of hydrogen, t-butyl, phenyl, 1-biphenyl, 1-naphthyl and 2-naphthyl. In another embodiment of the present invention, $R^1$ is selected from the group consisting of hydrogen, t-butyl, 2-naphthyl and 2-(1,2,3,4-tetrahydro-naphthyl). In another embodiment of the present invention, $R^1$ is selected from the group consisting of hydrogen, phenyl, 1-biphenyl, 1-naphthyl and 2-naphthyl. In another embodiment of the present invention, $R^1$ is selected from the group consisting of hydrogen, t-butyl and 2-naphthyl.

In an embodiment of the present invention, $R^2$ is selected from the group consisting of hydrogen, $C_{1-4}$alkyl, cycloalkyl, aryl, biphenyl, heteroaryl and heterocycloalkyl; wherein the aryl, heteroaryl or heterocycloalkyl, whether alone or as part of a substituent group is optionally substituted with one to three substituents independently selected from the group consisting of halogen, hydroxy, carboxy, oxo, $C_{1-4}$alkyl, $C_{1-4}$alkoxy, fluorinated $C_{1-4}$alkyl, fluorinated $C_{1-4}$alkoxy, hydroxy substituted $C_{1-4}$alkyl, cyano, nitro, amino, $C_{1-4}$alkylamino, di($C_{1-4}$alkyl)amino, [1,3]dioxolanyl, $C_{1-4}$alkoxy-C(O)— and —C(O)—$NR^ER^F$—C(O)—; and wherein $R^E$ and $R^F$ are each independently selected from the group consisting of hydrogen and $C_{1-4}$alkyl.

In another embodiment of the present invention, $R^2$ is selected from the group consisting of hydrogen, $C_{1-4}$alkyl, $C_{3-8}$cycloalkyl, aryl, biphenyl, heteroaryl and heterocycloalkyl; wherein the aryl, heteroaryl or heterocycloalkyl, whether alone or as part of a substituent group, is optionally substituted with one to two substituents independently selected from the group consisting of oxo, carboxy, halogen, $C_{1-4}$alkyl, $C_{1-4}$alkoxy, trifluoromethyl, hydroxy substituted $C_{1-4}$alkyl, di($C_{1-4}$alkyl)amino-carbonyl-, $C_{1-4}$alkoxy-carbonyl- and [1,3]dioxolanyl.

In another embodiment of the present invention, $R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 2-naphthyl, 1-(8-methyl-naphthyl), 2-(6-methoxy-naphthyl), 4-(9H-carbazolyl), 2-biphenyl, 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In another embodiment of the present invention, $R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 1-(8-methyl-naphthyl), 2-(6-methoxy-naphthyl), 4-(9H-carbazolyl), 2-biphenyl, 2-indanyl, 4-indolyl, 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In another embodiment of the present invention, $R^2$ is selected from the group consisting of hydrogen, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 1-(8-methyl-naphthyl), 2-(6-methoxy-naphthyl), 4-(9H-carbazolyl), 2-indanyl, 4-indolyl, 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In another embodiment of the present invention, $R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 2-naphthyl, 1-(8-methyl-naphthyl), 2-(6-methoxy-naphthyl), 4-(9H-carbazolyl), 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl.

In another embodiment of the present invention, $R^2$ is selected from the group consisting of hydrogen, t-butyl, 2,4-dimethoxy-phenyl, 2-naphthyl, 4-(1-methyl-indolyl) and 4-(2-methyl-indolyl). In another embodiment of the present invention, $R^2$ is selected from the group consisting of hydrogen, t-butyl, 2-naphthyl, 4-(1-methyl-indolyl) and 4-(2-methyl-indolyl). In another embodiment of the present invention, $R^2$ is selected from the group consisting of t-butyl, 2-naphthyl, 2-biphenyl, 2,4-dimethoxyphenyl and 4-(2-methyl-indolyl). In another embodiment of the present invention, $R^2$ is 2,4-dimethoxy-phenyl.

In an embodiment of the present invention, when a is 0 and b is 0, then $R^1$ and $R^2$ are not each hydrogen. In another embodiment of the present invention, when ═ is a double bond, X and Y are each ═O, a is 0, $R^1$ is hydrogen, b is 1 and $L^2$ is —$CH_2$—, then $R^2$ is other than 2,4-dimethoxyphenyl. In another embodiment of the present invention, when ═ is a double bond, X and Y are each ═O, a is 1, $L^1$ is —$CH_2$—, b is 0 and $R^2$ is hydrogen, then $R^1$ is other than 2,4-dimethoxyphenyl. In yet another embodiment of the present invention, when ═ is a single bond, X and Y are each ═O, a is 1, $L^1$ is —CH($CH_3$)—, b is 1 and $L^2$ is —CH($CH_3$)—, then $R^1$ and $R^2$ are not each phenyl.

In an embodiment of the present invention $L^1$ is other than —$CH_2$—. In another embodiment of the present invention $L^2$ is other than —$CH_2$—. In another embodiment of the present invention one or both of $R^1$ and $R^2$ are other then phenyl or substituted phenyl.

In an embodiment of the present invention, the substituent groups -($L^1$)$_a$—$R^1$ and -($L^2$)$_b$-$R^2$ are the same. In another embodiment of the present invention, the substitutent groups -($L^1$)$_a$-$R^1$ and -($L^2$)$_b$-$R^2$ are different.

Additional embodiments of the present invention, include those wherein the substituents selected for one or more of the variables defined herein (i.e. a, $L^1$, $R^1$, b, $L^2$ and $R^2$) are independently selected to be any individual substituent or any subset of substituents selected from the complete list as defined herein.

In an embodiment of the present invention are compounds of formula (I) and/or formula (II) whose $pIC_{50}$ against the 5HTT receptor, as measured according to the procedure described in Example 77 is greater than or equal to about 6, preferably, greater than about 8.

In another embodiment of the present invention are compounds of formula (I) and/or formula (II) whose $pIC_{50}$ against the $5HT_{1A}$ receptor, as measured according to the procedure described in Example 77 is greater than or equal to about 6, preferably, greater than about 8.

In another embodiment of the present invention are compounds of formula (I) and/or formula (II) whose $pIC_{50}$ against the $5HT_{1A}$ receptor, as measured according to the procedure described in Example 78, in agonist mode, is greater than or equal to about 5, preferably, greater than about 6.5.

In another embodiment of the present invention are compounds of formula (I) and/or formula (II) whose $pIC_{50}$ against the $5HT_{1A}$ receptor, as measured according to the procedure described in Example 78, in antagonist mode, is greater than or equal to about 5, preferably, greater than about 6.5.

In an embodiment of the present invention is any single compound or subset of compounds selected from the representative compounds listed in Tables 1-4, below. In an embodiment of the present invention is any single intermediate compound or subset of intermediate compounds selected from the representative compounds listed in Tables 5-8, below.

Representative compounds of the present invention are as listed in Table 1-4, below. Representative intermediates in the synthesis of the compounds of the present invention are as listed in Tables 5-8, below.

Unless otherwise note, the $L^1$ and $L^2$ groups are incorporated in the molecule such that the first listed attachment point is bound to the bridged aryl piperazine core and the last listed attachment point is bound to the $R^1$ or $R^2$ group, respectively. Thus for example, for the $L^2$ group —$CH_2$—$CH(R—OH)$—$CH_2O$—, the —$CH_2$ portion of the $L^2$ group is bound to the bridged aryl piperazine core and the O— portion of the $L^2$ group is bound to the $R^2$ group.

TABLE 1

Representative Compounds of Formula (I)
(---- is a Double Bond)

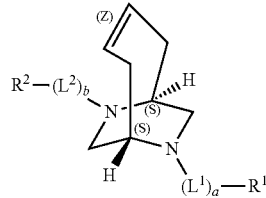

| ID No | $(L^1)_a$ | $R^1$ | $(L^2)_b$ | $R^2$ |
|---|---|---|---|---|
| 1 | a = 0 | 2-naphthyl | —$CH_2$—$CH(S—OH)$—$CH_2$—O— | 4-indolyl |
| 2 | a = 0 | H | b = 0 | 6-(2,3-dihydro-benzo[1,4]dioxinyl) |
| 3 | a = 0 | 6-(2,3-dihydro-benzo[1,4]dioxinyl) | —$CH_2$—$CH(R—OH)$—$CH_2$—O— | 4-indolyl |
| 4 | a = 0 | 2-naphthyl | —$CH_2$— | 2,4-dimethoxy-phenyl |
| 5 | a = 0 | 2-(9H-fluorenyl) | —$CH_2$— | 8-(7,8-dihydro-3H-6,9-dioxa-3-aza-cyclopenta[a]-naphthyl) |
| 6 | a = 0 | 2-naphthyl | —$CH_2$—$CH_2$—C(O)— | 3-benzothienyl |
| 7 | a = 0 | 2-naphthyl | —$CH_2$—$CH_2$—CH(OH)— | 3-benzothienyl |
| 8 | a = 0 | 2-naphthyl | —$CH_2$— | 1-(8-methyl-naphthyl) |
| 9 | a = 0 | 2-naphthyl | —$CH_2$— | cyclooctyl |
| 10 | a = 0 | 2-naphthyl | —$CH_2$—$CH(S—OH)$—$CH_2$—NH—$CH_2$— | 3-benzothienyl |
| 11 | a = 0 | H | —$CH_2$— | 2,4-dimethoxy-phenyl |
| 14 | a = 0 | 4-methyl-phenyl | b = 0 | H |
| 15 | a = 0 | H | b = 0 | 4-fluoro-phenyl |
| 16 | a = 0 | H | b = 0 | 3-trifluoromethyl-phenyl |
| 17 | a = 0 | 2-naphthyl | b = 0 | H |
| 18 | a = 0 | H | b = 0 | 4-t-butyl-phenyl |
| 19 | a = 0 | H | b = 0 | 3-methyl-4-fluoro-phenyl |
| 20 | a = 0 | H | b = 0 | 4-methoxy-phenyl |
| 21 | a = 0 | phenyl | b = 0 | H |
| 22 | a = 0 | 3-quinolinyl | b = 0 | H |
| 23 | a = 0 | H | b = 0 | 2-methoxy-phenyl |
| 24 | a = 0 | H | b = 0 | 3-methoxy-phenyl |
| 25 | a = 0 | H | b = 0 | 2-chloro-phenyl |
| 28 | a = 0 | 2-biphenyl | b = 0 | H |
| 29 | a = 0 | H | b = 0 | 2-(6-methoxy- |

TABLE 1-continued

Representative Compounds of Formula (I)
(---- is a Double Bond)

| ID No | $(L^1)_a$ | $R^1$ | $(L^2)_b$ | $R^2$ |
|---|---|---|---|---|
| | | | | naphthyl) |
| 31 | a = 0 | 2-(6-methoxy-naphthyl) | —CH$_2$—CH$_2$— | 4-fluoro-phenyl |
| 32 | a = 0 | 2-biphenyl | —CH$_2$—CH$_2$— | 4-fluoro-phenyl |
| 33 | —CH$_2$— | H | b = 0 | 2-(6-methoxy-naphthyl) |
| 34 | a = 0 | 2-biphenyl | —CH$_2$— | H |
| 36 | a = 0 | 2-(6-methoxy-naphthyl) | —CH$_2$— | 2,4-dimethoxy-phenyl |
| 37 | a = 0 | 2-biphenyl | —CH$_2$— | 2,4-dimethoxy-phenyl |
| 38 | a = 0 | 2-naphthyl | —CH$_2$—CH(S—OH)—CH$_2$—O— | 4-(9H-carbazolyl) |
| 39 | a = 0 | 2-naphthyl | —CH$_2$—CH(S—OH)—CH$_2$—O— | 4-(2-methyl-indolyl) |
| 41 | a = 0 | 2-naphthyl | —CH$_2$—CC— | H |
| 42 | a = 0 | H | b = 0 | 3-chloro-phenyl |
| 43 | a = 0 | H | b = 0 | 3,4-dichloro-phenyl |
| 44 | a = 0 | 2-naphthyl | —CH$_2$—CH$_2$— | 3-(1H-quinazoline-2,4-dione) |
| 45 | a = 0 | 2-naphthyl | —CH$_2$— | 6-(2,3-dihydro-benzo[1,4]dioxinyl) |
| 46 | a = 0 | 2-naphthyl | —CH$_2$—CH(S—OH)—CH$_2$—O— | 3-(6-methyl-pyridyl) |
| 48 | a = 0 | 2-naphthyl | —CH$_2$—CH(S—OH)—CH$_2$—O— | 4-quinolinyl |
| 49 | a = 0 | 2-(9H-fluorenyl) | —CH$_2$—CH(S—OH)—CH$_2$—O— | 4-indolyl |
| 50 | a = 0 | 2-(9H-fluorenyl) | —CH$_2$—CH(S—OH)—CH$_2$—O— | 1-(4-hydroxymethyl-indolyl) |
| 51 | a = 0 | 2-naphthyl | —CH$_2$—CH(S—OH)—CH$_2$—O— | 4-(7-chloro-quinolinyl) |
| 53 | a = 0 | 2-naphthyl | —CH$_2$—CH(R—OH)—CH$_2$—O— | 4-indolyl |
| 54 | a = 0 | 2-naphthyl | —CH$_2$—CH(S—OH)—CH$_2$—O— | 5-(3,4-dihydro-1H-quinolin-2-one) |
| 55 | a = 0 | 2-naphthyl | —CH$_2$— | 8-(7,8-dihydro-3H-6,9-dioxa-3-aza-cyclopenta[a]-naphthyl) |
| 119 | a = 0 | 1-naphthyl | b = 0 | H |
| 123 | —CH$_2$— | 2-naphthyl | b = 0 | H |
| 124 | —CH$_2$— | 2-naphthyl | —CH$_2$—CH(S—OH)—CH$_2$—O— | 4-indolyl |
| 125 | a = 0 | 2-naphthyl | —CH$_2$—CH(S—OH)—CH$_2$—O— | 4-(2-dimethylamino-carbonyl-indolyl) |
| 126 | a = 0 | 2-naphthyl | —CH$_2$—CH(S—OH)—CH$_2$—O— | 4-(2-methoxy-carbonyl-indolyl) |
| 127 | a = 0 | 2-naphthyl | —CH$_2$—CH(S—OH)—CH$_2$—O— | 4-(2-methoxy-carbonyl-7-methyl-indolyl) |
| 128 | a = 0 | 2-naphthyl | —CH$_2$—CH(S—OH)—CH$_2$—O— | 4-(2-methoxy-carbonyl-7-chloro-indolyl) |
| 132 | a = 0 | 2-fluorenyl | —CH$_2$—CH(S—OH)—CH$_2$—O— | 3-(6-methyl-pyridyl) |
| 133 | a = 0 | H | b = 0 | 3-trifluoromethyl-4-chloro-phenyl |
| 134 | a = 0 | 2-fluorenyl | b = 0 | H |
| 135 | a = 0 | 3,4-dichlorophenyl | —CH$_2$—CH(S—OH)—CH$_2$—O— | 4-(2-methyl-indolyl) |
| 136 | a = 0 | 5-quinolinyl | —CH$_2$—CH(S—OH)—CH$_2$—O— | 4-(2-methyl-indolyl) |
| 137 | a = 0 | 5-quinolinyl | b = 0 | H |
| 138 | a = 0 | 2-naphthyl | —CH$_2$—CH$_2$—CH$_2$—O— | 4-(2-methyl-indolyl) |
| 140 | a = 0 | 2-naphthyl | —CH$_2$— | 3R-(7,8-dimethoxy-3a,4-dihydro-3H-chromeno[4,3-c]isoxazolyl) |

TABLE 1-continued

Representative Compounds of Formula (I)
(---- is a Double Bond)

| ID No | $(L^1)_a$ | $R^1$ | $(L^2)_b$ | $R^2$ |
|---|---|---|---|---|
| 141 | a = 0 | 2-naphthyl | —CH$_2$— | 3S-(7,8-dimethoxy-3a,4-dihydro-3H-chromeno[4,3-c]isoxazolyl) |
| 142 | a = 0 | 2-naphthyl | —CH$_2$—CH$_2$—NH— | 2-pyridyl |
| 143 | a = 0 | 2-naphthyl | —CH$_2$—CH(S—OH)—CH$_2$—O— | 4-(2-methoxy-carbonyl-6-methoxy-indolyl) |
| 145 | a = 0 | 2-(1,2,3,4-tetrahydro-naphthyl) | —CH$_2$—CH(S—OH)—CH$_2$—O— | 4-(2-methyl-indolyl) |
| 148 | a = 0 | 2-naphthyl | —CH$_2$—CH(S—OH)—CH$_2$—O | 4-(2-methyl-5-fluoro-indolyl) |
| 150 | a = 0 | 2-naphthyl | b = 0 | 2-indanyl |
| 151 | a = 0 | 2-naphthyl | —CH$_2$—CH(S—OH)—CH$_2$—O | 4-(2-methyl-7-chloro-indolyl) |
| 152 | a = 0 | 2-naphthyl | —CH$_2$—CH(S—OH)—CH$_2$—O | 4-(2,7-dimethyl-indolyl) |
| 154 | a = 0 | 2-naphthyl | —CH$_2$—CH(S—OH)—CH$_2$—O | 4-(2,5-dimethyl-indolyl) |
| 157 | a = 0 | 5-quinolinyl | —CH$_2$—CH(S—OH)—CH$_2$—O | 4-(2-methyl-indolyl) |
| 158 | a = 0 | 3-quinolinyl | —CH$_2$—CH(S—OH)—CH$_2$—O | 4-(2-methyl-indolyl) |
| 159 | a = 0 | 6-(2,3-dihydro-benzo[1,4]dioxinyl) | —CH$_2$—CH(S—OH)—CH$_2$—O | 4-(2-methyl-indolyl) |
| 160 | a = 0 | 2-naphthyl | —CH$_2$—CH(S—OH)—CH$_2$—O | 5-quinolinyl |

TABLE 2

Representative Compounds of Formula (II)
(---- is a Double Bond)

| ID No | $(L^1)_a$ | $R^1$ | $(L^2)_b$ | $R^2$ |
|---|---|---|---|---|
| 30 | a = 0 | H | b = 0 | 2-naphthyl |
| 76 | —C(O)O— | t-butyl | —C(O)O— | t-butyl |
| 77 | a = 0 | H | b = 0 | H |
| 153 | a = 0 | 2-naphthyl | —CH$_2$—CH(R—OH)—CH$_2$—O— | 4-(2-methyl-indolyl) |
| 155 | a = 0 | 2-naphthyl | —CH$_2$—CH(S—OH)—CH$_2$—O— | 4-(2-methyl-indolyl) |
| 156 | a = 0 | 2-naphthyl | —CH$_2$—CH(S—OH)—CH$_2$—O— | 4-(1-methyl-indolyl) |

TABLE 3

Representative Compounds of Formula (I)
(---- is a Single Bond)

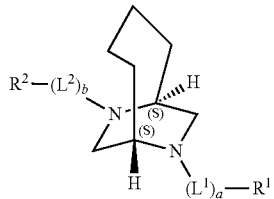

| ID No | $(L^1)_a$ | $R^1$ | $(L^2)_b$ | $R^2$ |
|---|---|---|---|---|
| 27 | a = 0 | H | b = 0 | 2-naphthyl |
| 35 | a = 0 | H | b = 0 | 2-biphenyl |
| 57 | —C(O)O— | t-butyl | —CH$_2$— | 2,4-dimethoxy-phenyl |
| 58 | a = 0 | H | —CH$_2$— | 2,4-dimethoxy-phenyl |
| 60 | —C(O)O— | t-butyl | —C(O)O— | t-butyl |
| 146 | a = 0 | 2-(1,2,3,4-tetrahydro-naphthyl) | —CH$_2$—CH(S—OH)—CH$_2$—O— | 4-(2-methyl-1H-indolyl) |
| 147 | a = 0 | 2-naphthyl | —CH$_2$—CH(S—OH)—CH$_2$—O— | 4-(2-methyl-1H-indolyl) |

TABLE 4

Representative Compounds of Formula (II)
(---- is a Single Bond)

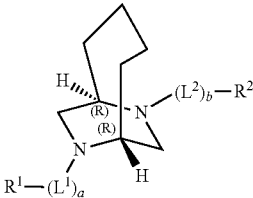

| ID No | $(L^1)_a$ | $R^1$ | $(L^2)_b$ | $R^2$ |
|---|---|---|---|---|
| 62 | a = 0 | H | —CH$_2$— | 2,4-dimethoxy-phenyl |
| 63 | —C(O)—CH(phenyl)- | phenyl | —CH$_2$— | 2,4-dimethoxy-phenyl |
| 64 | —C(O)— | phenyl | —CH$_2$— | 2,4-dimethoxy-phenyl |
| 65 | —C(O)— | 1-biphenyl | —CH$_2$— | 2,4-dimethoxy-phenyl |
| 66 | —C(O)— | 1-naphthyl | —CH$_2$— | 2,4-dimethoxy-phenyl |
| 67 | —C(O)— | 2-naphthyl | —CH$_2$— | 2,4-dimethoxy-phenyl |
| 68 | —C(O)—N(phenyl)- | phenyl | —CH$_2$— | 2,4-dimethoxy-phenyl |
| 69 | —C(O)—CH$_2$—CH$_2$— | phenyl | —CH$_2$— | 2,4-dimethoxy-phenyl |

Representative intermediates in the synthesis of the compounds of formula (I) are as listed in Tables 5-8, below.

TABLE 5

Representative Intermediate Compounds of Formula (CI)

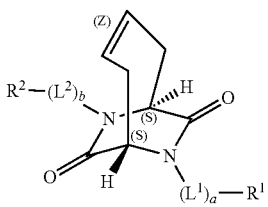

| ID No | $(L^1)_a$ | $R^1$ | $(L^2)_b$ | $R^2$ |
|---|---|---|---|---|
| 12 | a = 0 | phenyl | —CH$_2$— | 2,4-dimethoxy-phenyl |
| 13 | a = 0 | phenyl | b = 0 | H |

TABLE 5-continued

Representative Intermediate Compounds of Formula (CI)

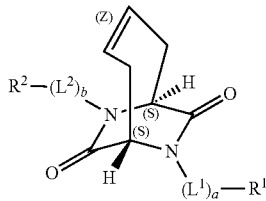

| ID No | $(L^1)_a$ | $R^1$ | $(L^2)_b$ | $R^2$ |
|---|---|---|---|---|
| 26 | a = 0 | 2-naphthyl | b = 0 | H |
| 52 | a = 0 | 6-(2,3-dihydro-benzo[1,4]dioxinyl) | —CH$_2$— | 2,4-dimethoxy-phenyl |
| 73 | —CH$_2$— | 2,4-dimethoxy-phenyl | b = 0 | H |
| 78 | a = 0 | H | b = 0 | 4-ethoxy-carbonyl-phenyl |
| 79 | —CH$_2$— | 2,4-dimethoxy-phenyl | b = 0 | 4-methoxy-phenyl |
| 80 | a = 0 | 4-methyl-phenyl | —CH$_2$— | 2,4-dimethoxy-phenyl |
| 81 | a = 0 | 2-methoxy-phenyl | —CH$_2$— | 2,4-dimethoxy-phenyl |
| 82 | —CH$_2$— | 2,4-dimethoxy-phenyl | b = o | 2-ethoxy-carbonyl-phenyl |
| 84 | a = 0 | 4-chloro-phenyl | —CH$_2$— | 2,4-dimethoxy-phenyl |
| 85 | —CH$_2$— | 2,4-dimethoxy-phenyl | b = 0 | 3-methoxy-phenyl |
| 87 | a = 0 | 4-chloro-phenyl | b = 0 | H |
| 88 | a = 0 | H | b = 0 | 3-methoxy-phenyl |
| 89 | a = 0 | 4-trifluoromethyl-phenyl | —CH$_2$— | 2,4-dimethoxy-phenyl |
| 90 | a = 0 | 4-fluoro-phenyl | —CH$_2$— | 2,4-dimethoxy-phenyl |
| 91 | a = 0 | 3-trifluoromethyl-phenyl | —CH$_2$— | 2,4-dimethoxy-phenyl |
| 92 | a = 0 | 3-trifluoromethyl-4-chloro-phenyl | —CH$_2$— | 2,4-dimethoxy-phenyl |
| 93 | a = 0 | 2-naphthyl | —CH$_2$— | 2,4-dimethoxy-phenyl |
| 94 | a = 0 | 3-chloro-phenyl | —CH$_2$— | 2,4-dimethoxy-phenyl |
| 95 | a = 0 | 3-(2-[1,3]dioxolanyl)-phenyl | —CH$_2$— | 2,4-dimethoxy-phenyl |
| 96 | a = 0 | 4-t-butyl-phenyl | —CH$_2$— | 2,4-dimethoxy-phenyl |
| 97 | a = 0 | 3-methyl-4-fluoro-phenyl | —CH$_2$— | 2,4-dimethoxy-phenyl |
| 98 | a = 0 | 2-(9H-fluorenyl) | —CH$_2$— | 2,4-dimethoxy-phenyl |
| 99 | a = 0 | 4-trifluoromethyl-phenyl | b = 0 | H |
| 100 | a = 0 | 4-fluoro-phenyl | b = 0 | H |
| 101 | a = 0 | 3-trifluoromethyl-phenyl | b = 0 | H |
| 102 | a = 0 | 3-trifluoromethyl-4-chloro-phenyl | b = 0 | H |
| 103 | a = 0 | 2-naphthyl | b = 0 | H |
| 104 | a = 0 | 3-chloro-phenyl | b = 0 | H |
| 105 | a = 0 | H | b = 0 | 4-t-butyl-phenyl |
| 106 | a = 0 | H | b = 0 | 3-methyl-4-fluoro-phenyl |
| 107 | a = 0 | 2-(9H-fluorenyl) | b = 0 | H |
| 109 | a = 0 | H | b = 0 | 4-methoxy-phenyl |
| 110 | a = 0 | 3-quinolinyl | b = 0 | H |
| 111 | a = 0 | H | b = 0 | 2-methoxy-phenyl |
| 112 | a = 0 | 2-chloro-phenyl | b = 0 | H |
| 113 | a = 0 | 5-(benzo[1,3]dioxolyl) | b = 0 | H |
| 114 | a = 0 | H | b = 0 | 3-fluoro-4-methoxy-phenyl |
| 115 | a = 0 | H | b = 0 | H |
| 116 | —CH$_2$— | 2,4-dimethoxy-phenyl | b = 0 | 2-(6-methoxy-naphthyl) |
| 117 | a = 0 | 2-biphenyl | b = 0 | H |
| 118 | a = 0 | H | b = 0 | 2-(6-methoxy-naphthyl) |
| 121 | —CH$_2$— | 2,4-dimethoxy-phenyl | —CH$_2$— | 2-naphthyl |
| 122 | —CH$_2$— | 2-naphthyl | b = 0 | H |
| 129 | a = 0 | 1-(2-[1,3]dioxolanyl-phenyl) | b = 0 | H |
| 130 | a = 0 | 3-biphenyl | —CH$_2$— | 2,4-dimethoxy-phenyl |
| 131 | a = 0 | H | —CH$_2$— | 2,4-dimethoxy-phenyl |
| 164 | a = 0 | 6-quinolinyl | —CH$_2$— | 2,4-dimethoxy-phenyl |

TABLE 6

Representative Intermediate Compounds of Formula (CI)

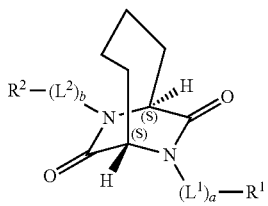

| ID No | $(L^1)_a$ | $R^1$ | $(L^2)_b$ | $R^2$ |
|---|---|---|---|---|
| 56 | a = 0 | H | —CH$_2$— | 2,4-dimethoxy-phenyl |

TABLE 7

Representative Intermediate Compounds of Formula (CII)

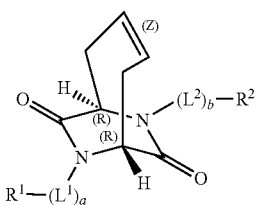

| ID No | $(L^1)_a$ | $R^1$ | $(L^2)_b$ | $R^2$ |
|---|---|---|---|---|
| 74 | —CH$_2$— | 2,4-dimethoxy-phenyl | b = 0 | H |
| 75 | a = 0 | H | b = 0 | H |
| 162 | —CH$_2$— | 2,4-dimethoxy-phenyl | b = o | 2-naphthyl |
| 163 | a = 0 | H | b = 0 | 2-naphthyl |

TABLE 8

Representative Intermediate Compounds of Formula (CII)

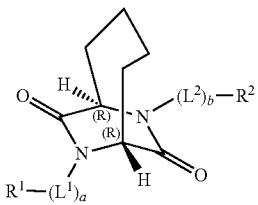

| ID No | $(L^1)_a$ | $R^1$ | $(L^2)_b$ | $R^2$ |
|---|---|---|---|---|
| 59 | a = 0 | H | b = 0 | H |
| 61 | a = 0 | H | —CH$_2$— | 2,4-dimethoxy-phenyl |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —CF$_3$, —CH$_2$—CF$_3$, —CF$_2$—CF$_2$—CF$_2$—CF$_3$, and the like.

As used herein, unless otherwise noted, the term "fluorinated $C_{1-4}$alkyl" shall mean any $C_{1-4}$alkyl group as defined above substituted with at least one fluoro atom, preferably substituted with one to three fluoro atoms. Suitable examples include but are not limited to —CF$_3$, —CH$_2$—CF$_3$, —CF$_2$—CF$_2$—CF$_2$—CF$_3$, and the like.

As used herein, the term "alkenyl" whether used alone or as part of a substituent group, include straight and branched chains comprising at least one unsaturated double bond (preferably one to two, more preferably one unsaturated double bond). For example, alkenyl radicals include —CH=CH$_2$, 2-propenyl, 3-propenyl, 2-butenyl, 3-butenyl, and the like. Unless otherwise noted, "$C_{1-4}$alkenyl" shall mean an alkenyl carbon chain composition of 1-4 carbon atoms.

As used herein, the term "alkynyl" whether used alone or as part of a substituent group, include straight and branched chains. For example, alkenyl radicals include —C≡CH, 2-propynyl, 3-propynyl, 2-butynyl, 3-butynyl, and the like. Unless otherwise noted, "$C_{1-4}$alkynyl" shall mean an alkynyl carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —OCF$_3$, —OCH$_2$—CF$_3$, —OCF$_2$—CF$_2$—CF$_2$—CF$_3$, and the like.

As used herein, unless otherwise noted, the term "fluorinated $C_{1-4}$alkoxy" shall mean any $C_{1-4}$alkoxy group as defined above substituted with at least one fluoro atom, preferably substituted with one to three fluoro atoms. Suitable examples include but are not limited to —OCF$_3$, —OCH$_2$—CF$_3$, —OCF$_2$—CF$_2$—CF$_2$—CF$_3$, and the like.

As used herein, unless otherwise noted, "aryl" shall refer to unsubstituted carbocylic aromatic groups such as phenyl, naphthyl, fluorenyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "partially unsaturated carbocyclyl" shall mean any stable five to eight membered monocyclic partially unsaturated ring structure (comprising at least one unsaturated bond); or any nine to ten membered partially unsaturated or partially aromatic bicyclic ring system. Suitable examples include, but are not limited to, cyclohexen-1-yl, 1,2,3,4-tetrahydronaphthenyl, and the like.

As used herein, unless otherwise noted, the term "carbocyclyl" shall mean any aryl or cycloalkyl group as herein defined.

As used herein, unless otherwise noted, "heteroaryl" shall denote any monocyclic, bicyclic, polycyclic or bridged aromatic ring structure containing at least one heteroatom selected from the group consisting of O, N and S, optionally containing one or more additional heteroatoms independently selected from the group consisting of O, N and S. Preferably, the heteroaryl group is a five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any monocyclic, bicyclic, polycyclic or bridged saturated, partially unsaturated or partially aromatic ring structure containing at least one heteroatom selected from the group consisting of O, N and S, optionally containing one or more additional heteroatoms independently selected from the group consisting of O, N and S. Preferably, the heterocycloalkyl group is a five to eight membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 3a,4-dihydro-3H-chromeno[4,3-c]isoxazolyl, and the like.

As used herein, unless otherwise noted, the term "heterocyclyl" shall mean heteroaryl or heterocycloalkyl group as herein defined.

As used herein, the notation "*" shall denote the presence of a stereogenic center.

When a particular group is "substituted" (e.g., alkyl, cycloalkyl, aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, $—O—SO_2$-methyl, $—O—SO_2—CF_3$, $—O—SO_2$-tolyl, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula $—C(O)O—R$ wherein R is for example methyl, ethyl, t-butyl, benzyl, phenylethyl, $CH_2=CH—CH_2—$, and the like; amides—groups of the formula $—C(O)—R^1$ wherein $R^1$ is for example methyl, phenyl, trifluoromethyl, and the like; N-sulfonyl derivatives—groups of the formula $—SO_2—R''$ wherein $R''$ is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

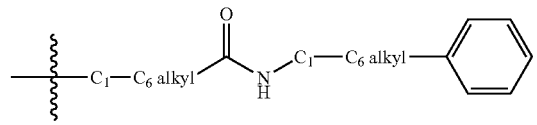

One skilled in the art will further recognize that wherein a substituent group or any part of a substituent group is listed with a "-" before and after the substituent group, such designation is intended to indicate that the substituent group is bivalent—i.e. the substituent group is bound to the rest of the compound through two bonds or points of attachment.

One skilled in the art will further recognize that for compounds of the present invention wherein "a" and/or "b" is 1 (i.e. wherein the $L^1$ and/or $L^2$ substituent group is present) then the chain length of the $L^1$ and/or $L^2$ substituent group, not counting branching, is 1 to 6 atoms. Further, in the compounds of the present invention, the combined chain length of the $L^1$ and $L^2$ substituent groups, when both are present, not counting branching, is no greater than 12 atoms and wherein only one of $L^1$ or $L^2$ is present, the chain length, not counting branching, is no greater than 6 atoms.

One skilled in the art will further understand that when counting the atoms which correspond to the length of the $L^1$ and/or $L^2$, branching and substitution atoms are not counted. For example, when the $L^1$ or $L^2$ substituent is -(1,3-(2-hydroxy)-n-propyl)-C(O)O—, this corresponds to a length of 5 atoms, as counted using the numbering system illustrated in the corresponding structure below

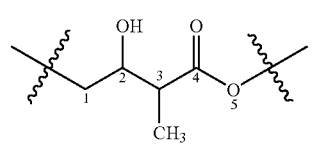 [SMILES: *CC(O)C(C)C(=O)O*]

counting the three carbon atoms of the n-propyl group, the carbon atom of the C(O) group and the oxygen atom (but not counting the hydrogen atoms on the n-propyl group, the hydroxy substituent on the n-propyl group and the oxygen of the C(O) (carbonyl) group).

One skilled in the art will further understand that wherein an $L^1$ or $L^2$ substituent group is defined such that it could theoretically have more than 6 atoms in chain length, not counting branching, then it is intended that the range of possible substituents is limited to those that will result in a chain length, not counting branching of 1 to 6 atoms.

For example, wherein $L^1$ or $L^2$ is —($C_{1-4}$alkyl)-C(O)O—($C_{1-4}$alkyl)-, one skilled in the art will understand that the —C(O)O— portion of the group contributes 2 chain atoms, and therefore the ($C_{1-4}$alkyl) group bound to the —C(O)— and the —($C_{1-4}$alkyl)- bound to the —O— are chosen such that the number of atoms which are counted towards the total chain length, not counting branching, will be no greater than 4. Thus, the following examples of pairs of alkyl groups would be allowed: (—$CH_2$— and —$CH_2$—), (—$CH_2CH_2$— and —$CH_2CH_2$—), (—$CH_2$— and —$CH_2CH_2CH_2$—), (—CH($CH_3$)— and —$CH_2CH_2$CH($CH_3$)—, ($CH_2$CH($CH_3$)— and —CH($CH_3$)$CH_2$—), and the like; whereas alkyl pairs such as (—$CH_2CH_2CH_2CH_2$— and —$CH_2$—), (—$CH_2CH_2$— and —$CH_2CH_2CH_2$—), (—$CH_2$CH($CH_3$)$CH_2$— and —CH($CH_3$)$CH_2CH_2$—) and the like, are not allowed. Note that the above lists of alkyl pairs are presented as examples only and are not intended to be fully inclusive lists of all possibilities.

Abbreviations used in the specification, particularly the Schemes and Examples, are as follows:

| | |
|---|---|
| Boc or t-Boc = | t-Buoxycarbonyl |
| DCE = | Dichloroethane |
| DCM = | Dichloromethane |
| DibAl-H = | Diisobutylamluminum hydride |
| DIPEA or DIEA = | Diisopropylethylamine |
| DMB = | Dimethoxybenzyl |
| DMF = | N,N-Dimethylformamide |
| EtOAc = | Ethyl acetate |
| HATU = | O-(7-Azabenzotriazol-1-yl)-N,N,N'',N''-Tetramethyl Uronium Hexafluorophosphate |
| HEPES = | 4-(2-Hydroxyethyl)-1-Piperizine Ethane Sulfonic Acid |
| 1H NMR = | Hydrogen Nuclear Magnetic Resonance |
| HOAt = | 1-Hydroxy-7-aza-benzotriazole |
| HOBT = | 1-Hydroxybenzotriazole |
| HPLC = | High Pressure Liquid Chromatography |
| LAH = | Lithium aluminum Hydride |
| Me = | Methyl |
| MeOH = | Methanol |
| Na(OAc)$_3$BH = | Sodium triacetoxyborohydride |
| NEM = | N-Ethylmorpholine |
| NMP = | N-methyl-2-pyrrolidinone |
| Pd-C or Pd/C = | Palladium on Carbon Catalyst |
| PMB = | p-Methoxy-benzyl |
| RedAl = | Bis(2-methoxyethoxy)aluminum hydride |
| TFA = | Trifluoroacetic Acid |
| THF = | Tetrahydrofuran |
| TLC = | Thin Layer Chromatography |
| Tris HCl or Tris-Cl = | Tris[hydroxymethyl]aminomethyl hydrochloride |

As used herein, unless otherwise noted, the terms "depression" and "depression and related disorders" shall include major depressive disorder, unipolar depression, treatment-refractory depression, resistant depression, anxious depression and dysthymia (also referred to as dysthymic disorder). Preferably, the depression is major depressive disorder, unipolar depression, treatment-refractory depression, resistant depression or anxious depression. More preferably, the depression is major depressive disorder.

As used herein, unless otherwise noted, the term "CNS disorder" shall include, depression (including major depressive disorder, childhood depression, dysthymia), manic depression (bipolar disorder), mild cognitive impairment, Alzheimer's disease, epilepsy, schizophrenia, obsessive compulsive disorder, anxiety, panic disorder, post-traumatic stress disorder, and the like. Preferably, the CNS disorder is selected from the depression, anxiety and Alzheimer's disease.

As used herein, unless otherwise noted, the term "GI-urinary disorder" shall include urinary incontinence, constipation-predominant IBS, chronic constipation, colonic inertia, idiopathic colonic pseudoobstruction and related disorders. Preferably, the GI-urinary disorder is constipation-predominant IBS.

As used herein, unless otherwise noted, the term "reproductive disorder" shall include premenstrual dysphoric disorder, vasomotor symptoms associated with menopause (i.e. hot flashes), premature ejaculation and reproductive dysfunction.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (±)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1, below.

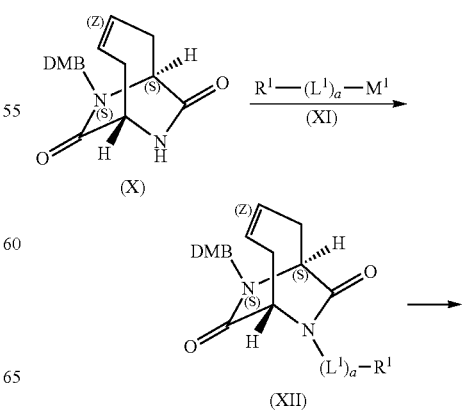

Scheme 1

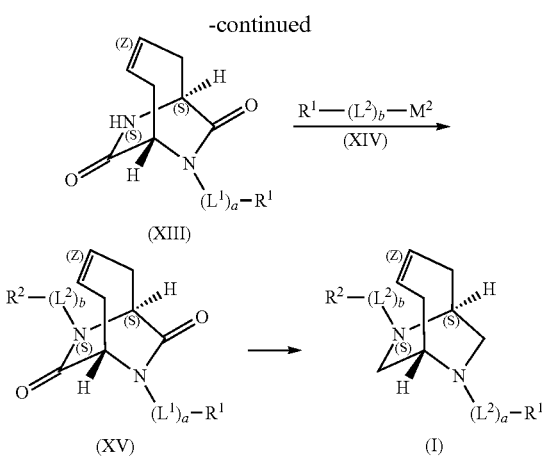

Accordingly, a suitably substituted compound of formula (X), a known compound, (prepared for example as disclosed in Du, Yanming, Creighton, Christopher J., Tounge, Brett A., Reitz, Allen B., *Organic Letters*, (2004), 6 (3), 309-312; and Creighton, Christopher J., Reitz, Allen B., *Organic Letters*, (2001), 3 (6), 893-895), is reacted with a suitably substituted compound of formula (XI), wherein $M^1$ is a suitable leaving group such as Br, Cl, I, —O—$SO_2$-methyl, —O—$SO_2$—$CF_3$, —O—$SO_2$-tolyl, and the like, a known compound or compound prepared by known methods, according to known nitrogen coupling methods, to yield the corresponding compound of formula (XII).

The compound of formula (XII) is de-protected according to known methods, to yield the corresponding compound of formula (XIII).

The compound of formula (XIII) is reacted with a suitably substituted compound of formula (XIV), wherein $M^1$ is a suitable leaving group such as Br, Cl, I, —O—$SO_2$-methyl, —O—$SO_2$—$CF_3$, —O—$SO_2$-tolyl, and the like, a known compound or compound prepared by known methods, according to known nitrogen coupling methods, to yield the corresponding compound of formula (XV).

The compound of formula (XV) is reduced according to known methods, for example, by reacting with a suitably selected reducing agent such as DIBAL-H, LAH, RedAl, and the like, in an organic solvent such as THF, diethyl ether, glyme, toluene, and the like, at a temperature in the range of from about 50° C. to about 200° C., preferably at about 120° C., to yield the corresponding compound of formula (I).

One skilled in the art will recognize that protecting groups other than DMB may be used in the process outlined in Scheme 1, for example benzyl, PMB, and the like.

One skilled in the art will further recognize that compounds of formula (II) may be similarly prepared according to the process outlined in Scheme 1 above, by selecting and substituting a suitably substituted compound of formula (XX)

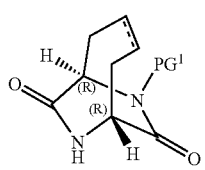

(XX)

a known compound, prepared by known methods, wherein $PG^1$ is a suitable protecting group such as DBM, and the like, for the compound of formula (X).

Compounds of formula (I) and compounds of formula (II) wherein ≈ is a single bond may be prepared from the corresponding compounds of formula (I) and (II) wherein ≈ is a double bond by reducing the suitably substituted and protected (as necessary and/or desirable) compounds of formula (I) and compounds of formula (II) wherein ≈ is a double bond, according to known methods, for example by reacting with hydrogen gas in the presence of a catalyst such as Pd/C, Pt, Rh, Ni, or other transition metal known to facilitate reduction of unsaturated systems, in an organic solvent such as ethanol, ethyl acetate, isopropyl alcohol, and the like.

The present invention further comprises pharmaceutical compositions containing one or more compounds of formula (I) and/or formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating of the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders as defined herein is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day or any range therein. Preferably, the range is from about 0.1 to about 50 mg/kg of body weight per day, more preferably, from about 0.1 to about 25.0 mg/kg of body weight per day, more preferably, from about 0.1 to about 10.0 mg/kg of body weight per day more preferably, from about 0.1 to about 5.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

7-(2,4-Dimethoxybenzyl)-7,9-diaza-bicyclo[4.4.2]dec-3-ene-8,10-dione

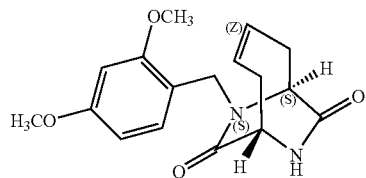

STEP A: N-2,4-Dimethoxybenzyl allylglycine methyl ester

A suspension of allyglycine (15 grams, 130 mmol) in methanol (260 mL) was cooled with an ice bath to 0° C. and thionyl chloride (14.26 mL, 195 mmol) was added drop wise via an addition funnel. Once all the thionyl chloride was added the ice bath was removed and the reaction was allowed to proceed overnight. The next morning the solvent was removed under reduced pressure. The resulting oil was triturated for 4 hours in an ethyl ether-ethyl acetate mixture (approx. 95-5). The resulting allylglycine methyl ester hydrochloride was collected on a glass fritted funnel. The allylglycine methyl ester hydrochloride (9.5 g, 57.54 mmol) was placed into separatory funnel and treated with excess 10% $Na_2CO_3$ in water. The free base was extracted from the aqueous layer with ethyl ether. The organics were dried with anhydrous magnesium sulfate and the ethyl ether was removed under reduced pressure. Care must be taken to remove only ether, because the allylglycine methyl ester is somewhat volatile under reduced pressure. Once the ethyl ether was removed the compound was weighed (7.27 g, 56.32 mmol) and dissolved in 1,2-dichloroethane (200 mL). An equimolar amount of 2,4-dimethoxybenzaldehyde was added (9.36 g, 56.32 mmol) followed by addition of sodium triacetoxyborohydride (16.71 g, 78.85 mmol). The reaction was allowed to proceed for 12 hrs. Excess borohydride was quenched with 10% $Na_2CO_3$ in water and the DCE removed under reduced pressure. Ethyl ether was added to the reaction mixture and the organic and aqueous layers were poured into a separatory funnel. The ethyl ether layer was washed 3× with 10% $Na_2CO_3$ in water and then dried with anhydrous magnesium sulfate. The diethyl ether was removed under reduced pressure to yield a clear yellow oil. The oil was purified using flash chromatography (65:35 hexanes:ethyl acetate) to yield a clear, colorless, oil.

$^1$H NMR, free base: ($CDCl_3$ δ) 7.1 (d, 1H, J=8.6 Hz); 6.4 (m, 2H); 5.7 (m, 1H); 5.1 (m, 2H); 3.5-3.9 (m, 10H); 2.4 (m, 2H); 2.0 (1H, broad)

STEP B: Boc-Allyglycine-N-(2,4-dimethoxybenzyl) allylglycine methylester

N-2,4-dimethoxybenzyl allylglycine methyl ester (as the free base) (7.79 g, 27.9 mmol) was dissolved in methylene chloride (90 mL), and then Boc-allyglycine-OH (6.0 g, 27.9 mmol), HOAt (3.8 g, 27.9 mmol), HATU (10.6 g, 27.9 mmol) and N-ethyl morpholine (3.6 mL, 27.9 mmol) were added to the reaction mixture. The reaction was allowed to proceed for 12 hours at room temperature after which time the solvent was removed and the crude mixture was dissolved/suspended in diethyl ether. The crude reaction was filtered through a pad of Celite® to remove solid byproducts. The Celite® was washed 3× with diethyl ether after which the combined ether solutions were poured into a separatory funnel and washed three times with 10% $Na_2CO_3$ in water, one time with saturated brine solution, three times with 1 N HCl and one time saturated brine. The organic layer was dried with anhydrous magnesium sulfate and the solvent was removed under reduced pressure. Final purification was accomplished by flash chromatography (3:1 hexanes/ethyl acetate) to yield a clear, colorless oil.

$^1$H NMR (300 Hz, $CDCl_3$, δ) 7.12, (d, 1H, 9 Hz); 6.45, (m, 2H); 5.7, (m, 1H), 5.35 (d, 1H, 9 Hz); 5.0, (m, 5H); 4.65, (d, 1H, 15 Hz); 4.35, (d, 1H, 15 Hz); 4.05, (m, 1H); 3.75, (m, 6H); 3.55, (s, 3H), 2.7, (m, 1H); 2.55 (m, 2H); 2.35 (m, 1H); 1.5 (s, 9H)

HPLC Rt=3.95

MS m/z (% relative intensity, ion): 477 (30, M+H$^+$), 499 (30, M+Na$^+$) 151 (100, M+ of DMB)

STEP C: (2S,7S)-7-N-(t-Butyloxycarbonyl)amino-1-(2,4-dimethoxybenzyl)-8-oxo-1,2,3,6,7-pentahydroazocine-2-carboxylic acid methyl ester Boc-Allyglycine-N-2,4-dimethoxybenzyl-allylglycine methylester 3 (3.0 g, 6.25 mmol) was dissolved in methylene chloride (200 mL) and added to a 5-L round-bottom flask equipped with a condenser. Additional methylene chloride (1800 mL) was added to the reaction followed by the addition of Grubbs catalyst—benzylidene bis(tricyclohexylphosphine)dichlororuthenium (0.514 g, 0.625 mmol). The reaction mixture was heated to reflux for 60 hr under a stream of dry nitrogen. The solvent was then removed by rotary evaporator, and the crude product was purified by flash chromatography (3:1 hexanes/ethyl acetate) to provide yield a clear, light brown oil.

¹H NMR (300 Hz, CDCl₃, δ) 7.09 (d, 1H, J=8 Hz); 6.40 (m, 2H); 6.20 (d, 1H, J=5 Hz); 5.72 (m, 1H); 5.45 (m, 1H); 4.95 (m, 2H); 4.60 (d, 1H, J=15 Hz); 4.28 (d, 1H, J=15 Hz); 3.80 (s, 3H); 3.80 (s, 3H); 3.44 (s, 3H); 3.00 (m, 1H); 2.70 (m, 2H); 2.35 (ddd, 1H, J=16, 8, 3 Hz); 1.45 (s, 9H)

HPLC Rt=4.06 min

MS m/z (% relative intensity, ion)]: 449 (20, M+H⁺), 471 (20, M+Na⁺) 151 (100, M+ of DMB)

Elemental Analysis for $C_{23}H_{32}N_2O_7$:
Calculated: C, 61.59; H, 7.19; N, 6.25.
Found: C, 61.82; H, 7.20; N, 5.96.

STEP D: 7-(2,4-dimethoxybenzyl)-7,9-diaza-bicyclo[4.4.2]dec-3-ene-8,10-dione (2S,7S)-7-N-(t-Butyloxycarbonyl)amino-1-(2,4-dimethoxybenzyl)-8-oxo-1,2,3,6,7-pentahydroazocine-2-carboxylic acid methyl ester (1.0 g) was treated in a 96% formic acid solution (15 ml) for one hour at room temperature. The solvent was removed under reduced pressure at room temperature and the resulting residue was dissolved in solution of sec-butanol (16 ml) and toluene (5 ml). The resulting mixture was heated to reflux for 48 h after which time the solvent was removed and the residue purified on silica gel using a gradient method from ethyl acetate (100%) to a mixture of ethyl acetate/MeOH (8:2) to yield the title compound as a residue.

¹H NMR (300 Hz, CDCl₃, δ) 7.63 (d, J=3.4 Hz, 1H), 7.22-7.16 (m, 1H), 6.47-6.41 (m, 2H), 5.36-5.19 (m, 2H), 4.89 (d, J=14.4 Hz, 1H) 4.19 (d, J=14.3 Hz, 1H), 4.09 (td, J=4.3, 3.4 Hz 1H), 4.00 (t, J=3.8 Hz, 1H), 3.80 (s, 3H), 3.79 (s, 3H), 3.04-2.60 (m, 4H).

Example 2

Z-(1S,6S)-7-naphthalen-2-yl-7,9-diaza-bicyclo[4.2.2]dec-3-ene

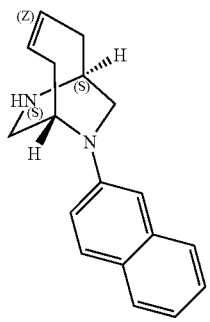

STEP A: Z-(1S,6S)-7-(2,4-Dimethoxy-benzyl)-9-naphthalen-2-yl-7,9-diaza-bicyclo[4.2.2]dec-3-ene-8,10-dione 7-(2,4-Dimethoxybenzyl)-7,9-diaza-bicyclo[4.4.2]dec-3-ene-8,10-dione (0.50 g, 1.58 mmol), 2-bromonaphthalene (0.327 g, 1.58 mmol), CuI (0.015 g, 0.158 mmol) and powdered potassium carbonate (0.437 g, 3.16 mmol) were added to a CEM microwave 10-mL pressure-rated tube. A rubber septa was attached to the tube and the reaction mixture was purged of oxygen using argon and vacuum purges. Dioxane (5 mL) followed by N,N'-demethylethylenediamine (0.017 mL, 0.158 mmol) were then added to the reaction mixture. The septa was removed, the vessel was capped with the appropriate CEM system cap and the reaction mixture was heated in a CEM discover system laboratory microwave at 230° C. for 1 hour. The reaction mixture was poured into a 100 mL round bottom flask and Celite® (approximately 5 g) and ethyl acetate (20 mL) were added. The solvents were removed. The Celite®/reaction mixture was loaded into an Isco solid phase loading cartridge. Flash chromatography was carried out using an Isco companion automated chromatography system, silica column (40 g), gradient 20% ethyl acetate in heptane to 85% over 15 column volumes, holding at 85% ethyl acetate for 5 more column volumes to yield a residue.

¹H NMR (300 Hz, CDCl₃, δ)

STEP B: Z-(1S,6S)-7-naphthalen-2-yl-7,9-diaza-bicyclo[4.2.2]dec-3-ene-8,10-dione Z-(1S,6S)-7-(2,4-Dimethoxy-benzyl)-9-naphthalen-2-yl-7,9-diaza-bicyclo[4.2.2]dec-3-ene-8,10-dione (0.180, 0.406 mmol) was placed in a CEM microwave 10-mL pressure-rated tube and was dissolved in trifluoroacetic acid (4.25 mL) and thioanisol (0.05 mL). The reaction mixture was capped and heated in a CEM discover system laboratory microwave at 120° C. for 0.5 hours. The reaction mixture was poured into a 100 mL round bottom flask and Celite® (approximately 5 g) and ethyl acetate (20 mL) were added. The solvents were removed. The Celite®/reaction mixture was loaded into an Isco solid phase loading cartridge. Flash chromatography was carried out using an Isco Companion automated chromatography system, silica column (12 g), initially holding at 40% ethyl acetate in heptane for 8 column volumes, increasing the ethylacetate concentration to 100% over 3 column volumes, holding at 100% ethyl acetate for 20 more column volumes to yield a residue.

STEP C: Z-(1S,6S)-7-naphthalen-2-yl-7,9-diaza-bicyclo[4.2.2]dec-3-ene

Z-(1S,6S)-7-naphthalen-2-yl-7,9-diaza-bicyclo[4.2.2]dec-3-ene-8,10-dione (0.8 g, 2.74 mmol) was dissolved in a solution of Dibal (THF, 1 M, 28 mL). The reaction was carried out in a large scale CEM microwave reaction vessel. The reaction mixture was heated to 120° C. for 0.5 h and then allowed to cool to room temperature. A one-liter Erlenmeyer flask was charged with diethyl ether (400 mL) and the reaction mixture was poured into the diethyl ether. A water solution of saturated Rochelle salts was added dropwise until gas stopped evolving and then water saturated with Rochelle salts (approximately 200 mL) was poured into the reaction mixture. The resulting mixture was stirred at room temperature until both phases were clear. The reaction mixture then was poured into a separatory funnel and the aqueous layer was discarded. The diethyl ether was dried with anhydrous magnesium sulfate and the solvent was removed using reduced pressure to yield a clear colorless oil.

¹H NMR (300 Hz, CDCl₃, δ) 7.75-7.6 (m, 3H), 7.35 (t, 1H), 7.18 (t, 1H), 7.05 (dd, 1H), 6.85 (s, 1H), 5.6 (m, 1H), 5.45 (m, 1H), 3.95 (bs, 1H), 3.8 (bs, 1H), 3.75 (dd, 1H), 3.6-3.4 (m, 2H), 3.1 (dd, 1H), 3.05-2.9 (m, 1H), 2.3-2.65 (m, 3H)

HPLC Rt=2.93 min

MS m/z [API-ES] 265.2 (M+H⁺).

Example 3

7-(9H-Fluoren-2-yl)-7,9-diaza-bicyclo[4.2.2]dec-3-ene

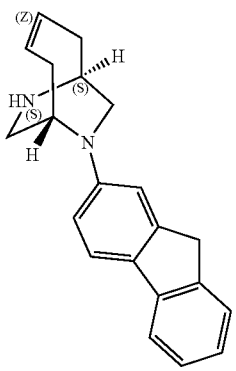

7-(9H-Fluoren-2-yl)-7,9-diaza-bicyclo[4.2.2]dec-3-ene-8,10-dione (310 mg, 0.94 mmol) in THF (4 mL) was placed in a μW tube. Dibal-H (4 mL, 4 mmol, [1M] in THF) was then added to the reaction mixture with venting under argon flow. When all H$_2$ evolution was completed, the reaction mixture was heated to 130° C. for 900 sec. The reaction mixture was then diluted with a saturated Rochelle's solution (30 mL) and diethyl ether (30 mL) followed by stirring vigorously overnight. The layers were separated and the organic solution was dried with magnesium sulfate, filtered and the solvent removed by reduced pressure to yield the title compound as a residue.

$^1$H NMR (300 Hz, CDCl$_3$, δ) 7.65 (m, 2H), 7.45 (d, 1H), 7.35 (m, 2H), 7.15 (d, 1H), 6.85 (s, 1H), 6.7 (d, 1H), 5.7 (m, 1H), 5.5 (m, 1H), 3.4-3.85 (m, 6H), 2.8-3.05 (m, 2H), 2.2-2.75 (m, 4H), 1.8 (bs, 1H)

HPLC Rt=3.393 min.
MS m/z [API-ES] 303.0 (M+H$^+$).

Example 4

Z-(1R,6R)-7-naphthalen-2-yl-7,9-diaza-bicyclo[4.2.2]dec-3-ene

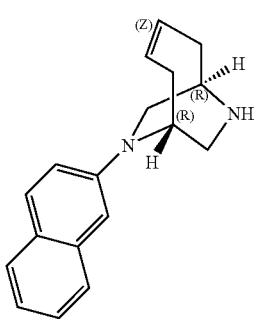

7-Naphthalen-2-yl-7,9-diaza-bicyclo[4.2.2]dec-3-ene-8,10-dione (130 mg, 0.45 mmol) and DiBAl-H (6 mL, 1M, 6 mmol) were placed in a μW tube under argon vent. The reaction mixture was then heated to 130° C. for 900 sec. The reaction was quenched with Rochelle's salt and diethyl ether mixture (1:1, 200 mL) and then stirred overnight. The organic eas layer separated and dried with magnesium sulfate, filtered and solvent evaporated under reduced pressure to yield the title compound as a residue.

$^1$H NMR (400 Hz, CDCl$_3$, δ) 7.5-7.8 (m, 3H), 7.25 (t, 1H), 7.1 (t, 1H), 6.98 (d, 1H), 6.75 (s, 1H), 5.5 (m, 1H), 5.3 (m, 1H), 3.8 (bs, 1H) 3.7 (bs, 1H), 3.6 (m, 1H), 3.4 (d, 1H), 3.3 (d, 1H), 2.9 (d, 1H), 2.8 (m, 1H), 2.4 (m, 1H), 2.1-2.3 (m, 3H)

HPLC Rt=2.77 min.
MS m/z [ES+] 265.15 (M+H$^+$).

Example 5

Z-(1S,6S)-7-naphthalen-2-ylmethyl-7,9-diaza-bicyclo[4.2.2]dec-3-ene

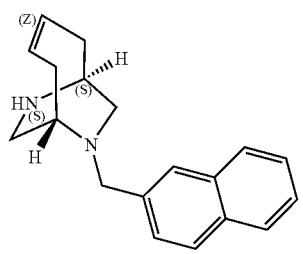

Z-(1S,6S)-7-naphthalen-2-ylmethyl-7,9-diaza-bicyclo[4.2.2]dec-3-ene-8,10-dione (40 mg, 0.1307 mmol) was placed in a μW tube, followed by addition of DiBAl-H (3 mL, 3 mmol, [1M] in THF). The reaction mixture was purged under argon for 20 min, then heated to 130° C. for 900 sec. The reaction mixture was poured in to a 100 mL mixture (1:1) of Rochelle's solution and diethyl ether and stirred vigorously overnight. The reaction mixture was separated and the organic layer was dried with magnesium sulfate, filtered and the solvent evaporated under reduced pressure to yield an oil. The oil was treated with 1M HCl in diethyl ether (2 mL) to yield the title compound as a residue.

$^1$H NMR (300 Hz, CDCl$_3$, δ) 7.8 (m, 4H) 7.55 (d, 1H), 7.48 (m, 2H), 5.6 (m, 1H), 5.45 (m, 1H), 3.85-4.0 (q, 2H), 3.35-3.5 (m, 3H), 3.1 (m, 1H), 3.0 (m, 1H), 2.8 (d, 1H) 2.4-2.6 (m, 4H), 2.0 (m, 1H)

HPLC Rt=2.457 min.
MS m/z [API-ES] 279.0 (H+).

Example 6-23

Additional compounds of the present invention were similarly prepared according to the procedure as described in Example 1 above, by substituting a suitably substituted aryl bromide for the 2-bromonaphthalene reagent. Table E1 below lists the suitably selected aryl bromide, the final product and measured mass for the compounds prepared in Examples 6-23

TABLE E1

Examples 6-23 Reagents and Products

| Example # | Aryl bromide Reagent | Product Name | MS m/z (M + H$^+$) |
|---|---|---|---|
| 6 | 4-methyl bromobenzene | (Z)-(1S,6S)-7-(p-tolyl)-7,9-diaza-bicyclo[4.2.2]dec-3-ene | 229 |

TABLE E1-continued

Examples 6-23 Reagents and Products

| Example # | Aryl bromide Reagent | Product Name | MS m/z (M + H+) |
|---|---|---|---|
| 7 | 4-fluoro bromobenzene | (Z)-(1S,6S)-7-(4-fluorophenyl)-7,9-diaza-bicyclo[4.2.2]dec-3-ene | 233 |
| 8 | 3-trifluoromethyl bromobenzene | (Z)-(1S,6S)-7-(3-trifluoromethylphenyl)-7,9-diaza-bicyclo[4.2.2]dec-3-ene | 283 |
| 9 | 4-chloror-3-trifluoromethyl bromobenzene | (Z)-(1S,6S)-7-(4-chloro-3-trifluoromethylphenyl)-7,9-diaza-bicyclo[4.2.2]dec-3-ene | 317 |
| 10 | 4-tertbutyl bromobenzene | (Z)-(1S,6S)-7-(4-tertbutylphenyl)-7,9-diaza-bicyclo[4.2.2]dec-3-ene | 271 |
| 11 | 3-methyl-4-fluoro-bromobenzene | (Z)-(1S,6S)-7-(3-methyl-4-fluoro)-7,9-diaza-bicyclo[4.2.2]dec-3-ene | 247 |
| 12 | 3-bromobiphenyl | (Z)-(1S,6S)-7-(biphenyl-3-yl)-7,9-diaza-bicyclo[4.2.2]dec-3-ene | 291 |
| 13 | 2-bromochloro-benzene | (Z)-(1S,6S)-7-(2-chlorophenyl)-7,9-diaza-bicyclo[4.2.2]dec-3-ene | 249 |
| 14 | 3-bromoanisole | (Z)-(1S,6S)-7-(3-methoxyphenyl)-7,9-diaza-bicyclo[4.2.2]dec-3-ene | 245 |
| 15 | 2-bromoanisole | (Z)-(1S,6S)-7-(2-methoxyphenyl)-7,9-diaza-bicyclo[4.2.2]dec-3-ene | 245 |
| 16 | bromobenzene | (Z)-(1S,6S)-7-(phenyl)-7,9-diaza-bicyclo[4.2.2]dec-3-ene | 215 |
| 17 | 3-bromoquinoline | (Z)-(1S,6S)-7-quinolin-3-yl-7,9-diaza-bicyclo[4.2.2]dec-3-ene | 266 |
| 18 | 4-bromoanisole | (Z)-(1S,6S)-7-(4-methoxyphenyl)-7,9-diaza-bicyclo[4.2.2]dec-3-ene | 245 |
| 19 | 2-bromo-6-methoxy-naphthylene | (Z)-(1S,6S)-7-(4-methoxy-naphthalene-2-yl)-7,9-diaza-bicyclo[4.2.2]dec-3-ene | 295 |
| 20 | 3-bromochloro-benzene | (Z)-(1S,6S)-7-(3-chlorophenyl)-7,9-diaza-bicyclo[4.2.2]dec-3-ene | 249 |
| 21 | 1-bromo-3,4-dichlorobenzene | (Z)-(1S,6S)-7-(3,4-dichlorophenyl)-7,9-diaza-bicyclo[4.2.2]dec-3-ene | 284 |
| 22 | 6-bromo-2,3-dihydro-1,4-benzodioxane | (Z)-(1S,6S)-7-(2,3-dihydro-benzo[1,4]dioxin-6-yl)-7,9-diaza-bicyclo[4.2.2]dec-3-ene | 273 |
| 23 | 5-bromoquinoline | (Z)-(1S,6S)-7-(4a,8a-dihydro-quinolin-5-yl)-7,9-diaza-bicyclo[4.2.2]dec-3-ene | 266 |

Examples 24-38

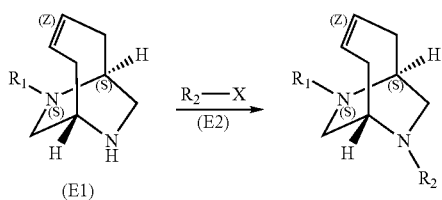

Additional compounds of the present invention were prepared by according to the scheme above. More specifically, a suitably substituted compound of formula (E1) was reacted with a suitably substituted compound of formula (E2) wherein X is a suitable leaving group, to yield the corresponding compound of the present invention. Table E2 below lists the $R^1$ and $R^2$ substituent groups and final product measured mass for the compounds prepared in Examples 24-38.

TABLE E2

Examples 24-38 Product Substient Groups

| Example # | $R^1$ | $R^2$ | MS m/z (M + H+) |
|---|---|---|---|
| 24 | naphth-2-yl | Methyl-1,4-benzodioxanyl | 413 |
| 25 | naphth-2-yl | Ethyl-1,2,3,4-tetrahydroquinazolinyl-2,4-dione | 453 |
| 26 | naphth-2-yl | propargyl | 303 |
| 27 | 6-methoxy-naphth-2-yl | 2,4-dimethoxybenzyl | 445 |
| 28 | 3-biphen-3-yl | 2,4-dimethoxybenzyl | 441 |
| 29 | 6-methoxy-naphth-2-yl | methyl | 309 |
| 30 | 3-biphen-3-yl | methyl | 305 |
| 31 | 6-methoxy-naphth-2-yl | 4-fluoroethylphenyl | 417 |
| 32 | 3-biphen-3-yl | 4-fluoroethylphenyl | 413 |
| 33 | naphth-2-yl | Ethyl-pyridin-2-yl-amino | 385 |
| 34 | naphth-2-yl | methyl-2,3-dihydro-7H-[1,4]dioxino[2,3-e]indolyl | 452 |
| 35 | naphth-2-yl | 1-benzo[b]thiophen-3-yl-propan-1-one | 453 |
| 36 | naphth-2-yl | 1-benzo[b]thiophen-3-yl-propan-1-ol | 455 |
| 37 | naphth-2-yl | Methyl-8-methyl-naphthyl | 419 |
| 38 | naphth-2-yl | methylcyclooctane | 389 |

Example 39

4-Oxiranylmethoxy-1-H-indole

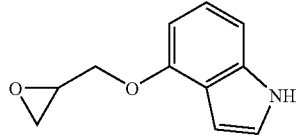 [SMILES: c1cc(OCC2CO2)c2cc[nH]c2c1]

4-hydroxy indole (0.08 g, mmol) was dissolved in dimethylformamide (1.5 mL). Sodium hydride (0.02 g, 0.51 mmol) was slowly added to the reaction mixture followed by addition of (R)-glycidyl 3-nitrobenzene sulfonate (0.132, 0.51 mmol). A red color appeared. After 3 hour the reaction mixture was poured into a separatory funnel and ethyl acetate (100 mL) was added. The organic layer was washed 3 times with a 10% solution of sodium carbonate in water. The aqueous layers were discarded, the organic layer was dried with sodium sulfate and the solvent was removed by reduced pressure to yield crude product. The crude product was dissolved in ethyl acetate, Celite® (approximately 3 grams) was added, followed by removal of the solvent under reduced pressure. The Celite®/reaction mixture was loaded into an Isco solid phase loading cartridge. Flash chromatography was carried out using an Isco Companion automated chromatography system, silica column (4 g), initially holding at 5% ethyl acetate in heptane for 3 column volumes, increasing the ethyl acetate concentration to 60% over 40 column volumes, holding at 60% ethyl acetate for 10 more column volumes to yield the title compound as a residue.

$^1$H NMR (300 Hz, CDCl$_3$, δ) 8.17 (bs, 1H), 7.12-7.03 (m, 3H), 6.69 (d, J=2.3 Hz, 1H), 5.52 (d, 7.3 Hz, 1H), 4.35 (dd, J=3 Hz, 11 Hz, 1H), 4.15 (dd, J=5 Hz, 11 Hz, 1H), 3.45 (m, 1H), 2.93 (t, J=5 Hz, 1H), 2.81 (dd, J=3 Hz, 5 Hz, 1H)

HPLC Rt=3.13 min.

MS m/z [API-ES] 190.1 (M+H+).

Example 40

(S)-1-Methyl-4-oxiranylmethoxy-1H-indole

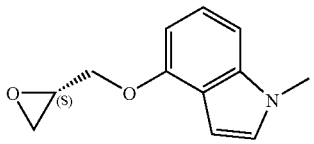

1-Methyl-4-methoxy-1H-indole (0.5 g, 3.1 mmol) was dissolved in dichloromethane (20 mL) and cooled to 0° C. A solution of BBr$_3$ (3.1 mL, 3.1 mmol, 1M in CH$_2$Cl$_2$) was added slowly and the reaction mixture was stirred for 3 hours. Ice chips were added to quench the reaction. 0.1 N NaOH was then added to the reaction mixture, followed by extraction of the reaction mixture with eth acetate (200 mL) to yield crude product. The crude product was dried overnight under high vacuum. The crude product was dissolved in DMF (30 mL) and allowed to stir at room temperature under argon atmosphere. NaH (135 mg, 3.38 mmol, 60% in oil) was added and the reaction mixture was stirred for 20 min. (S)-3-glycidyl nitrobenzene sulfonate (0.875 g, 3.38 mmol) was added and the resulting mixture was stirred overnight at room temperature under an argon atmosphere. The reaction was quenched with a 10% solution of sodium carbonate in water and extracted with ethyl acetate. The organic layer was dried with sodium sulfate, filtered and the solvent evaporated under reduced pressure to yield crude product which was purified by flash chromatography (120 g silica, 20% Ethyl acetate/heptane) to yield the title compound as a residue.

$^1$H NMR (400 Hz, CDCl$_3$, δ) 7.15 (t, 1H), 7.0 (m, 2H), 6.6 (s, 1H), 6.5 (d, 1H), 4.3 (d, 1H), 4.13-4.18 (dd, J=5 Hz, 11 Hz, 1H), 3.77 (s, 3H), 3.44 (m, 1H), 2.9 (d, J=5 Hz, 1H), 2.8 (d, J=5 Hz, 1H)

HPLC Rt=3.570 min.
MS m/z [API-ES] 204.1 (M+H$^+$).

Example 41

(S)-2-Methyl-5-oxiranylmethoxy-pyridine

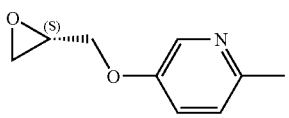

6-Methyl-pyridin-3-ol (0.218 g, 2.0 mmol) was placed in a flask with DMF (10 mL) and NaH (60% dispersion in oil, 77 mg, 2.0 mmol) and stirred for 30 min. at room temperature. (S)-glycidyl 3-nitrobenzene sulfonate (0.52 g, 2.0 mmol) was then added to the reaction mixture, which was then stirred at room temperature for 14 hours. The reaction was quenched with NaHCO$_3$ (saturated) and then extracted three times with ethyl acetate. The organic layer was dried with magnesium sulfate, filtered and the solvent was evaporated under reduced pressure to yield crude product which was purified by silica gel chromatography (60% Ethyl acetate/heptane) to yield the title compound as a residue.

$^1$H NMR (400 Hz, CDCl$_3$, δ) 8.21 (s, 1H), 7.15 (dd, J=3 Hz, 8 Hz, 1H), 7.06 (d, J=8 Hz, 1H), 4.27 (dd, J=3 Hz, 11 Hz, 1H) 3.96 (dd, J=5 Hz, 11 Hz, 1H), 3.35 (m, 1H), 2.92 (t, J=4 Hz, 1H), 2.765 (dd, J=3, 4 Hz, 1H), 2.49 (s, 3H).

Example 42

(S)-4-Oxiranylmethoxy-9H-carbazole

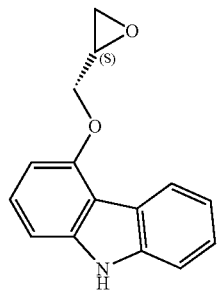

9H-Carbazol-4-ol (0.367 g, 2.0 mmol) was placed in a flask with DMF (10 mL) and NaH (60% dispersion in oil, 77 mg, 2.0 mmol) and stirred for 30 min at room temperature. (S)-glycidyl 3-nitrobenzene sulfonate (0.52 g, 2.0 mmol) was added to the reaction mixture, which was then stirred at room temperature for 14 hours. The reaction was quenched with NaHCO$_3$ (saturated) and then extracted with ethyl acetate (3×). The organic layer was dried with magnesium sulfate, filtered and the solvent evaporated under reduced pressure to yield crude product which was purified by silica gel chromatography (60% Ethyl acetate/heptane) to yield the title compound as a residue.

$^1$H NMR (400 Hz, CD$_3$OD, δ) 8.3 (d, J=7 Hz, 1H), 8.05 (bs, 1H), 7.40 (d, J=4 Hz, 1H), 7.39 (m, 1H), 7.33-7.26 (t, J=8 Hz, 1H) 7.23-7.25 (m, 1H), 7.06 (d, J=8 Hz, 1H), 6.65 (d, J=8 Hz, 1H), 4.45-4.47 (dd, J=3 Hz, 11 Hz, 1H), 4.24-4.28 (dd, J=5 Hz, 11 Hz, 1H), 3.5 (m, 1H), 2.98-3.0 (dd, J=4, 9 Hz, 1H), 2.88-2.90 (dd, J=2 Hz, 5 Hz, 1H)).

Example 43

(S)-2-Methyl-4-oxiranylmethoxy-1H-indole

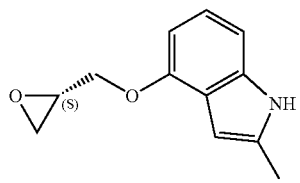

2-Methyl-1H-indol-4-ol (0.58 g, 3.9 mmol) and THF (20 mL) were placed in a round bottom flask and stirred at room temperature. Sodium bis(trimethylsilyl) amide (3.9 mL, [1M] in THF) was then slowly added to the reaction mixture. After fifteen minutes of stirring at room temperature (R)-glycidyl-3-nitrobenzenesulfonate was added and the reaction mixture was allowed to stir overnight. Work up of the reaction mixture was carried out with saturated sodium carbonate solution and ethyl acetate. The organic layer was dried with sodium sulfate, filtered and the solvent was removed under reduced pressure to yield a crude oil. The crude oil was purified by flash chromatography (20% Ethyl acetate/heptane) to yield the title compound as a crystalline solid.

¹H NMR (400 Hz, CDCl₃, δ) 7.9 (bs, 1H), 6.95-7.1 (q, J=2, 6 Hz, 2H), 6.5 (d, 1H), 6.3 (s, 1H), 4.35 (d, 1H), 4.15 (m, 1H), 4.2 (m, 1H), 2.95 (m, 1H), 2.8 (m, 1H), 2.4 (s, 3H)

HPLC Rt=3.529 min.

MS m/z [API-ES] 204.1 (M+H⁺).

Example 44

(R)-1-(1-Indol-4-yloxy)-3-(Z)-(1S,6S)-9-naphthalen-2-yl-7,9-diaza-bicyclo[4.2.2]dec-3-en-7-yl)-propan-2-ol

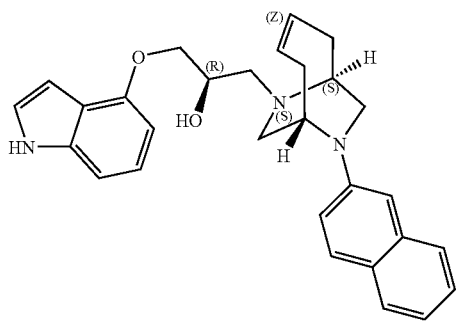

(R)-4-Oxiranylmethoxy-1-H-indole (50 mg, 0.26 mmol) and Z-(1S,6S)-7-naphthalen-2-yl-7,9-diaza-bicyclo[4.2.2]dec-3-ene (50 mg, 0.189 mmol) were placed in a μW tube with ethanol (3 ml), ethyl acetate (1 mL) and heated to 105° C. for 900 sec. The solvent was removed and the crude oil was purified via reverse phase chromatography (20% CH₃CN to 90% CH₃CN in water). The solvents were removed under reduced pressure to yield the title compound as a residue.

¹H NMR (400 Hz, CD₃OD, δ) 7.8-7.8 (m, 3H), 7.35 (t, 1H), 7.25 (t, 1H), 6.95-7.20 (m, 6H), 6.55 (s, 1H), 6.5 (s, 1H), 5.90 (m, 1H), 5.75 (m, 1H), 4.65 (m, 1H), 4.5 (m, 1H), 4.4 (m, 1H), 4.15-4.3 (m, 2H), 4.0 (m, 2H), 3.85 (m, 1H), 3.4 (m, 1H), 3.3 (m, 1H), 3.1 (m, 2H), m, 2.7 (m, 2H)

HPLC Rt=3.06 min.

MS m/z [API-ES] 453.9 (M+H⁺).

Example 45

(S)-1-(6-Methyl-pyridin-3-yloxy)-3-(-(Z)-(1S,6S)-9-naphthalen-2-yl-7,9-diaza-bicyclo[4.2.2]dec-3-en-7-yl)-propan-2-ol

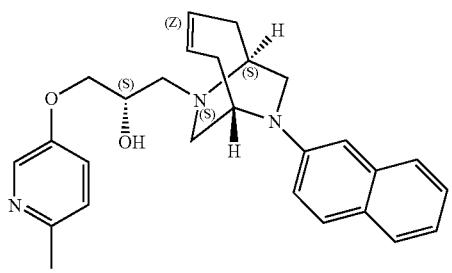

(S)-2-Methyl-5-oxiranylmethoxy-pyridine (13 mg, 0.077 mmol) and Z-(1S,6S)-7-naphthalen-2-yl-7,9-diaza-bicyclo[4.2.2]dec-3-ene (20 mg, 0.189 mmol) were placed in a μW tube with ethanol (3 ml), DIPEA (15 μL, 0.086 mmol) and heated to 95° C. for 900 sec. The solvent was removed and the residue was purified via silica chromatography (30% Ethyl acetate/heptane) to yield the title compound as a residue.

¹H NMR (300 Hz, CDCl₃, δ) 8.24 (d, J=3 Hz, 1H), 7.5-7.7 (m, 3H), 7.35 (t, 1H), 7.08-7.2 (m, 4H), 6.83 (d, J=2 Hz, 1H), 5.48 (m, 2H), 4.2 (m, 1H), 3.7-4.0 (m, 2H), 3.5 (m, 2H), 3.3 (bs, 1H), 2.9-3.1 (m, 4H), 2.55-2.8 (m, 4H), 2.5 (s, 3H), 2.3 (m, 2H)

HPLC R$_t$=2.505 min.

MS m/z [API-ES] 429.9 (M+H⁺).

Example 46

(S)-1-(9H-Carbazol-4-yloxy)-3-((Z)-9-naphthalen-2-yl-7,9-diaza-bicyclo[4.2.2]dec-3-en-7-yl)-propan-2-ol

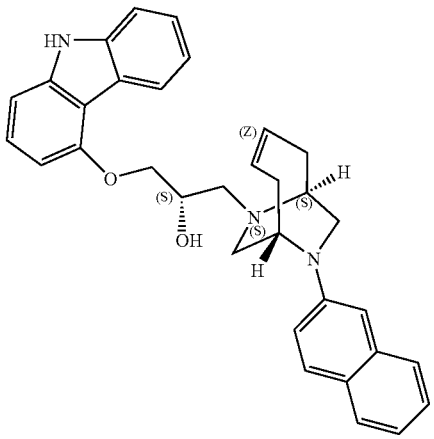

(S)-4-Oxiranylmethoxy-9H-carbazole (18.5 mg, 0.077 mmol) and Z-(1S,6S)-7-naphthalen-2-yl-7,9-diaza-bicyclo[4.2.2]dec-3-ene (20 mg, 0.189 mmol) were placed in a μW tube with ethanol (3 ml), DIPEA (15 μL, 0.086 mmol) and heated to 95° C. for 900 sec. The solvent was evaporated and the residue was purified via silica chromatography (30% Ethyl acetate/heptane) to yield the title compound as a residue.

¹H NMR (400 Hz, CDCl₃, δ) 8.30 (d, J=8 Hz, 1H), 8.07 (bs, 1H), 7.6-7.7 (m, 3H), 7.0-7.5 (m, 8H), 6.84 (s, 1H), 6.72 (d, J=8 Hz, 1H), 5.5 (m, 2H), 4.0 (m, 2H), 4.28 (m, 2H), 4.12 (m, 1H), 3.90 (m, 1H), 3.72 (m, 1H), 3.5 (m, 2H), 3.3 (bs, 1H) 3.11-3.15 (dd, J=3 Hz, 12 Hz, 1H), 2.8-3.03 (m, 2H), 2.55-2.68 (m, 2H), 2.3 (d, J=18 Hz, 1H)

HPLC Rt=3.612 min.

MS m/z [API-ES] 503.9 (M+H⁺).

Example 47

(S)-1-(1-Methyl-1H-indol-4-yloxy)-3-(9-naphthalen-2-yl-7,9-diaza-bicyclo[4.2.2]dec-3-en-7-yl)-propan-2-ol

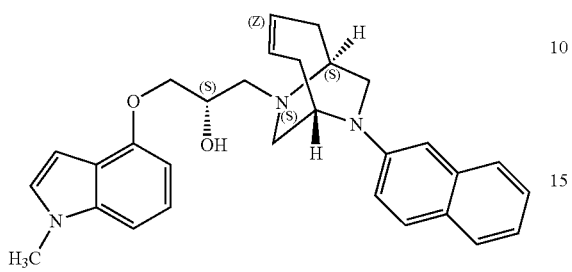

(S)-1-Methyl-4-oxiranylmethoxy-1H-indole (50 mg, 0.25 mmol) and Z-(1S,6S)-7-naphthalen-2-yl-7,9-diaza-bicyclo[4.2.2]dec-3-ene (50 mg, 0.189 mmol) were placed in a μW tube with ethanol (2 ml), DIPEA (100 μL, 0.576 mmol) and heated to 120° C. for 900 sec. The solvent was evaporated from the reaction mixture and the residue was purified via flash chromatography (gradient 30% to 100% ethyl acetate/heptane) to yield the title compound as a residue.

$^1$H NMR (300 Hz, CDCl$_3$, δ) 7.7 (m, 3H), 7.3 (t, 1H), 7.15 (m, 2H), 7.05 (d, 1H), 7.0 (m, 2H), 6.8 (s, 1H), 6.55 (m, 2H), 5.5 (m, 2H), 4.0-4.3 (m, 3H), 3.9 (m, 1H), 3.8 (s, 3H), 3.5 (t, 2H), 3.3 (bs, 1H), 3.0 (m, 4H) 2.8 (m, 1H), 2.6 (m, 2H), 2.2.3 (d, 1H), 1.5-1.8 (bs, 1H)

HPLC Rt=3.990 min.

MS m/z [API-ES] 469.2, 468.2 (M+H$^+$).

Example 48

(S)-1-(7-Chloro-quinolin-4-yloxy)-3-[9-(9H-fluoren-2-yl)-7,9-diaza-bicyclo[4.2.2]dec-3-en-7-yl]-propan-2-ol

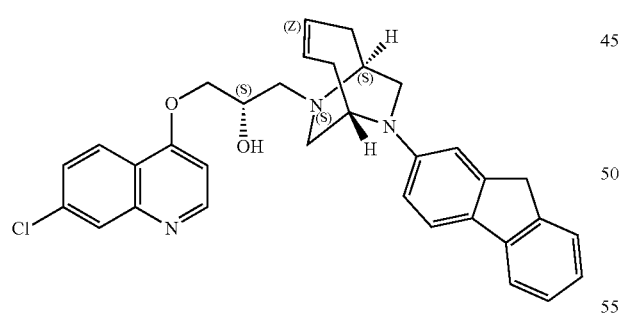

(S)-7-Chloro-4-oxiranylmethoxy-quinoline (20 mg, 0.084 mmol) and Z-(1S,6S)-7-(9H-fluoren-2-yl)-7,9-diaza-bicyclo[4.2.2]dec-3-ene (22 mg, 0.073 mmol) were placed in a μW tube with ethanol (3 ml), DIPEA (15 μL, 0.086 mmol) and heated to 95° C. for 900 sec. The solvent was evaporated from the reaction mixture and the residue was purified via reverse phase chromatography (gradient 20% to 90% CH$_3$CN/water for 12 min) to yield the title compound as a residue.

$^1$H NMR (300 Hz, CD$_3$OD, δ) 9 (d, 1H), 8.55 (d, 1H), 8.1 (s, 1H), 7.6-7.8 (m, 3H), 7.4-7.55 (m, 2H), 7.3 (t, 1H), 7.1-7.2 (m, 2H), 6.9 (m, 1H), 5.9 (m, 1H), 5.6-5.7 (m, 1H), 4.7 (m, 1H), 4.6 (m, 2H), 4.4 (m, 2H), 3.7-4.05 (m, 4H) 3.4-3.6 (m, 2H), 3.0 (m, 2H), 2.6-2.9 (m, 4H)

HPLC Rt=3.367 min.

MS m/z [API-ES] 540.8, 537.9 (M+H$^+$).

Example 49

5-[2-Hydroxy-3-(9-naphthalen-2-yl-7,9-diaza-bicyclo[4.2.2]dec-3-en-7-yl)-propoxy]-3,4-dihydro-1H-quinolin-2-one

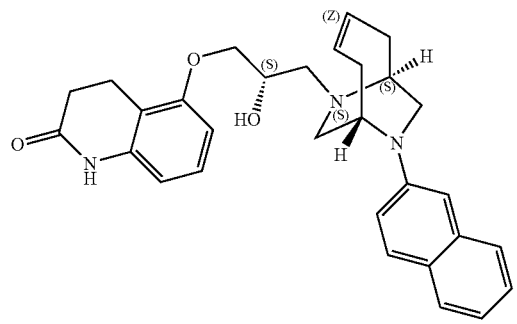

(S)-5-Oxiranylmethoxy-3,4-dihydro-1H-quinolin-2-one (25 mg, 0.114 mmol) and Z-(1S,6S)-7-naphthalen-2-yl-7,9-diaza-bicyclo[4.2.2]dec-3-ene (30 mg, 0.114 mmol) were placed in a μW tube with ethanol (2 ml), CH$_2$Cl$_2$ (2 mL), DIPEA (100 μL, 0.576 mmol) and heated to 95° C. for 900 sec. The solvent was evaporated from the reaction mixture and the residue was purified via flash chromatography (gradient 10% to 100% Ethyl acetate/heptane) to yield the title compound as a residue.

$^1$H NMR (300 Hz, CDCl$_3$, δ) 7.55-7.75 (m, 4H) 7.3 (t, 1H), 7.0-7.25 (m, 3H), 6.85 (s, 1H), 6.6 (m, 1H), 6.4 (d, 1H), 5.5 (m, 2H), 4.0-4.1 (m, 2H), 3.9 (m, 1H), 3.5 (m, 2H), 3.3 (m, 2H), 3.0 (m, 6H) 2.7 (m, 1H), 2.6 (m, 4H), 2.3 (m, 1H), 1.6 (bs, 1H)

HPLC Rt=2.832 min.

MS m/z [API-ES] 485.0, 483.9 (H+).

Example 50

1-(9H-Carbazol-4-yloxy)-3-(9-naphthalen-2-yl-7,9-diaza-bicyclo[4.2.2]dec-3-en-7-yl)-propan-2-ol

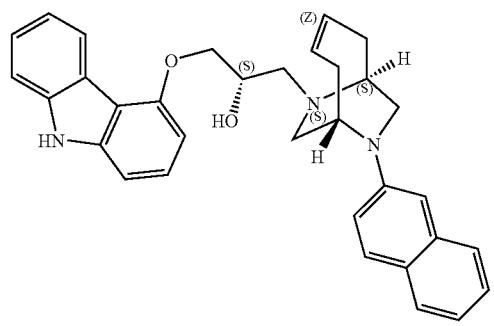

(S)-4-Oxiranylmethoxy-9H-carbazole (18.5 mg, 0.077 mmol) and Z-(1S,6S)-7-naphthalen-2-yl-7,9-diaza-bicyclo

[4.2.2]dec-3-ene (20 mg, 0.189 mmol) were placed in a μW tube with ethanol (3 ml), DIPEA (15 μL, 0.086 mmol) and heated to 95° C. for 900 sec. The solvent was evaporated from the reaction mixture and the residue was purified via silica chromatography (30% Ethyl acetate/heptane) to yield the title compound as a residue.

¹H NMR (400 Hz, CDCl₃, δ) 8.30 (d, J=8 Hz, 1H), 8.07 (bs, 1H), 7.6-7.7 (m, 3H), 7.0-7.5 (m, 8H), 6.84 (s, 1H), 6.72 (d, J=8 Hz, 1H), 5.5 (m, 2H), 4.0 (m, 2H), 4.28 (m, 2H), 4.12 (m, 1H), 3.90 (m, 1H), 3.72 (m, 1H), 3.5 (m, 2H), 3.3 (bs, 1H) 3.11-3.15 (dd, J=3 Hz, 12 Hz, 1H), 2.8-3.03 (m, 2H), 2.55-2.68 (m, 2H), 2.3 (d, J=18 Hz, 1H)

HPLC Rt=3.612 min.

MS m/z [API-ES] 503.9 (M+H⁺).

Example 51

1-(7-Chloro-2-methyl-1H-indol-4-yloxy)-3-(9-naphthalen-2-yl-7,9diazabicyclo[4.2.2]dec-3-en-7-yl)-propan-2-ol

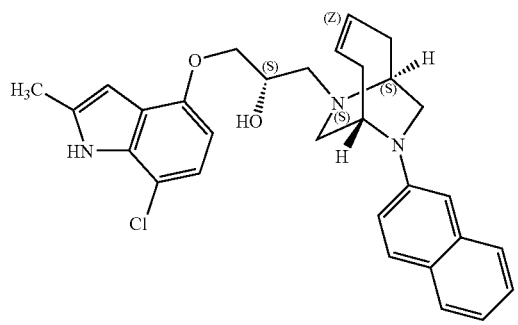

4-Oxiranylmethoxy-1H-indole (10 mg, 0.04 mmol) and Z-(1S,6S)-7-naphthalen-2-yl-7,9-diaza-bicyclo[4.2.2]dec-3-ene (15 mg, 0.06 mmol) were placed in a μW tube with ethanol (2 ml), DIPEA (100 μL, 0.57 mmol) and heated to 120° C. for 900 sec. The solvent was evaporated to yield an oil which was purified via silica chromatography (gradient 0% Ethyl acetate/heptane to 100% Ethyl acetate/heptane) to yield the title compound as a residue.

¹H NMR (400 Hz, CDCl₃, δ) 8.0 (bs, 1H), 7.7 (m, 3H), 7.3 (t, 1H), 7.1 (t, 1H), 6.9 (m, 2H), 6.8 (s, 1H), 6.4 (d, 1H), 6.3 (s, 1H), 5.4 (m, 2H), 4.2 (m, 1H), 4.0 (m, 2H), 3.8 (d, 1H), 3.45 (m, 2H), 3.3 (bs, 1H), 2.9-3.0 (m, 4H), 2.7 (m, 1H), 2.42-2.6 (m, 2H), 2.4 (s, 3H), 2.2 (m, 2H)

HPLC Rt=3.918 min. MS m/z [API-ES] 502.2 (M+H⁺).

Example 52

1-[9-(9H-Fluoren-2-yl)-7,9-diaza-bicyclo[4.2.2]dec-3-en-7-yl]-3-(1H-indol-4-yloxy)-propan-2-ol

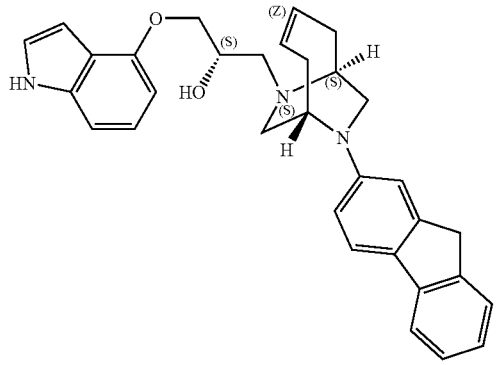

4-Oxiranylmethoxy-1H-indole (20 mg, 0.07 mmol) and Z-(1S,6S)-7-naphthalen-2-yl-7,9-diaza-bicyclo[4.2.2]dec-3-ene (19.2 mg, 0.063 mmol) were placed in a μW tube with ethanol (3 ml), DIPEA (15 μL, 0.086 mmol) and heated to 95° C. for 900 sec. The solvent was evaporated from the reaction mixture to yield an oil which was purified via silica chromatography (30% Ethyl acetate/heptane) to yield the title compound as a residue.

¹H NMR (400 Hz, CDCl₃, δ) 8.2 (s, 1H), 7.6 (m, 2H), 7.4 (d, 1H), 7.3 (m, 1H), 7.2-7.0 (m, 3H), 6.85 (s, 1H), 6.7 (m, 2H), 6.6 (d, 1H), 5.5 (m, 2H), 4.3 (m, 1H), 4.15 (m, 3H), 3.8-4.0 (m, 4H), 3.7 (bs, 1H), 3.35-3.45 (m, 2H) 3.3 (s, 1H), 2.9-3.1 (m, 2H), 2.8 (m, 1H), 2.5-2.7 (m, 2H), 2.3 (d, 1H)

HPLC Rt=3.653 min.

MS m/z [API-ES] 492.0 (M+H⁺).

Example 53

1-(1-Indol-4-yloxy)-3-((E)-9-naphthalen-2-yl-7,9-diaza-bicyclo[4.2.2]dec-3-en-7-yl)-propan-2-ol

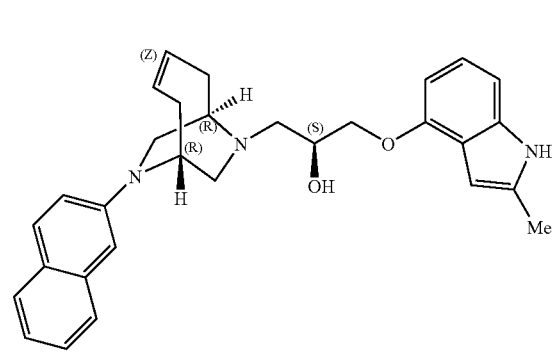

7-Naphthalen-2-yl-7,9-diaza-bicyclo[4.2.2]dec-3-ene (130 mg, 0.49 mmol) and oxirane (99 mg, 0.49 mmol) were placed in a μW tube with ethanol (3 ml), and DiPEA (0.1 mL, 0.57 mmol) and heated to 130° C. for 900 sec. The solvent was evaporated to yield a crude oil, which was purified via flash chromatography (40 g, gradient 10% to 100% Ethyl acetate/heptane) to yield the title compound as a residue.

¹H NMR (400 Hz, CDCl₃, δ) 7.8 (bs, 1H), 7.5-7.7 (m, 3H), 7.25 (t, 1H), 7.10 (t, 1H), 6.9 (m, 2H), 6.85 (d, 1H), 6.72 (s, 1H), 6.45 (d, 1H) 6.25 (s, 1H), 5.90 (m, 2H), 4.2 (m, 1H), 3.9-4.04 (m, 3H), 3.8 (m, 1H), 3.4 (d, 1H), 3.25 (bs, 1H), 3.2 (d, 1H), 3.05 (d, 1H), 2.9-3.0 (m, 2H), 2.7 (m, 1H), 2.5 (d, 1H), 2.4 (d, 1H), 2.3 (s, 3H), 2.1 (d, 1H)

HPLC Rt=3.07 min.

MS m/z [API-ES] 468.3 (M+H⁺).

Example 54

1-[9-(2,3-Dihydro-benzo[1,4]dioxin-6-yl)-7,9-diaza-bicyclo[4.2.2]dec-3-en-7-yl]-3-(1H-indol-4-yloxy)-propan-2-ol

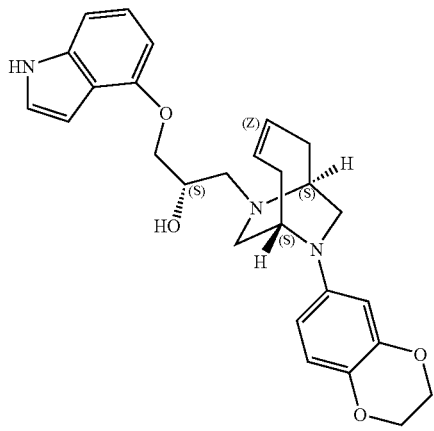

7-(2,3-Dihydro-benzo[1,4]dioxin-6-yl)-7,9-diaza-bicyclo[4.2.2]dec-3-ene (15 mg, 0.055 mmol) and 4-oxiranylmethoxy-1H-indole (20 mg, 0.106 mmol) were placed in a μW tube with ethanol (2 ml), DiPEA (0.2 mL) and heated to 120° C. for 900 sec. The solvent was evaporated to yield a crude oil, which was purified via reverse phase chromatography (20% CH₃CN to 90% CH₃CN in water) to yield the title compound as a residue.

¹H NMR (400 Hz, CD₃OD, δ) 7.15 (bs, 1H), 7.0 (m, 2H), 6.75 (d, 1H), 6.5 (m, 3H), 6.35 (s, 2H), 5.90 (m, 1H), 5.75 (m, 1H), 4.5 (m, 1H), 4.3 (m, 1H), 4.1-4.2 (m, 5H), 3.8-4.0 (m, 2H), 3.5 (m, 2H), 3.3 (bs, 1H), 3.1 (m, 1H), 2.9 (m, 1H), 2.7 (m, 1H), 2.55 (m, 1H)

HPLC Rt=2.709 min.

MS m/z [API-ES] 461.9 (M+H⁺).

Example 55

1-(2-Methyl-1H-indol-4-yloxy)-3-(9-naphthalen-2-yl-7,9-diaza-bicyclo[4.2.2]dec-3-en-7-yl)-propan-2-ol

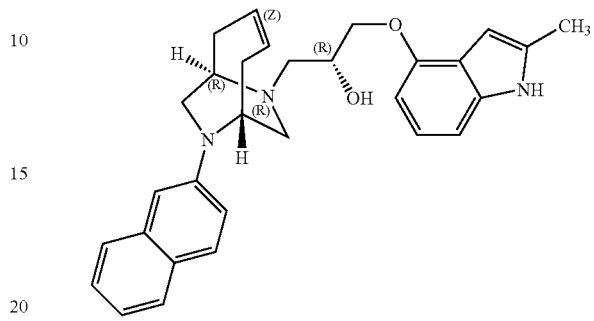

Z-(1S,6S)-7-naphthalen-2-yl-7,9-diaza-R,R-bicyclo[4.2.2]dec-3-ene (60 mg g, 0.228 mmol), R-2-methyl-4-oxiranylmethoxy-1H-indole (48 mg, 0.228 mmol), DIPEA (0.1 mL) and ethanol (3 mL) were placed in a μW tube and μW at 130° C. for 900 sec. The solvent was evaporated under reduced pressure to yield a crude oil, which was purified via flash silica chromatography (50% Ethyl acetate/heptane) to yield the title compound as a crystalline solid.

¹H NMR (400 Hz, CDCl₃, δ) 7.8 (bs, 1H), 7.5-7.65 (m, 3H), 7.28 (t, 1H), 7.1 (t, 1H), 6.9 (m, 2H), 6.85 (d, 1H), 6.7 (s, 1H), 6.5 (d, 1H), 6.3 (s, 1H), 5.4 (m, 2H), 4.2 (m, 1H), 4.1 (m, 2H), 4.0 (bs, 1H), 3.8 (m, 1H), 3.5 (m, 1H), 3.4 (m, 2H), 3.3 (bs, 1H), 2.95 (m, 2H), 2.75 (m, 1H), 2.5 (m, 2H), 2.35 (s, 3H), 2.2 (m, 1H), 1.5 (bs, 1H)

HPLC Rt=3.816 min.

MS m/z [API-ES] 468.3 (M+H⁺).

Example 56

1-(1H-Indol-4-yloxy)-3-(9-naphthalen-2-ylmethyl-7,9-diaza-bicyclo[4.2.2]dec-3-en-7-yl)-propan-2-ol

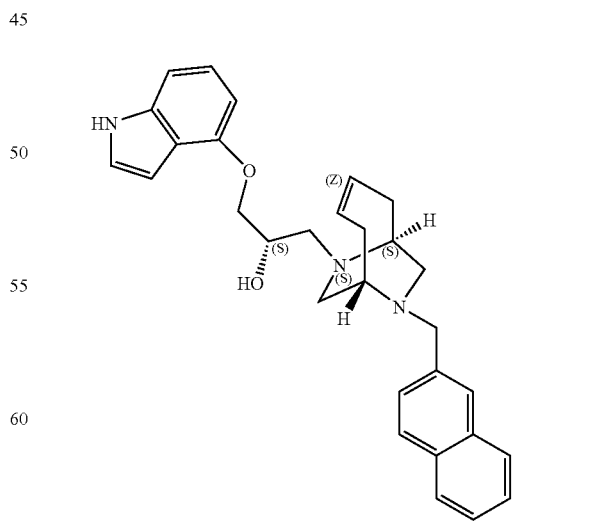

Z-(1S,6S)-7-naphthalen-2-ylmethyl-7,9-diaza-bicyclo[4.2.2]dec-3-ene (30 mg, 0.064 mmol), ethyl acetate (0.5 mL)

and 4-oxiranylmethoxy-1H-indole (50 mg, 0.26 mmol) were placed in a μW tube with ethanol (3 ml) and heated to 95° C. for 900 sec. The solvent was evaporated to yield a crude oil, which was purified via flash chromatography (15% Ethyl acetate/heptane to 100% Ethyl acetate) to yield the title compound as a residue.

$^1$H NMR (300 Hz, CDCl$_3$, δ) 8.1 (bs, 1H), 7.7 (m, 3H), 7.5 (m, 4H), 7.1 (m, 3H), 6.6 (s, 1H), 6.55 (d, 1H), 6.0 (m, 1H), 5.5 (m, 2H), 4.3 (m, 1H), 4.1 (m, 2H), 3.9 (m, 2H), 3.7 (m, 1H), 3.5 (m, 1H), 3.3 (m, 1H), 3.1 (m, 2H), 2.9 (m, 1H), 2.2-2.7 (m, 3H), 2.0 (m, 1H)

HPLC Rt=3.080 min.

MS m/z [API-ES] 468.9 (M+H$^+$).

Example 57

Z-(1S,6S)-7-(2,4-Dimethoxy-benzyl)-9-naphthalen-2-yl-7,9-diaza-bicyclo[4.2.2]dec-3-ene

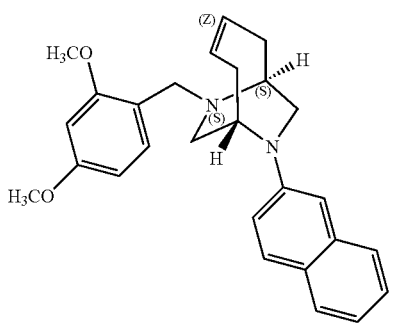

Z-(1S,6S)-7-(2,4-Dimethoxy-benzyl)-9-naphthalen-2-yl-7,9-diaza-bicyclo[4.2.2]dec-3-ene-8,10-dione (102 mg, 0.023 mmol), THF (1 mL) and DiBAl-H (6 mL, 6 mmol, [1M]) were placed in a μW tube under argon vent then heated to 130° C. for 900 sec. The reaction was quenched with Rochelle's solution and diethyl ether and the resulting mixture stirred overnight. The organic layer was separated and dried with magnesium sulfate, filtered and the solvent evaporated under reduced pressure to yield a crude oil, which was purified via reverse chromatography (20% CH$_3$CN/water to 100% water) to yield the title compound as a residue.

$^1$H NMR (300 Hz, CD$_3$OD, δ) 7.78 (d, 1H), 7.7 (m, 2H), 7.38 (m, 2H), 7.23 (m, 2H), 7.03 (s, 1H), 6.68 (s, 1H), 6.6 (m, 1H), 5.88 (m, 1H), 5.58 (m, 1H), 4.86 (s, 6H), 4.48 (s, 2H), 4.28 (m, 1H), 4.13 (m, 1H), 3.93 (s, 2H), 3.78 (m, 6H)

HPLC Rt=3.294 min.

MS m/z [API-ES] 414.9 (M+H$^+$).

Example 58

1-Benzo[b]thiophen-3-yl-3-(9-naphthalen-2-yl-7,9-diaza-bicyclo[4.2.2]dec-3-en-7-yl)-propan-1-one

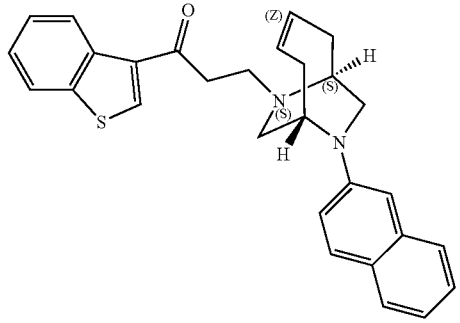

Z-(1S,6S)-7-naphthalen-2-yl-7,9-diaza-bicyclo[4.2.2]dec-3-ene (50 mg, 0.189 mmol), 1-benzo[b]thiophen-3-yl-3-chloro-propan-1-one (50 mg, 0.22 mmol) and DiPEA (0.1 mL, 0.57 mmol) were placed in a μW tube with NMP (2 ml), and heated to 160° C. for 900 sec. The solvent was evaporated to yield a crude oil, which was purified via reverse phase chromatography (20% CH$_3$CN to 90% CH$_3$CN in water) to yield a residue which was then treated with 1N HCl in diethyl ether. The solvent was then evaporated under reduced pressure to yield the title compound as its corresponding HCl salt, as a residue.

$^1$H NMR (400 Hz, CD$_3$OD, δ) 8.9 (s, 1H), 8.7 (d, 1H), 7.9 (m, 1H), 7.8 (d, 1H), 7.7 (m, 2H), 7.5 (m, 2H), 7.4 (t, 1H), 7.2 (m, 2H), 7.05 (s, 1H), 5.85 (m, 1H), 5.65 (m, 1H), 4.35 (m, 2H), 3.9 (m, 1H), 3.6-3.9 (m, 7H), 3.1 (m, 7H), 2.7 (m, 2H)

HPLC Rt=3.375 min.

MS m/z [API-ES] 452.9 (M+H$^+$).

Example 59

1-Benzo[b]thiophen-3-yl-3-(9-naphthalen-2-yl-7,9-diaza-bicyclo[4.2.2]dec-3-en-7-yl)-propan-1-ol

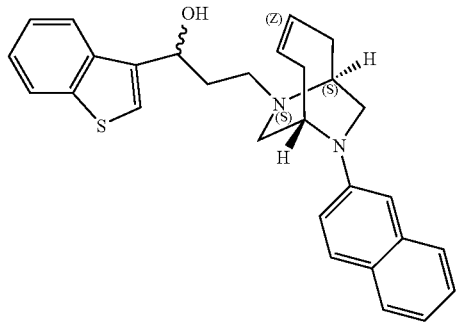

1-Benzo[b]thiophen-3-yl-3-(9-naphthalen-2-yl-7,9-diaza-bicyclo[4.2.2]dec-3-en-7-yl)-propan-1-one (8 mg, 0.0176 mmol), sodium borohydride (20 mg, 0.5 mmol) and methanol (1 ml), were placed in a round bottom flask and the reaction mixture stirred for one hour at room temperature. To the reaction mixture were then added a solution of 1N NaOH (10 mL) and ethyl acetate (10 mL). The resulting mixture was separated and the organic layer was dried with magnesium sulfate, filtered and evaporated under reduced pressure to yield the title compound as a solid.

¹H NMR (300 Hz, CDCl₃, δ) 7.5-8.0 (m, 4H), 7.1-7.45 (m, 5H), 7.05 (d, 1H), 6.8 (s, 1H), 5.55 (m, 2H), 5.4 (m, 1H), 4.1 (m, 1H), 3.8 (m, 1H), 2.8-3.5 (m, 5H), 2.55 (d, 1H), 1.9-2.3 (m, 3H)

HPLC Rt=3.258 min.
MS m/z [API-ES] 455.8 (M+H⁺).

Example 60

4-[3-Hydroxy-4-(9-naphthalen-2-yl-7,9-diaza-S,S-bicyclo[4.2.2]dec-3-en-7-yl)-butyl]-1H-indole-2-carboxylic acid methyl ester

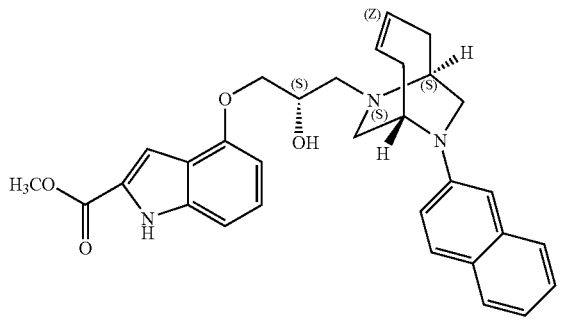

4-(2-Oxiranyl-ethyl)-1H-indole-2-carboxylic acid methyl ester (24 mg, 0.097 mmol), Z-(1S,6S)-7-naphthalen-2-yl-7,9-diaza-bicyclo[4.2.2]dec-3-ene (36 mg, 0.136 mmol), ethanol (2 mL), dichloromethane (2 mL) were heated to 105° C. for 900 seconds in a μW reaction tube. The solvent was evaporated under reduced pressure to yield a crude solid which was purified by reverse phase chromatography gradient [20% CH₃CN/H₂O to 100% CH₃CN] to yield the title compound as a residue.

¹H NMR (300 Hz, CD₃OD) δ 7.8 (d, 1H), 7.7 (m, 1H), 7.4 (m, 1H), 7.2 (m, 5H), 7.1 (m, 2H), 5.9 (m, 1H), 5.6 (m, 1H), 4.6 (m, 1H), 3.95 (m, 1H), 3.85 (m, 1H), 4.2 (m, 2H), 3.25-4.0 (m, 9H), 3.5 (m, 1H), 3.1 (m, 2H), 2.7 (m, 2H)

HPLC Rt=3.368 min.
MS m/z [API-ES] 512.3 (M+H⁺).

Example 61

4-[3-Hydroxy-4-(9-naphthalen-2-yl-7,9-diaza-S,S-bicyclo[4.2.2]dec-3-en-7-yl)-butyl]-7-chloro-1H-indole-2-carboxylic acid methyl ester

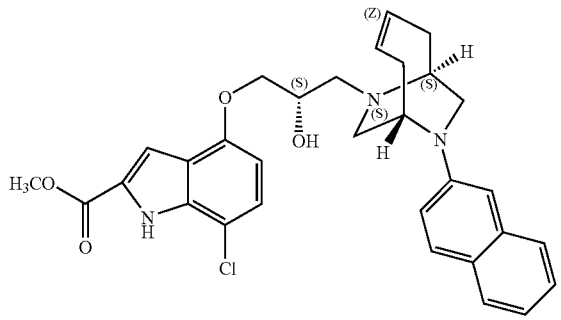

7-Chloro-4-(2-oxiranyl-ethyl)-1H-indole-2-carboxylic acid methyl ester (50 mg, 1.9 mmol), Z-(1S,6S)-7-naphthalen-2-yl-7,9-diaza-bicyclo[4.2.2]dec-3-ene (50 mg, 1.9 mmol), DIPEA (0.15 mL, 0.85 mmol), ethanol (3 mL), dichloromethane (2 mL) were heated for 900 sec. at 120° C. in a μW reaction tube. The solvent was evaporated under reduced pressure to yield a crude solid that was purified by reverse phase chromatography gradient [20% CH₃CN/H₂O to 100% CH₃CN] to yield the title compound as a residue.

¹H NMR (400 Hz, CD₃OD) δ 7.8 (d, 1H), 7.7 (m, 2H), 7.4 (m, 2H), 7.3 (m, 4H), 7.1 (bs, 1H), 6.6 (d, 1H), 6.0 (m, 1H), 5.8 (m, 1H), 4.6 (bs, 1H), 4.5 (m, 1H), 4.35 (m, 1H), 4.25 (m, 2H), 3.8-4.1 (m, 5H), 3.5 (m, 1H), 3.1 (m, 2H), 2.8 (m, 2H)

HPLC Rt=3.396 min.
MS m/z [API-ES] 546.2 (M+H⁺).

Example 62

4-(2-Methyl-1H-indol-4-yl)-1-(9-quinolin-5-yl-7,9-diaza-S,S-bicyclo[4.2.2]dec-3-en-7-yl)-butan-2-ol

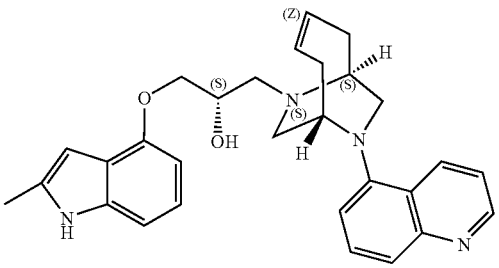

2-Methyl-4-(2-oxiranyl-ethyl)-1H-indole (24 mg, 0.118 mmol), 7-quinolin-5-yl-7,9-diaza-bicyclo[4.2.2]dec-3-ene (31 mg, 0.118 mmol), DIPEA (0.1 mL, 0.57 mmol), ethanol (2 mL) were heated for 900 sec. at 120° C. in a μW reaction tube. The solvent was evaporated under reduced pressure to yield a crude solid that was purified by reverse phase chromatography gradient [20% CH₃CN/H₂O to 100% CH₃CN] to yield the title compound as a residue.

¹H NMR (400 Hz, CD₃OD) δ 9.1 (m, 2H), 7.8-8.05 (m, 4H), 7.6 (m, 1H), 6.8 (m, 3H), 6.5 (bs, 1H), 6.6 (d, 1H), 5.7 (m, 2H), 4.6 (m, 1H), 4.4 (m, 2H), 4.2 (m, 3H), 4.0 (m, 1H), 3.4-3.8 (m, 6H), 3.1 (m, 2H), 2.4 (m, 1H), 2.25 (s, 3H)

HPLC Rt=2.031 min.
MS m/z [API-ES] 469.2 (M+H⁺).

Example 63

1-[9-(3,4-Dichloro-phenyl)-7,9-diaza-S,S-bicyclo[4.2.2]dec-3-en-7-yl]-4-(2-methyl-1H-indol-4-yl)-butan-2-ol

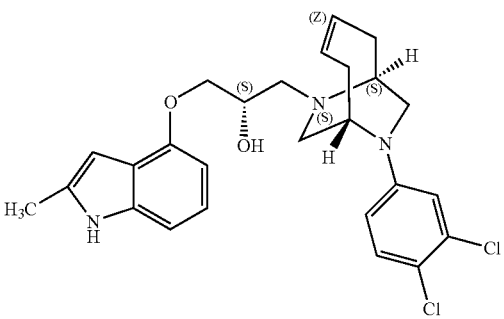

2-Methyl-4-(2-oxiranyl-ethyl)-1H-indole (40 mg, 0.196 mmol), 7-(3,4-dichloro-phenyl)-7,9-diaza-bicyclo[4.2.2]dec-3-ene (28 mg, 0.1 mmol), DIPEA (0.1 mL, 0.57 mmol), ethanol (2 mL), dichloromethane (0.5 mL) were heated for 900 sec. at 120° C. in a μW reaction tube. The solvent was evaporated under reduced pressure to yield a crude solid that was purified by reverse phase chromatography gradient [20% CH₃CN/H₂O to 100% CH₃CN] to the title compound as a residue.

¹H NMR (400 Hz, CD₃OD) δ 7.4 (d, 1H), 6.9 (m, 3H), 6.75 (m, 1H), 6.5 (m, 1H), 5.8 (m, 1H), 5.6 (m, 1H), 4.6 (m, 1H), 4.35 (m, 1H), 4.1-4.2 (m, 4H), 3.6-3.9 (m, 5H), 3.5 (m, 1H), 2.8-3.1 (m, 2H), 2.5-2.7 (m, 2H), 2.4 (s, 3H)

HPLC Rt=1.020 min.

MS m/z [API-ES] 486.1, 488.1 (M+H⁺).

Example 64

7-[3-(2-Methyl-1H-indol-4-yloxy)-propyl]-9-naphthalen-2-yl-7,9-diaza-bicyclo[4.2.2]dec-3-ene

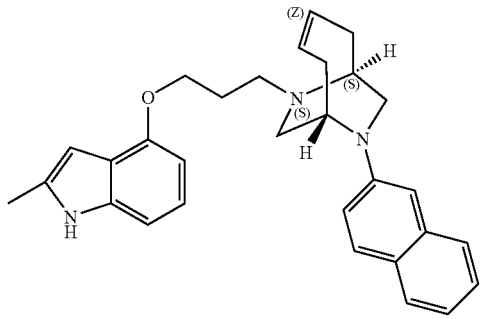

4-(3-Chloro-propoxy)-2-methyl-1H-indole (0.16 g, 0.72 mmol), Z-(1S,6S)-7-naphthalen-2-yl-7,9-diaza-bicyclo[4.2.2]dec-3-ene (0.1 g, 0.38 mmol), K₂CO₃ (72 mg, 0.52 mmol), acetonitrile (30 mL) were placed in a round bottom flask and refluxed overnight. To the reaction mixture were then added ethyl acetate (100 mL) and water (100 mL) and the resulting mixture stirred for 30 minutes. The organic layer was separated and dried with magnesium sulfate, filtered and the solvent evaporated under reduced pressure to yield a crude solid. The crude solid was purified with flash chromatography gradient [20% Ethyl acetate/heptane to 100% Ethyl acetate] to yield the title compound as a residue.

¹H NMR (300 Hz, CDCl₃) δ 7.85 (bs, 1H), 7.5-7.7 (m, 3H), 7.3 (t, 1H), 7.1 (m, 2H), 6.9 (d, 1H), 6.8 (s, 1H), 6.5 (d, 1H), 6.3 (s, 1H), 5.4 (s, 2H), 4.2 (t, 2H), 4.0 (m, 1H), 3.8 (m, 1H), 3.45 (m, 1H), 3.25 (m, 2H), 2.8-3.0 (m, 4H), 2.6 (m, 2H), 2.45 (s, 3H)

HPLC Rt=3.608 min.

MS m/z [API-ES] 452.2 (M+H⁺).

Example 65

1-(2-Methyl-1H-indol-4-yloxy)-3-[9-(1,2,3,4-tetrahydro-naphthalen-2-yl)-7,9-diaza-bicyclo[4.2.2]dec-7-yl]-propan-2-ol

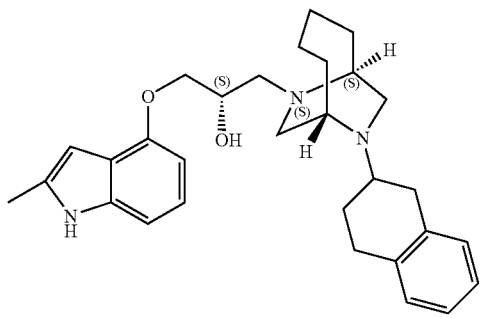

1-(2-Methyl-1H-indol-4-yloxy)-3-(9-naphthalen-2-yl-7,9-diaza-bicyclo[4.2.2]dec-3-en-7-yl)-propan-2-ol (0.05 g, 0.107 mmol), 10% Pd/C (0.05 g), methanol (15 mL) were placed in an hydrogenation bottle under H₂ atmosphere (60 psi) and shaken overnight. The resulting mixture was filtered and the solvent evaporated under reduced pressure to yield a crude solid. The crude solid was purified with flash chromatography [20% Ethyl acetate/heptane] to yield the title compound as a residue.

¹H NMR (300 Hz, CDCl₃) δ 7.9 (bs, 1H), 6.9-7.1 (m, 3H), 6.55 (t, 2H), 6.35 (d, 2H), 4.1-4.2 (m, 3H), 3.8 (m, 1H), 3.1-3.7 (m, 10H), 2.9 (m, 1H), 2.6-2.7 (m, 4H), 2.4 (s, 3H), 2.2 (m, 1H), 2.0 (m, 1H), 1.8 (m, 10H)

HPLC Rt=3.913 min.

MS m/z [API-ES] 474.3 (M+H⁺).

Example 66

4-[3-Hydroxy-4-(9-naphthalen-2-yl-7,9-diaza-bicyclo[4.2.2]dec-3-en-7-yl)-butyl]-6-methoxy-1H-indole-2-carboxylic acid methyl ester

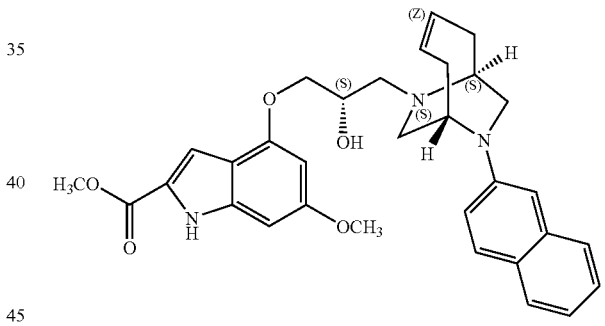

6-Methoxy-4-(2-oxiranyl-ethyl)-1H-indole-2-carboxylic acid methyl ester (120 mg, 0.43 mmol), Z-(1S,6S)-7-naphthalen-2-yl-7,9-diaza-bicyclo[4.2.2]dec-3-ene (114 mg, 0.43 mmol), DIPEA (0.2 mL, 1.13 mmol), ethanol (3 mL), dichloromethane (2 mL) were heated for 1200 sec. at 130° C. in a μW reaction tube. The solvent was evaporated under reduced pressure to yield a crude solid which was then purified with flash chromatography gradient [20% Ethyl acetate/heptane to 100% Ethyl acetate] to yield the title compound as a residue.

¹H NMR (400 Hz, CDCl₃) δ 8.7 (bs, 1H), 7.6-7.75 (m, 3H), 7.4 (m, 2H), 7.2 (m, 1H), 7.05 (m, 1H), 6.8 (m, 1H), 6.45 (s, 1H), 6.2 (s, 1H), 5.5 (m, 2H), 4.1 (m, 3H), 3.9 (s, 3H), 3.85 (s, 3H), 3.5 (m, 3H), 3.35 (m, 1H), 3.0 (m, 4H), 2.8 (m, 1H), 2.6 (m, 3H), 2.3 (m, 1H)

HPLC Rt=3.694 min.

MS m/z [API-ES] 542.3 (M+H⁺).

Example 67

4-(2,5-Dimethyl-1H-indol-4-yl)-1-(9-naphthalen-2-yl-7,9-diaza-bicyclo[4.2.2]dec-3-en-7-yl)-butan-2-ol

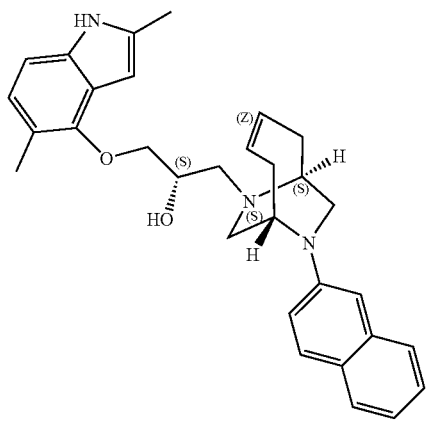

2,5-Dimethyl-4-(2-oxiranyl-ethyl)-1H-indole (50 mg, 0.23 mmol), Z-(1S,6S)-7-naphthalen-2-yl-7,9-diaza-bicyclo[4.2.2]dec-3-ene (45 mg, 0.17 mmol), DIPEA (0.1 mL, 0.55 mmol), ethanol (3 mL) were heated for 900 sec. at 120° C. in a μW reaction tube. The solvent was evaporated under reduced pressure to yield a crude solid that was purified with flash chromatography gradient [20% Ethyl acetate/heptane to 100% Ethyl acetate] to yield the title compound as a residue.

$^1$H NMR (400 Hz, CDCl$_3$) δ 7.8 (bs, 1H), 7.6-7.75 (m, 3H), 7.35 (t, 1H), 7.2 (t, 1H), 7.05 (m, 1H), 6.9 (q, 2H), 6.8 (s, 1H), 6.3 (s, 1H), 5.5 (m, 2H), 4.2 (m, 2H), 4.1 (m, 2H), 3.9 (m, 1H), 3.5 (m, 2H), 3.35 (m, 1H), 3.0 (m, 3H), 2.8 (m, 1H), 2.6 (m, 3H), 2.45 (s, 3H), 2.4 (s, 3H) 2.3 (m, 1H)

HPLC Rt=3.857 min.
MS m/z [API-ES] 482.2 (M+H$^+$).

Example 68

1-(2,7-Dimethyl-1H-indol-4-yloxy)-3-(9-naphthalen-2-yl-7,9-diaza-bicyclo[4.2.2]dec-3-en-7-yl)-propan-2-ol

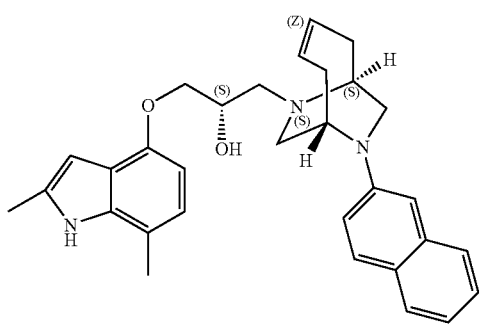

2,7-Dimethyl-4-oxiranylmethoxy-1H-indole (30 mg, 0.138 mmol), Z-(1S,6S)-7-naphthalen-2-yl-7,9-diaza-bicyclo[4.2.2]dec-3-ene (40 mg, 0.15 mmol), DIPEA (0.1 mL, 0.55 mmol), ethanol (2 mL) were heated for 900 sec. at 120° C. in a μW reaction tube to yield crude product. The solvent was evaporated under reduced pressure to yield a solid that was purified with flash chromatography gradient [0% Ethyl acetate/heptane to 100% Ethyl acetate] to yield the title compound as a residue.

$^1$H NMR (400 Hz, CDCl$_3$) δ 7.7 (bs, 1H), 7.5-7.65 (m, 3H), 7.25 (t, 1H), 7.1 (t, 1H), 6.95 (d, 1H), 6.8 (m, 2H), 6.4 (d, 1H), 6.3 (s, 1H), 5.4 (m, 2H), 4.2 (m, 1H), 4.1 (m, 2H), 3.95 (m, 1H), 3.8 (m, 1H), 3.4 (m, 2H), 3.25 (bs, 1H), 2.8-3.0 (m, 3H), 2.7 (m, 1H), 2.45-2.6 (m, 3H), 2.4 (s, 3H) 2.3 (s, 3H), 2.2 (m, 1H)

HPLC Rt=4.068 min.
MS m/z [API-ES] 482.2 (M+H$^+$).

Example 69

1-[9-(2,3-Dihydro-benzo[1,4]dioxin-6-yl)-7,9-diaza-bicyclo[4.2.2]dec-3-en-7-yl]-3-(2-methyl-1H-indol-4-yloxy)-propan-2-ol

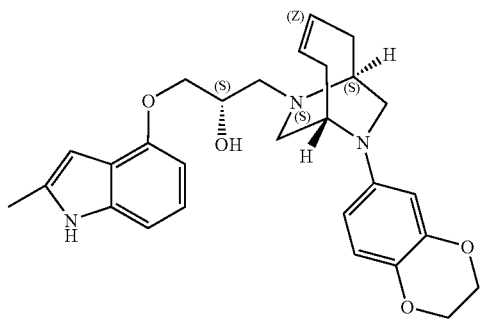

2-Methyl-4-oxiranylmethoxy-1H-indole (25 mg, 0.123 mmol), 7-(2,3-dihydro-benzo[1,4]dioxin-6-yl)-7,9-diaza-bicyclo[4.2.2]dec-3-ene (34 mg, 0.125 mmol), chloroform (1 mL), ethanol (3 mL) were heated for 900 sec. at 130° C. in a μW reaction tube. The solvent was evaporated under reduced pressure to yield a crude solid that was purified with flash chromatography gradient [20% Ethyl acetate/heptane to 100% Ethyl acetate] to yield the title compound as a residue.

$^1$H NMR (400 Hz, CDCl$_3$) δ 7.88 (bs, 1H), 7.0 (m, 1H), 6.9 (d, 1H), 6.8 (d, 1H), 6.5 (d, 1H), 6.3 (bs, 1H), 6.15 (m, 2H), 5.5 (m, 2H), 4.1-4.3 (m, 7H), 3.8 (m, 1H), 3.7 (m, 2H), 3.45 (m, 1H), 3.2 (m, 2H), 3.0 (m, 1H), 2.85 (m, 2H), 2.7 (m, 1H), 2.6 (m, 1H), 2.4 (s, 3H), 2.2 (m, 1H)

HPLC Rt=3.848 min.
MS m/z [API-ES] 476.2 (M+H$^+$).

Example 70

1-(9-Naphthalen-2-yl-7,9-diaza-bicyclo[4.2.2]dec-3-en-7-yl)-3-(quinolin-5-yloxy)-propan-2-ol

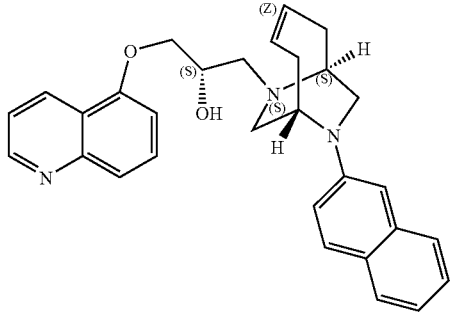

5-Oxiranylmethoxy-quinoline (13 mg, 0.065 mmol), 7-naphthalen-2-yl-7,9-diaza-bicyclo[4.2.2]dec-3-ene (20 mg, 0.042 mmol), DIPEA (0.1 mL, 0.55 mmol) and ethanol (2 mL) were μW for 900 sec at 130° C. in a μW reaction tube. The solvent was evaporated in vacuo to yield a crude solid that was purified with flash chromatography gradient [30% EtOAc/heptane to 100% EtOAc] to yield the title compound as its free base, as a residue.

$^1$H NMR (400 MHz, CDCl$_3$) δ 8.85 (m, 1H), 8.55 (m, 1H), 7.5-7.7 (m, 5H), 7.2-7.35 (m, 2H), 7.1 (t, 1H), 7.0 (m, 1H), 6.85 (m, 1H), 6.75 (s, 1H), 5.4 (m, 2H), 4.1-4.25 (m, 4H), 4.0 (m, 2H), 3.8 (m, 1H), 3.4-3.5 (m, 2H), 3.25 (bs, 1H), 2.9-3.0 (m, 3H), 2.75 (m, 1H), 2.5-2.6 (m, 2H), 2.2 (m, 1H)

HPLC Rt=3.723 min.

MS m/z [API-ES] 466.2 (M+H$^+$).

Example 71

1-[9-(2,3-Dihydro-benzo[1,4]dioxin-6-yl)-7,9-diaza-bicyclo[4.2.2]dec-3-en-7-yl]-3-(2-methyl-1H-indol-4-yloxy)-propan-2-ol

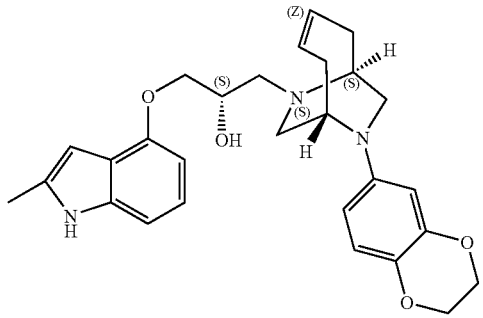

2-Methyl-4-oxiranylmethoxy-1H-indole (25 mg, 0.123 mmol), 7-naphthalen-2-yl-7,9-diaza-bicyclo[4.2.2]dec-3-ene (34 mg, 0.125 mmol), ethanol (5 mL) and CHCl$_3$ (1 mL) were µW for 900 sec at 130° C. in a µW reaction tube. The solvent was evaporated in vacuo to yield a crude solid that was purified with flash chromatography gradient [20% EtOAc/heptane to 100% EtOAc] to yield the title compound as a residue.

$^1$H NMR (300 MHz, CDCl$_3$) δ 7.85 (bs, 1H), 7.0 (t, 1H), 6.9 (d, 1H), 6.8 (d, 1H), 6.5 (d, 1H), 6.3 (bs, 1H), 6.2 (m, 2H), 5.5 (bs, 2H), 4.25 (m, 4H), 4.2 (m, 1H), 4.1 (m, 2H), 3.8 (m, 1H), 3.7 (m, 2H), 3.5 (m, 1H), 3.2 (m, 2H), 3.0 (m, 1H), 2.85 (m, 2H), 2.7 (m, 1H), 2.6 (m, 1H), 2.4 (s, 3H), 2.2 (m, 2H)

HPLC Rt=3.847 min.

MS m/z [API-ES] 476.2 (M+H$^+$).

Example 72

7-Indan-2-yl-9-naphthalen-2-yl-7,9-diaza-bicyclo[4.2.2]dec-3-ene

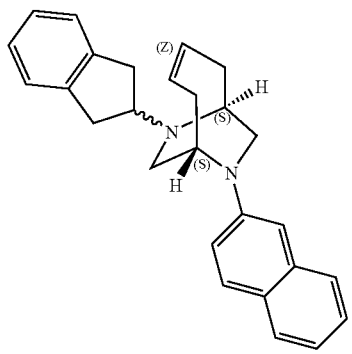

A mixture of indan-2-one (45 mg, 0.34 mmol), Z-(1S,6S)-7-naphthalen-2-yl-7,9-diaza-bicyclo[4.2.2]dec-3-ene (50 mg, 0.19 mmol), sodium triacetoxyborohydride (45 mg, 0.212 mmol), DCE (20 mL), acetic acid (13 µL) was stirred at room temperature overnight. To the reaction mixture was then added 1N NaOH and ethyl acetate. The organic layer was separated, dried with magnesium sulfate, filtered and the solvent evaporated under reduced pressure to yield a crude solid that was purified with flash chromatography gradient [20% Ethyl acetate/heptane to 100% Ethyl acetate] to yield the title compound as a residue.

$^1$H NMR (400 Hz, CDCl$_3$) δ 7.55-7.6 (m, 3H), 7.1-7.4 (m, 6H), 7.0 (d, 1H), 6.75 (s, 1H), 5.5 (m, 2H), 4.1 (m, 1H), 3.9 (m, 1H), 3.7 (m, 1H), 3.5 (m, 2H), 2.9-3.3 (m, 6H), 2.6 (m, 3H), 2.3 (m, 1H)

HPLC Rt=3.766 min.

MS m/z [API-ES] 381.1 (M+H$^+$).

Example 73

7,9-Diaza-bicyclo[4.2.2]decane-7,9-dicarboxylic acid di-tert-butyl ester

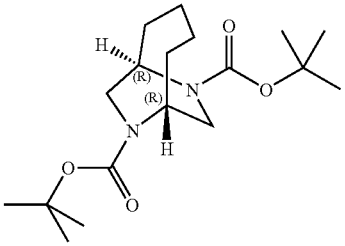

To a suspension of R,R—(Z)-7,9-diaza-bicyclo[4.2.2]decane-8,10-dione (164 mg, 0.98 mmol) in THF (20 mL) was added LAH (1 M in THF, 9.8 mL, 9.8 mmol) at 0° C. The resulting mixture was stirred at 65° C. for 48 h and then cooled to 0° C. Brine (0.1 mL) was then added to quench the reaction. The resulting mixture was filtered through a pad of Celite®, and the resulting solution concentrated in vacuo. The resulting residue was dissolved in CH$_2$Cl$_2$ (6 mL), and added to a solution of Boc-anhydride (Boc$_2$O) in CH$_2$Cl$_2$ (20 mL). The resulting mixture was stirred for 24 h at room temperature, and then quenched by addition of saturated NaHCO$_3$ solution (4 mL). The aqueous layer was extracted with CH$_2$Cl$_2$ (10 mL) twice. The combined organic solution was washed with brine and dried over MgSO$_4$. The concentrated residue was purified on silica gel column with a gradient eluent (Hexane:Ethyl acetate 95:5 to 80:20) to yield the title compound as a white solid.

$^1$H NMR (300 MHz, CDCl$_3$) δ 4.25 (m, 2H), 3.86-3.74 (m, 1H), 3.73-3.59 (m, 1H), 3.58-3.40 (m, 2H), 2.30-2.06 (m, 2H), 1.65-1.55 (m, 4H), 1.53-1.44 (m, 20H)

$^{13}$C NMR (75 MHz, a mixture of conformer peaks) 6155.4, 155.3, 155.1, 155.0, 80.1, 80.0, 80.0, 51.7, 51.5, 51.2, 51.0, 45.8, 45.7, 45.1, 45.0, 34.2, 33.9, 33.3, 33.0, 28.9, 24.4, 24.3, 24.3, 24.2

Elemental Analysis for C$_{18}$H$_{32}$N$_2$O$_4$:

Calculated: C, 63.50; H, 9.47; N, 8.23

Measured: C, 63.14; H, 9.22; N, 7.97. .

Example 74

7,9-Diaza-bicyclo[4.2.2]decane, di-TFA salt

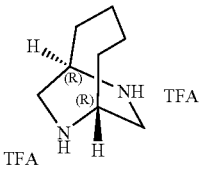

7,9-Diaza-bicyclo[4.2.2]decane-7,9-dicarboxylic acid di-tert-butyl ester (132 mg, 0.39 mmol) was dissolved in TFA (4 mL). The resulting mixture was stirred for 2 h at room temperature. The solvent was then evaporated, and the residue was triturated with anhydrous diethyl ether to yield the title compound as a white solid.

$^1$H NMR (300 MHz, CDCl$_3$) δ 5.57-4.50 (bs, 4H), 4.19-4.11 (m, 2H), 3.70 (dd, J=14.7, 5.7 Hz, 2H), 3.52 (dd, J=14.8, 1.2 Hz, 2H), 2.20-1.94 (m, 6H), 1.92-1.68 (m, 2H)

$^{13}$C NMR (75 MHz) δ 163.0 (m, 2C), 118.0 (q, J=291.8 Hz, 2C), 48.7 (2C), 39.5 (2C), 32.4 (2C), 23.2 (2C)

Elemental Analysis for C$_{12}$H$_{18}$F$_6$N$_2$O$_4$:
Calculated: C, 39.14; H, 4.93; N, 7.61.
Measured: C, 38.87; H, 4.67; N, 7.37.

Example 75

7,9-Diaza-bicyclo[4.2.2]dec-3-ene-7,9-dicarboxylic acid di-tert-butyl ester

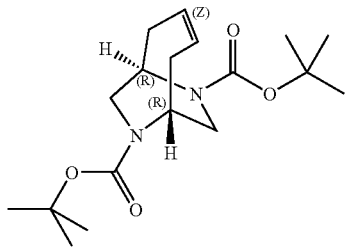

To the suspension of R,R—(Z)-7,9-diaza-bicyclo[4.2.2]dec-3-ene-8,10-dione (83 mg, 0.50 mmol) in anhydrous diethyl ether (5 mL) was added LAH (1 M in diethyl ether, 5.0 mL, 5.0 mmol) at 0° C. The resulting mixture was stirred at 35° C. for 48 h and then diluted with diethyl ether and cooled down to 0° C. Na$_2$SO$_4$.10H$_2$O (644.4 mg, 2.0 mmol) was then added to quench the reaction. The resulting mixture was filtered through a pad of Celite®, and concentrated in vacuo. The resulting residue was dissolved in CH$_2$Cl$_2$ (4 mL), and added to a solution of Boc-anhydride (Boc$_2$O) (436.5 mg, 2.0 mmol) in CH$_2$Cl$_2$ (2 mL). The resulting mixture was stirred for 24 h at room temperature, and then quenched by addition of saturated NaHCO$_3$ solution (4 mL). The aqueous layer was extracted with CH$_2$Cl$_2$ (10 mL) twice. The combined organic solution was washed with brine and dried over MgSO$_4$. The concentrated residue was purified on silica gel column with gradient eluent (Hexane:Ethyl acetate 90:10 to 70:30) to yield the title compound as a white solid.

$^1$H NMR (300 MHz, CDCl$_3$) δ 5.62-5.40 (m, 2H), 4.23-4.00 (m, 2H), 3.90-3.77 (m, 1H), 3.75-3.60 (m, 1H), 3.51-3.35 (m, 2H), 2.85-2.63 (m, 2H), 2.20-2.02 (m, 2H), 1.44 (s, 9H), 1.44 (s, 9H)

$^{13}$C NMR (75 MHz, a mixture of conformers) δ 155.6, 155.5, 155.4, 127.8, 127.0, 126.4, 125.5, 80.2, 80.1 (m), 51.8, 51.7, 51.4, 51.3, 46.9, 46.7, 45.7, 45.6, 33.6, 33.5, 33.1, 33.0, 28.8

Elemental Analysis for C$_{18}$H$_{30}$N$_2$O$_4$:
Calculated: C, 63.88; H, 8.93; N, 8.28.
Measured: C, 63.69; H, 9.20; N, 8.14.

Example 76

7,9-Diaza-bicyclo[4.2.2]dec-3-ene

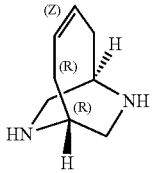

To a stirred solution of R,R-7,9-diaza-bicyclo[4.2.2]dec-3-ene-7,9-dicarboxylic acid di-tert-butyl ester (48 mg, 0.14 mmol) in CH$_2$Cl$_2$ (2 mL) was added TFA (2 mL) at room temperature. The resulting mixture was stirred at room temperature overnight. After all volatiles were evaporated, the residue was re-dissolved in methanol (1 mL) and toluene (2 mL) and then concentrated. This process was repeated three times. Final treatment with diethyl ether yielded the title compound as a white solid.

$^1$H NMR (300 MHz, CDCl$_3$) δ 5.70-5.65 (m, 2H), 5.30-4.70 (m, 4H), 4.25-4.16 (m, 2H), 3.77 (dd, J=14.3, 4.9 Hz, 2H), 3.48 (dd, J=14.5, 1.6 Hz, 2H), 3.04-2.88 (m, 2H), 2.74-2.60 (m, 2H)

$^{13}$C NMR (75 MHz) δ 163.7 (q, J=34.6 Hz, 2C), 125.3 (2C), 118.5 (q, J=292.4 Hz, 2C), 48.0 (2C), 41.2 (2C), 32.5 (2C)

Elemental Analysis for C$_{12}$H$_{16}$F$_6$N$_2$O$_4$:
Calculated: C, 39.35; H, 4.4; N, 7.65.
Measured: C, 39.71; H, 4.23; N, 7.63.

Example 77

Radioligand Binding to the 5-HT1A (Serotonin-1A) Receptor and to 5-HTT (Serotonin Transporter, SERT)

Frozen membranes of HEK293 cells, stably-transfected with human 5-HT1A receptor (Perkin Elmer) were thawed on ice, briefly homogenised with an Ultra Turrax homogeniser and then suspended in Tris-HCl buffer (50 mM pH 7.7) supplemented with CaCl$_2$ (4 mM) at an appropriate pre-determined protein concentration (5-10 µg protein per incubation mixture). Together with [$^3$H]8-OH-DPAT (0.5 nM final concentration; Perkin Elmer, USA), the membrane suspension was added to the test compound and incubated (30 min at 37° C.) in a total volume of 400 µl. Non-specific binding was determined in the presence of Spiroxatrine (1 µM). Free radioligand was separated from the radioligand-receptor complex by means of rapid vacuum filtration over GF/B unifilter plates with a Packard Harvester Filtration Unit. Unifilter plates were washed with ice cold Tris-HCl buffer (50 mM, pH 8.0) and then dried overnight. Bound counts were measured in a Topcount Scintillation Counter in the presence of Microscint O.

For 5-HTT binding, frozen membranes of HEK293 cells stably-transfected with human 5-HTT (Perkin-Elmer, USA) were thawed on ice, briefly homogenised and resuspended in Tris-HCl buffer (50 mM, pH 7.4) supplemented with NaCl (120 mM) and KCl (5 mM) at a concentration of 50 µg protein per incubation mixture. The membrane suspension was added to the test compound together with [$^3$H]Paroxetine (0.5 nM)

in a total volume of 250 µl and incubated (60 min, 25° C.). Non-specific binding was determined in the presence of imipramine (1 µM). Filtration was done over pre-soaked GF/B unifilters (0.01% PEI) and washed as above with the Tris-HCl salt buffer used for the incubation. Specific binding was calculated and sigmoidal curves were plotted by an internally-developed software program based on S-plus software. $K_i$ values were calculated using the Cheng-Prusoff equation.

Example 78

[35S]GTPγS Binding for 5-HT1A Receptor Activation and Inhibition

Compounds showing affinity at the 5-HT1A receptor were tested for functional agonism and antagonism in a [$^{35}$S]GTPγS (guanine triphosphate (non-hydrolysable, labelled with $^{35}$S) binding assay on membranes of HEK293 cells permanently transfected with human 5HT1A receptor (Perkin Elmer, USA).

Frozen membranes were thawed, briefly homogenized and were diluted in incubation buffer, 100 mM NaCl, 0.3 mM $MgCl_2$ and 10 µM guanine diphosphate (GDP), pH 7.4-7.5) supplemented with 10 µg/ml saponin. Assay mixtures contained 10 µg of membrane protein and test compound, buffer, or control agonist (serotonin, 10 µM). For the antagonistic assay, control agonist was present in all wells containing compound at a sub-maximal concentration (serotonin, 100 nM). After 20 minutes pre-incubation at 37° C., [$^{35}$S]GTPγS was added to a final concentration of 0.25 nM, briefly shaken and further incubated for another 20 minutes. Reactions were terminated by rapid vacuum filtration through GF/B unifilter plates using a Packard Harvester. Filters were washed three times with wash buffer (10 mM $NaH_2PO_4$, 10 mM $Na_2HPO_4$, pH 7.4), dried overnight and bound counts were measured in a Topcount Scintillation Counter in the presence of Microscint O. % Specific Binding was calculated and curves were plotted with help of in house software where $pIC_{50}$ values were determined and $K_b$ values were calculated.

Representative compounds of the present invention were tested according to the procedures outlined in Examples BIO1 and BIO2 above, with results as listed in Table 9, below. For the listed $IC_{50}$ values, a notation of less than five (<5) indicates that the compound was not active at up to 10 µM treatment concentrations.

TABLE 9

Biological Assay Results

| | Example 77 | | Example 78 | |
|---|---|---|---|---|
| ID No. | h5HTT $pIC_{50}$ | h5HT1A $pIC_{50}$ | h5HT1A Agonist $pIC_{50}$ | h5HT1A Antagonist $pIC_{50}$ |
| 1 | 7.43 | 6.44 | <5 | 5.18 |
| 1 | 7.49 | 6.75 | <5 | 5.37 |
| 2 | < | <5 | | |
| 3 | 5.99 | 7.77 | <5 | 6.76 |
| 3 | 5.44 | 6.53 | <5 | 5.66 |
| 4 | 7.59 | <5 | | |
| 5 | 5.95 | 6.38 | 5.77 | <5 |
| 6 | 7.58 | 5.71 | | |
| 7 | 7.52 | <5 | | |
| 8 | 6.22 | <5 | | |
| 9 | 5.88 | 4.98 | | |
| 10 | 6.63 | 5.55 | | |
| 11 | <5 | <5 | | |
| 12 | <5 | <5 | | |
| 13 | <5 | <5 | | |

TABLE 9-continued

Biological Assay Results

| | Example 77 | | Example 78 | |
|---|---|---|---|---|
| ID No. | h5HTT $pIC_{50}$ | h5HT1A $pIC_{50}$ | h5HT1A Agonist $pIC_{50}$ | h5HT1A Antagonist $pIC_{50}$ |
| 14 | 5.73 | <5 | | |
| 15 | 5.09 | <5 | | |
| 16 | 6.25 | <5 | | |
| 17 | 7.55 | <5 | | |
| 18 | <5 | <5 | | |
| 19 | 5.80 | <5 | | |
| 20 | 5.56 | <5 | | |
| 21 | <5 | <5 | | |
| 22 | 5.76 | <5 | | |
| 23 | <5 | <5 | | |
| 24 | 5.68 | <5 | | |
| 25 | 5.07 | <5 | | |
| 26 | <5 | <5 | | |
| 27 | 7.54 | <5 | | |
| 28 | 5.55 | <5 | | |
| 29 | 6.75 | <5 | | |
| 30 | 7.94 | 5.08 | <5 | <5 |
| 31 | 6.26 | 5.04 | <5 | <5 |
| 32 | 5.35 | 5.12 | <5 | <5 |
| 33 | 6.63 | <5 | | |
| 34 | 5.84 | <5 | | |
| 35 | 5.83 | 5.26 | <5 | <5 |
| 37 | 6.22 | 5.43 | <5 | <5 |
| 38 | 6.71 | 7.08 | <5 | <5 |
| 38 | 6.71 | 7.29 | <5 | <5 |
| 39 | 7.63 | 7.31 | <5 | 6.42 |
| 39 | 7.76 | 7.04 | <5 | 6.18 |
| 39 | 7.5 | 7.22 | <5 | 5.72 |
| 41 | 7.07 | <5 | | |
| 42 | 6.42 | <5 | | |
| 43 | 7.31 | <5 | | |
| 44 | 7.64 | <5 | | |
| 45 | 7.28 | 5.665 | 5.60 | <5 |
| 46 | 7.59 | <5 | | |
| 48 | 6.66 | <5 | | |
| 49 | 6.06 | 5.4 | <5 | <5 |
| 50 | 6.34 | <5 | | |
| 51 | 6.33 | <5 | | |
| 52 | <5 | <5 | | |
| 53 | 6.33 | <5 | | |
| 54 | 7.10 | 6.47 | 5.84 | <5 |
| 55 | 6.86 | 6.88 | 6.46 | <5 |
| 119 | 7.15 | <5 | | |
| 126 | 7.62 | 7.30 | 6.76 | <5 |
| 127 | 7.40 | 6.44 | <5 | <5 |
| 128 | 7.52 | 6.25 | <5 | <5 |
| 135 | 6.99 | 7.01 | 6.15 | 6.09 |
| 136 | 6.18 | 7.87 | 7.17 | 6.51 |
| 137 | 6.17 | 5.63 | <5 | <5 |
| 138 | 7.55 | 6.55 | 6.62 | 4.96 |
| 140 | 6.13 | <5 | | |
| 141 | 6.14 | <5 | | |
| 142 | 6.99 | 5.01 | <5 | <5 |
| 143 | 6.76 | 6.62 | <5 | <5 |
| 145 | 6.29 | 6.94 | <5 | 5.58 |
| 147 | 6.72 | 6.83 | <5 | <5 |
| 147 | 6.99 | 6.61 | <5 | 5.89 |
| 148 | 7.27 | 6.86 | 6.25 | <5 |
| 150 | 5.72 | <5 | | |
| 151 | 7.49 | 6.29 | <5 | <5 |
| 152 | 7.28 | 6.22 | <5 | <5 |
| 153 | 7.24 | 6.03 | <5 | <5 |
| 154 | 7.26 | 6.14 | <5 | <5 |
| 155 | 6.96 | 7.28 | 6.76 | <5 |
| 155 | 6.67 | 6.94 | 6.67 | 5.2 |
| 156 | 7.53 | <5 | <5 | <5 |
| 157 | 7.7 | 7.21 | <5 | 6.12 |
| 158 | 6.6 | 6.9 | 6.17 | 5.94 |
| 159 | 6.12 | 7.97 | <5 | 7.32 |
| 160 | 7.2 | 6.45 | <5 | 6.07 |

Example 79

Prophetic Example

As a specific embodiment of an oral composition, 100 mg of the compound #136 or compound #138 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound selected from the group consisting of formula (I)

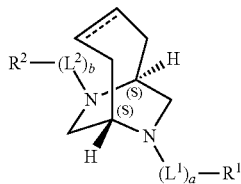

and formula (II)

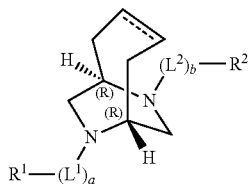

wherein
═══ is a single or double bond;
a is an integer from 0 to 1;
$L^1$ is selected from the group consisting of —$C_{1-4}$-alkyl-, —$CH_2$—$C_{2-4}$-alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)—, —($C_{2-4}$alkyl)-$NR^A$, —($C_{1-4}$alkyl)-$SO_2$—, —C(O)—($C_{1-4}$-alkyl)-, —O—($C_{1-4}$-alkyl), —C(O)O—($C_{1-4}$-alkyl)-, —$NR^A$—($C_{1-4}$-alkyl)-, —($C_{1-4}$-alkyl)-O—($C_{1-4}$ alkyl)-, —($C_{1-4}$-alkyl)-C(O)—($C_{1-4}$alkyl)-, —($C_{1-4}$-alkyl)-OC(O)—($C_{1-4}$-alkyl)-, —($C_{1-4}$-alkyl)-C(O)O—($C_{1-4}$-alkyl)-, —($C_{2-4}$alkyl)-$NR^A$—($C_{1-4}$-alkyl)-, —($C_{1-4}$-alkyl)-$SO_2$—($C_{1-4}$-alkyl)-, —C(O)—$NR^A$—, —C(O)—$NR^A$—($C_{1-4}$alkyl)-, —$NR^A$—C(O)— and —$NR^A$—C(O)—($C_{1-4}$-alkyl)-;
wherein the —$C_{1-4}$-alkyl- or $C_{2-4}$alkyl, whether alone or as part of a substituent group is optionally substituted with one or more substituents independently selected from the group consisting of hydroxy, $C_{1-4}$-alkoxy, amino, ($C_{1-4}$-alkyl)amino, di($C_{1-4}$-alkyl)amino, phenyl, SH and S($C_{1-4}$-alkyl);
wherein $R^A$ is selected from the group consisting of hydrogen, —$C_{1-4}$-alkyl phenyl, —C(O)—($C_{1-4}$-alkyl), —C(O)-carbocyclyl, —C(O)-heterocyclyl, —$SO_2$—($C_{1-4}$-alkyl)-$SO_2$-carbocyclyl and —$SO_2$-heterocyclyl;

provided that the chain length of $L^1$, not counting branching, is one to six atoms;
$R^1$ is selected from the group consisting of hydrogen, $C_{1-4}$-alkyl, cycloalkyl, partially unsaturated carbocyclyl, aryl and biphenyl;
wherein the cycloalkyl, partially unsaturated carbocyclyl or aryl, whether alone or as part of a substituent group is optionally substituted with one or more substituents independently selected from the group consisting of halogen, hydroxy, carboxy, oxo, $C_{1-4}$-alkyl, $C_{1-4}$alkoxy, halogenated $C_{1-4}$-alkyl, halogenated $C_{1-4}$-alkoxy, hydroxy substituted $C_{1-4}$-alkyl, cyano, nitro, amino, $C_{1-4}$-alkylamino, di($C_{1-4}$-alkyl)amino, [1,3]dioxolanyl, alkoxy-C(O)—, $NR^BR^C$—C(O)— and —$SO_2$—$NR^BR^C$;
wherein $R^B$ and $R^C$ are each independently selected from the group consisting of hydrogen and $C_{1-4}$-alkyl;
b is an integer from 0 to 1;
$L^2$ is selected from the group consisting of —$C_{1-4}$-alkyl-, —$CH_2$—$C_{2-4}$-alkenyl-, —$CH_2$—$C_{2-4}$alkynyl-, —$SO_2$—, —C(O)—, —C(O)O—, —($C_{1-4}$alkyl)-C(O)—, —($C_{1-4}$alkyl)-O—, —($C_{1-4}$alkyl)-C(O)O—, —($C_{2-4}$alkyl)-$NR^D$, —($C_{1-4}$alkyl)-$SO_2$—, —C(O)—($C_{1-4}$-alkyl)-, —O—($C_{1-4}$-alkyl), —C(O)O—($C_{1-4}$-alkyl)-, —$NR^D$—($C_{1-4}$-alkyl)-, —($C_{1-4}$-alkyl)-O—($C_{1-4}$ alkyl)-, —($C_{1-4}$-alkyl)-C(O)—($C_{1-4}$alkyl)-, —($C_{1-4}$ alkyl)-OC(O)—($C_{1-4}$-alkyl)-, —($C_{1-4}$-alkyl)-C(O)O—($C_{1-4}$-alkyl)-, —($C_{2-4}$alkyl)-$NR^D$—($C_{1-4}$-alkyl)-, —($C_{1-4}$-alkyl)-$SO_2$—($C_{1-4}$-alkyl)-, —C(O)—$NR^D$—, —C(O)—$NR^D$—($C_{1-4}$alkyl)-, —$NR^D$—C(O)— and —$NR^D$—C(O)—($C_{1-4}$-alkyl)-;
wherein the —$C_{1-4}$-alkyl- or $C_{2-4}$alkyl, whether alone or as part of a substituent group is optionally substituted with one or more substituents independently selected from the group consisting of hydroxy, $C_{1-4}$-alkoxy, amino, ($C_{1-4}$-alkyl)amino, di($C_{1-4}$-alkyl)amino, phenyl, SH and S($C_{1-4}$-alkyl);
wherein $R^D$ is selected from the group consisting of hydrogen, —$C_{1-4}$-alkyl phenyl, —C(O)—($C_{1-4}$-alkyl), —C(O)-carbocyclyl, —C(O)-heterocyclyl, —$SO_2$—($C_{1-4}$-alkyl)-$SO_2$-carbocyclyl and —$SO_2$-heterocyclyl;
provided that the chain length of $L^2$, not counting branching, is one to six atoms;
$R^2$ is selected from the group consisting of hydrogen, $C_{1-4}$-alkyl, cycloalkyl, partially unsaturated carbocyclyl, aryl, biphenyl, heteroaryl and heterocycloalkyl;
wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, $C_{1-4}$-alkyl, $C_{1-4}$-alkoxy, halogenated $C_{1-4}$-alkyl, halogenated $C_{1-4}$-alkoxy, hydroxy substituted $C_{1-4}$-alkyl, cyano, nitro, amino, $C_{1-4}$-alkylamino, di($C_{1-4}$alkyl) amino, [1,3]dioxolanyl, —$C_{1-4}$-alkoxy-C(O)—, $NR^ER^F$—C(O)— and —$SO_2$—$NR^ER^F$;
wherein $R^E$ and $R^F$ are each independently selected from the group consisting of hydrogen and $C_{1-4}$-alkyl;
provided that the chain length of $L^1$, not counting branching, plus the chain length of $L^2$, not counting branching, is not greater than about 12 atom;
provided further that when a is 0 and b is 0 then $R^1$ and $R^2$ are not each hydrogen;
or a pharmaceutically acceptable salt thereof.
2. A compound as in claim 1, selected from the group consisting of formula (I) and formula (II), wherein
═══ is a single or double bond;

a is an integer from 0 to 1;

$L^1$ is selected from the group consisting of —$C_{1-4}$-alkyl-, —$CH_2$—$C_{2-4}$-alkenyl-, —$CH_2$—$C_{2-4}$alkynyl-, —C(O)—, —C(O)O—, —($C_{1-4}$-alkyl)-C(O)—, ($C_{1-4}$-alkyl)-O—, —($C_{1-4}$-alkyl)-C(O)O—, —($C_{2-4}$alkyl)-$NR^A$, —C(O)—($C_{1-4}$alkyl)-, —C(O)O—($C_{1-4}$-alkyl)-, —($C_{1-4}$-alkyl)-O—($C_{1-4}$-alkyl)-, —C(O)—$NR^A$—, —C(O)—$NR^A$—($C_{1-4}$-alkyl)-, —$NR^A$—C(O)— and —$NR^A$—C(O)—($C_{1-4}$-alkyl)-;

wherein the —$C_{1-4}$-alkyl-, whether alone or as part of a substituent group is optionally substituted with one to two substituents independently selected from the group consisting of hydroxy, $C_{1-4}$-alkoxy, amino, ($C_{1-4}$alkyl)amino, di($C_{1-4}$-alkyl)amino and phenyl;

wherein $R^A$ is selected from the group consisting of hydrogen, —$C_{1-4}$-alkyl phenyl and —C(O)—($C_{1-4}$-alkyl);

provided that the chain length of $L^1$, not counting branching, is one to six atoms;

$R^1$ is selected from the group consisting of hydrogen, $C_{1-4}$-alkyl, cycloalkyl, aryl and biphenyl;

wherein the aryl, whether alone or as part of a substituent group is optionally substituted with one to three substituents independently selected from the group consisting of halogen, hydroxy, carboxy, oxo, $C_{1-4}$-alkyl, $C_{1-4}$-alkoxy, fluorinated $C_{1-4}$-alkyl, fluorinated $C_{1-4}$-alkoxy, hydroxy substituted $C_{1-4}$-alkyl, cyano, nitro, amino, $C_{1-4}$-alkylamino, di($C_{1-4}$-alkyl)amino, [1,3]dioxolanyl, $C_{1-4}$-alkoxy-C(O)— and $NR^B R^C$—C(O)—;

wherein $R^B$ and $R^C$ are each independently selected from the group consisting of hydrogen and $C_{1-4}$-alkyl;

b is an integer from 0 to 1;

$L^2$ is selected from the group consisting of —$C_{1-4}$-alkyl-, —$CH_2$—$C_{2-4}$-alkenyl-, —$CH_2$—$C_{2-4}$alkynyl-, —C(O)—, —C(O)O—, —($C_{1-4}$-alkyl)-C(O)—, —($C_{1-4}$-alkyl)-O—, —($C_{1-4}$-alkyl)-C(O)O—, —($C_{2-4}$alkyl)-$NR^D$, —C(O)—($C_{1-4}$alkyl)-, —C(O)O—($C_{1-4}$-alkyl)-, —($C_{1-4}$-alkyl)-O—($C_{1-4}$-alkyl)-, —($C_{2-4}$alkyl)-$NR^D$—($C_{1-4}$-alkyl)-, —C(O)—$NR^D$—, —C(O)—$NR^D$—($C_{1-4}$-alkyl)-, —$NR^D$—C(O)— and —$NR^D$—C(O)—($C_{1-4}$-alkyl)-;

wherein the —$C_{1-4}$-alkyl-, whether alone or as part of a substituent group is optionally substituted with one to two substituents independently selected from the group consisting of hydroxy, $C_{1-4}$-alkoxy, amino, ($C_{1-4}$alkyl)amino, di($C_{1-4}$-alkyl)amino and phenyl;

wherein $R^D$ is selected from the group consisting of hydrogen, —$C_{1-4}$-alkyl phenyl and —C(O)—($C_{1-4}$-alkyl);

provided that the chain length of $L^2$, not counting branching, is one to six atoms;

$R^2$ is selected from the group consisting of hydrogen, $C_{1-4}$-alkyl, cycloalkyl, aryl, biphenyl, heteroaryl and heterocycloalkyl;

wherein the aryl, heteroaryl or heterocycloalkyl, whether alone or as part of a substituent group is optionally substituted with one to three substituents independently selected from the group consisting of halogen, hydroxy, carboxy, oxo, $C_{1-4}$-alkyl, $C_{1-4}$-alkoxy, fluorinated $C_{1-4}$-alkyl, fluorinated $C_{1-4}$-alkoxy, hydroxy substituted $C_{1-4}$-alkyl, cyano, nitro, amino, $C_{1-4}$-alkylamino, di($C_{1-4}$-alkyl)amino, [1,3]dioxolanyl, $C_{1-4}$-alkoxy-C(O)— and —C(O)—$NR^E R^F$—C(O)—;

wherein $R^E$ and $R^F$ are each independently selected from the group consisting of hydrogen and $C_{1-4}$-alkyl;

provided that the chain length of $L^1$, not counting branching, plus the chain length of $L^2$, not counting branching, is not greater than about 12 atom;

provided further that when a is 0 and b is 0 then $R^1$ and $R^2$ are not each hydrogen;

or a pharmaceutically acceptable salt thereof.

3. A compound as in claim 2, selected from the group consisting of formula (I) and formula (II), wherein ═ is a single or double bond;

a is an integer from 0 to 1;

$L^1$ is selected from the group consisting of —$C_{1-4}$-alkyl-, —C(O)O—, —C(O)—, —C(O)—$C_{1-4}$-alkyl-, —C(O)—$NR^A$— and —C(O)—$C_{1-4}$-alkyl-; wherein the $C_{1-4}$-alkyl, whether alone or as part of a substitutent group, is optionally substituted with phenyl; and wherein $R^A$ is phenyl;

$R^1$ is selected from the group consisting of hydrogen, $C_{1-4}$-alkyl, aryl and biphenyl; wherein the aryl is optionally substituted with one to two substituents independently selected from the group consisting of halogen, $C_{1-4}$-alkyl and $C_{1-4}$-alkoxy;

b is an integer from 0 to 1;

$L^2$ is selected from the group consisting of —$C_{1-4}$-alkyl-, —$CH_2$—$C_{2-4}$alkynyl-, —$C_{1-4}$-alkyl-O—, —$C_{2-4}$-alkyl-NH—, —$C_{2-4}$alkyl-NH—$C_{1-4}$-alkyl- and —C(O)O—; wherein the $C_{1-4}$-alkyl or $C_{2-4}$alkyl, whether alone or as part of a substituent group is optionally substituted with hydroxy;

provided that the chain length of $L^2$, not counting branching, is one to six atoms;

$R^2$ is selected from the group consisting of hydrogen, $C_{1-4}$-alkyl, $C_{3-8}$cycloalkyl, aryl, biphenyl, heteroaryl and heterocycloalkyl;

wherein the aryl, heteroaryl or heterocycloalkyl, whether alone or as part of a substituent group, is optionally substituted with one to two substituents independently selected from the group consisting of oxo, carboxy, halogen, $C_{1-4}$-alkyl, $C_{1-4}$-alkoxy, trifluoromethyl, hydroxy substituted $C_{1-4}$-alkyl, di($C_{1-4}$alkyl)amino-carbonyl-, $C_{1-4}$-alkoxy-carbonyl- and [1,3]dioxolanyl;

provided that the chain length of $L^1$, not counting branching, plus the chain length of $L^2$, not counting branching, is not greater than about 12 atom;

provided further that when a is 0 and b is 0 then $R^1$ and $R^2$ are not each hydrogen;

or a pharmaceutically acceptable salt thereof.

4. A compound as in claim 3, selected from the group consisting of formula (I) and formula (II), wherein ═ is a single or double bond;

a is an integer from 0 to 1;

$L^1$ is selected from the group consisting of —$CH_2$—, —C(O)O—, —C(O)—, —C(O)—CH(phenyl)-, —C(O)—N(phenyl)- and —C(O)—$CH_2$—$CH_2$—;

$R^1$ is selected from the group consisting of hydrogen, t-butyl, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl), 1-biphenyl and 2-biphenyl;

b is an integer from 0 to 1;

$L^2$ is selected from the group consisting of —C(O)O—, —$CH_2$—, —$CH_2$—$CH_2$—, —$CH_2$—CC—, —$CH_2$—$CH_2$—O—, —$CH_2$—$CH_2$—$CH_2$—O—, —$CH_2$—$CH_2$—CH(OH)—, —$CH_2$—$CH_2$—NH—, —$CH_2$—CH(S—OH)—$CH_2$—O—, —$CH_2$—CH(R—OH)—$CH_2$—O— and —$CH_2$—CH(S—OH)—$CH_2$—NH—$CH_2$—;

$R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 2-naphthyl, 1-(8-methyl-naphthyl), 2-(6-methoxy-naphthyl), 4-(9H-carbazolyl), 2-biphenyl, 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl;

provided further that when a is 0 and b is 0 then $R^1$ and $R^2$ are not each hydrogen;

or a pharmaceutically acceptable salt thereof.

5. A compound as in claim 4, selected from the group consisting of a compound of formula (I) wherein ---- is a single or double bond;

a is an integer from 0 to 1;

$L^1$ is selected from the group consisting of —$CH_2$— and —C(O)O—;

$R^1$ is selected from the group consisting of hydrogen, t-butyl, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl) and 2-biphenyl;

b is an integer from 0 to 1;

$L^2$ is selected from the group consisting of —C(O)O—, —$CH_2$—, —$CH_2$—$CH_2$—, —$CH_2$—CC—, —$CH_2$—$CH_2$—O—, —$CH_2$—$CH_2$—$CH_2$—O—, —$CH_2$—$CH_2$—CH(OH)—, —$CH_2$—$CH_2$—NH—, —$CH_2$—CH(S—OH)—$CH_2$—O—, —$CH_2$—CH(R—OH)—$CH_2$—O— and —$CH_2$—CH(S—OH)—$CH_2$—NH—$CH_2$—;

$R^2$ is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 1-(8-methyl-naphthyl), 2-(6-methoxy-naphthyl), 4-(9H-carbazolyl), 2-biphenyl, 2-indanyl, 4-indolyl, 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno [4,3-c]isoxazolyl and 3S-(7,8-dimethoxy-3a,4-dihydro-3H-chromeno [4,3-c]isoxazolyl;

provided further that when a is 0 and b is 0 then $R^1$ and $R^2$ are not each hydrogen;

or a pharmaceutically acceptable salt thereof.

6. A compound as in claim 5, selected from the group consisting of a compound of formula (I) wherein ---- is a double bond;

a is an integer from 0 to 1;

$L^1$ is —$CH_2$—;

$R^1$ is selected from the group consisting of hydrogen, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl) and 2-biphenyl;

b is an integer from 0 to 1;

$L^2$ is selected from the group consisting of —$CH_2$—, —$CH_2$—$CH_2$—, —$CH_2$—CC—, —$CH_2$—$CH_2$—O—, —$CH_2$—$CH_2$—$CH_2$—O—, —$CH_2$—$CH_2$—CH(OH)—, —$CH_2$—$CH_2$—NH—, —$CH_2$—CH(S—OH)—$CH_2$—O—, —$CH_2$—CH(R—OH)—$CH_2$—O— and —$CH_2$—CH(S—OH)—$CH_2$—NH—$CH_2$—;

$R^2$ is selected from the group consisting of hydrogen, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 1-(8-methyl-naphthyl), 2-(6-methoxy-naphthyl), 4-(9H-carbazolyl), 2-indanyl, 4-indolyl, 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl;

provided further that when a is 0 and b is 0 then $R^1$ and $R^2$ are not each hydrogen;

or a pharmaceutically acceptable salt thereof.

7. A compound as in claim 5, selected from the group consisting of a compound of formula (I) wherein ---- is a single bond;

a is an integer from 0 to 1;

$L^1$ is —C(O)O—;

$R^1$ is selected from the group consisting of hydrogen, t-butyl, 2-naphthyl and 2-(1,2,3,4-tetrahydro-naphthyl);

b is an integer from 0 to 1;

$L^2$ is selected from the group consisting of —C(O)O—, —$CH_2$—CH(R—OH)—$CH_2$—O— and —$CH_2$—CH(S—OH)—$CH_2$—O—;

$R^2$ is selected from the group consisting of t-butyl, 2-naphthyl, 2-biphenyl, 2,4-dimethoxyphenyl and 4-(2-methyl-indolyl);

or a pharmaceutically acceptable salt thereof.

8. A compound as in claim 4, selected from the group consisting of a compound of formula (II) wherein ---- is a single or double bond;

a is an integer from 0 to 1;

$L^1$ is selected from the group consisting of —C(O)O—, —C(O)—, —C(O)—CH(phenyl)-, —C(O)—N(phenyl)- and —C(O)—$CH_2$—$CH_2$—;

$R^1$ is selected from the group consisting of hydrogen, t-butyl, phenyl, 1-biphenyl, 1-naphthyl and 2-naphthyl;

b is an integer from 0 to 1;
L² is selected from the group consisting of —CH₂—, —C(O)O— and —CH₂—CH(S—OH)—CH₂—O—;
R² is selected from the group consisting of hydrogen, t-butyl, 2,4-dimethoxy-phenyl, 2-naphthyl, 4-(1-methyl-indolyl) and 4-(2-methyl-indolyl);
provided further that when a is 0 and b is 0 then R¹ and R² are not each hydrogen;
or a pharmaceutically acceptable salt thereof.

9. A compound as in claim 8, selected from the group consisting of a compound of formula (II) wherein
  ⁓ is a double bond;
  a is an integer from 0 to 1;
  L¹ is —C(O)O—;
  R¹ is selected from the group consisting of hydrogen, t-butyl and 2-naphthyl;
  b is an integer from 0 to 1;
  L² is selected from the group consisting of —CH₂—, —C(O)O— and —CH₂—CH(S—OH)—CH₂—O—;
  R² is selected from the group consisting of hydrogen, t-butyl, 2-naphthyl, 4-(1-methyl-indolyl) and 4-(2-methyl-indolyl);
  provided further that when a is 0 and b is 0 then R¹ and R² are not each hydrogen;
  or a pharmaceutically acceptable salt thereof.

10. A compound as in claim 8, selected from the group consisting of a compound of formula (II) wherein
  ⁓ is a single bond;
  a is an integer from 0 to 1;
  L¹ is selected from the group consisting of —C(O)—, —C(O)—CH(phenyl)-, —C(O)—N(phenyl)- and —C(O)—CH₂—CH₂—;
  R¹ is selected from the group consisting of hydrogen, phenyl, 1-biphenyl, 1-naphthyl and 2-naphthyl;
  b is 1;
  L² is —CH₂—;
  R² is 2,4-dimethoxy-phenyl;
  or a pharmaceutically acceptable salt thereof.

11. A compound as in claim 4, selected from the group consisting of a compound of formula (I) wherein
  ⁓ is a double bond;
  a is an integer from 0 to 1;
  L¹ is selected from the group consisting of —CH₂— and —C(O)O—;
  R¹ is selected from the group consisting of hydrogen, t-butyl, phenyl, 4-methylphenyl, 3,4-dichlorophenyl, 1-naphthyl, 2-naphthyl, 2-(6-methoxy-naphthyl), 2-(1,2,3,4-tetrahydro-naphthyl), 2-(9H-fluorenyl) and 2-biphenyl;
  b is an integer from 0 to 1;
  L² is selected from the group consisting of —C(O)O—, —CH₂—, —CH₂—CH₂—, —CH₂—CC—, —CH₂—CH₂—O—, —CH₂—CH₂—CH₂—O—, —CH₂—CH₂—CH(OH)—, —CH₂—CH₂—NH—, —CH₂—CH(S—OH)—CH₂—O—, —CH₂—CH(R—OH)—CH₂—O— and —CH₂—CH(S—OH)—CH₂—NH—CH₂—;
  R² is selected from the group consisting of hydrogen, t-butyl, cyclooctyl, 2-chlorophenyl, 3-chlorophenyl, 4-fluorophenyl, 4-t-butylphenyl, 2-methoxyphenyl, 3-methoxyphenyl, 4-methoxyphenyl, 3-trifluoromethylphenyl, 3,4-dichlorophenyl, 2,4-dimethoxy-phenyl, 3-methyl-4-fluoro-phenyl, 3-trifluoromethyl-4-chloro-phenyl, 2-naphthyl, 1-(8-methyl-naphthyl), 2-(6-methoxy-naphthyl), 4-(9H-carbazolyl), 2-indanyl, 4-indolyl, 4-(1-methyl-indolyl), 4-(2-methyl-indolyl), 1-(4-hydroxymethyl-indolyl), (2-methyl-5-fluoro-indolyl), 4-(2-methyl-7-chloro-indolyl), 4-(2,7-dimethyl-indolyl), 4-(2,5-dimethyl-indolyl), 4-(2-dimethylamino-carbonyl-indolyl), 4-(2-methoxy-carbonyl-indolyl), 4-(2-methoxy-carbonyl-7-methyl-indolyl), 4-(2-methoxy-carbonyl-7-chloro-indolyl), 4-(2-methoxy-carbonyl-6-methoxy-indolyl), 4-3-benzothienyl, 3-(1H-quinazoline-2,4-dione), 2-pyridyl, 3-(6-methyl-pyridyl), 4-quinolinyl, 4-(7-chloro-quinolinyl), 5-quinolinyl, 5-(3,4-dihydro-1H-quinolin-2-one), 6-(2,3-dihydro-benzo[1,4]dioxinyl), 8-(7,8-dihydro-3H-6,9-dioxa-3-aza-cyclopenta[a]naphthyl), 3R-(7,8-dimethoxy-3a,4-dihydro-3H-chromeno[4,3-c]isoxazolyl and 3S-(7,8-dimethoxy-3a,4-dihydro-3H-chromeno[4,3-c]isoxazolyl;
  provided further that when a is 0 and b is 0 then R¹ and R² are not each hydrogen;
  or a pharmaceutically acceptable salt thereof.

12. A compound as in claim 4, selected from the group consisting of a compound of formula (I) wherein
  ⁓ is a single bond;
  a is an integer from 0 to 1;
  L¹ is selected from the group consisting of —C(O)O—, —C(O)—, —C(O)—CH(phenyl)-, —C(O)—N(phenyl)- and —C(O)—CH₂—CH₂—;
  R¹ is selected from the group consisting of hydrogen, t-butyl, phenyl, 1-biphenyl, 1-naphthyl, 2-naphthyl and 2-(1,2,3,4-tetrahydro-naphthyl);
  b is an integer from 0 to 1;
  L² is selected from the group consisting of —C(O)O—, —CH₂—, —CH₂—CH(R—OH)—CH₂—O— and —CH₂—CH(S—OH)—CH₂—O—;
  R² is selected from the group consisting of t-butyl, 2-naphthyl, 2-biphenyl, 2,4-dimethoxyphenyl and 4-(2-methyl-indolyl);
  or a pharmaceutically acceptable salt thereof.

13. A compound selected from the group consisting of formula (CI)

(CI)

and formula (CII)

(CII)

wherein
  ⁓ is a single or double bond;
  a is an integer from 0 to 1;
  L¹ is selected from the group consisting of —C₁₋₄-alkyl-, —CH₂—C₂₋₄-alkenyl-, —CH₂—C₂₋₄alkynyl-, —SO₂—, —C(O)—, —C(O)O—, —(C₁₋₄-alkyl)-C (O)—, —($C_{1-4}$-alkyl)-O—, —($C_{1-4}$-alkyl)-C(O)O—, —($C_{2-4}$alkyl)-NR$^A$, —($C_{1-4}$-alkyl)-SO$_2$—, —C(O)—($C_{1-4}$-alkyl)-, —O—($C_{1-4}$-alkyl), —C(O)O—($C_{1-4}$-alkyl)-, —NR$^A$—($C_{1-4}$-alkyl)-, —($C_{1-4}$-alkyl)-O—($C_{1-4}$ alkyl)-, —($C_{1-4}$-alkyl)-C(O)—($C_{1-4}$-alkyl)-, —($C_{1-4}$-alkyl)-OC(O)—($C_{1-4}$-alkyl)-, —($C_{1-4}$-alkyl)-C(O)O—($C_{1-4}$-alkyl)-, —($C_{2-4}$alkyl)-NR$^A$—($C_{1-4}$-alkyl)-, —($C_{1-4}$-alkyl)-SO$_2$—($C_{1-4}$-alkyl)-, —C(O)—NR$^A$—, —C(O)—NR$^A$—($C_{1-4}$-alkyl)-, —NR$^A$—C(O)— and —NR$^A$—C(O)—($C_{1-4}$-alkyl)-;

wherein the —$C_{1-4}$-alkyl- or $C_{2-4}$alkyl, whether alone or as part of a substituent group is optionally substituted with one or more substituents independently selected from the group consisting of hydroxy, $C_{1-4}$-alkoxy, amino, ($C_{1-4}$-alkyl)amino, di($C_{1-4}$-alkyl)amino, phenyl, SH and S($C_{1-4}$-alkyl);

wherein R$^A$ is selected from the group consisting of hydrogen, —$C_{1-4}$-alkyl phenyl, —C(O)—($C_{1-4}$-alkyl), —C(O)-carbocyclyl, —C(O)-heterocyclyl, —SO$_2$—($C_{1-4}$-alkyl) —SO$_2$-carbocyclyl and —SO$_2$-heterocyclyl;

provided that the chain length of L$^1$, not counting branching, is one to six atoms;

R$^1$ is selected from the group consisting of hydrogen, $C_{1-4}$-alkyl, cycloalkyl, partially unsaturated carbocyclyl, aryl and biphenyl;

wherein the cycloalkyl, partially unsaturated carbocyclyl or aryl, whether alone or as part of a substituent group is optionally substituted with one or more substituents independently selected from the group consisting of halogen, hydroxy, carboxy, oxo, $C_{1-4}$-alkyl, $C_{1-4}$alkoxy, halogenated $C_{1-4}$-alkyl, halogenated $C_{1-4}$-alkoxy, hydroxy substituted $C_{1-4}$-alkyl, cyano, nitro, amino, $C_{1-4}$-alkylamino, di($C_{1-4}$-alkyl)amino, [1,3]dioxolanyl, alkoxy-C(O)—, NR$^B$R$^C$—C(O)— and —SO$_2$—NR$^B$R$^C$;

wherein R$^B$ and R$^C$ are each independently selected from the group consisting of hydrogen and $C_{1-4}$-alkyl;

b is an integer from 0 to 1;

L$^2$ is selected from the group consisting of —$C_{1-4}$-alkyl-, —CH$_2$—$C_{2-4}$-alkenyl-, —CH$_2$—$C_{2-4}$alkynyl-, —SO$_2$—, —C(O)—, —C(O)O—, —($C_{1-4}$-alkyl)-C(O)—, —($C_{1-4}$-alkyl)-O—, —($C_{1-4}$-alkyl)-C(O)O—, —($C_{2-4}$alkyl)-NR$^D$, —($C_{1-4}$-alkyl)-SO$_2$—, —C(O)—($C_{1-4}$-alkyl)-, —O—($C_{1-4}$-alkyl), —C(O)O—($C_{1-4}$-alkyl)-, —NR$^D$—($C_{1-4}$-alkyl)-, —($C_{1-4}$-alkyl)-O—($C_{1-4}$ alkyl)-, —($C_{1-4}$-alkyl)-C(O)—($C_{1-4}$alkyl)-, —($C_{1-4}$-alkyl)-OC(O)—($C_{1-4}$-alkyl)-, —($C_{1-4}$-alkyl)-C(O)O—($C_{1-4}$-alkyl)-, —($C_{2-4}$alkyl)-NR$^D$—($C_{1-4}$-alkyl)-, —($C_{1-4}$-alkyl)-SO$_2$—($C_{1-4}$-alkyl)-, —C(O)—NR$^D$—, —C(O)—NR$^D$—($C_{1-4}$-alkyl)-, —NR$^D$—C(O)— and —NR$^D$—C(O)—($C_{1-4}$-alkyl)-;

wherein the —$C_{1-4}$-alkyl- or $C_{2-4}$alkyl, whether alone or as part of a substituent group is optionally substituted with one or more substituents independently selected from the group consisting of hydroxy, $C_{1-4}$-alkoxy, amino, ($C_{1-4}$-alkyl)amino, di($C_{1-4}$-alkyl)amino, phenyl, SH and S($C_{1-4}$-alkyl);

wherein R$^D$ is selected from the group consisting of hydrogen, —$C_{1-4}$-alkyl phenyl, —C(O)—($C_{1-4}$-alkyl), —C(O)-carbocyclyl, —C(O)-heterocyclyl, —SO$_2$—($C_{1-4}$-alkyl)-SO$_2$-carbocyclyl and —SO$_2$-heterocyclyl;

provided that the chain length of L$^2$, not counting branching, is one to six atoms;

R$^2$ is selected from the group consisting of hydrogen, $C_{1-4}$-alkyl, cycloalkyl, partially unsaturated carbocyclyl, aryl, biphenyl, heteroaryl and heterocycloalkyl;

wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, $C_{1-4}$-alkyl, $C_{1-4}$-alkoxy, halogenated $C_{1-4}$-alkyl, halogenated $C_{1-4}$-alkoxy, hydroxy substituted $C_{1-4}$-alkyl, cyano, nitro, amino, $C_{1-4}$-alkylamino, di($C_{1-4}$alkyl)amino, [1,3]dioxolanyl, —$C_{1-4}$-alkoxy-C(O)—, NR$^E$R$^F$—C(O)— and —SO$_2$—NR$^E$R$^F$;

wherein R$^E$ and R$^F$ are each independently selected from the group consisting of hydrogen and $C_{1-4}$-alkyl;

provided that the chain length of L$^1$, not counting branching, plus the chain length of L$^2$, not counting branching, is not greater than about 12 atom;

provided further that when a is 0 and b is 0 then R$^1$ and R$^2$ are not each hydrogen;

provided further than when to   is a double bond, X and Y are each =O, a is O, R$^1$ is hydrogen, b is 1 and L$^2$ is —CH$_2$—, then R$^2$ is other than 2,4-dimethoxyphenyl;

provided further than when to   is a double bond, X and Y are each =O, a is 1, L$^1$ is —CH$_2$—, b is 0 and R$^2$ is hydrogen, then R$^1$ is other than 2,4-dimethoxyphenyl;

provided further than when to   is a single bond, X and Y are each =O, a is 1, L$^1$ is —CH(CH$_3$)—, b is 1 and L$^2$ is —CH(CH$_3$)—, then R$^1$ and R$^2$ are not each phenyl;

or a pharmaceutically acceptable salt thereof.

14. A compound selected from the group consisting of formula (CIII)

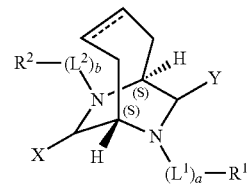

(CIII)

and formula (CIV)

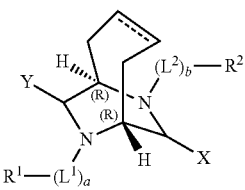

(CIV)

wherein is a single or double bond;

X and Y are each independently selected from the group consisting of hydrogen and =O;

a is an integer from 0 to 1;

L$^1$ is selected from the group consisting of —$C_{1-4}$-alkyl-, —CH$_2$—$C_{2-4}$-alkenyl-, —CH$_2$—$C_{2-4}$alkynyl-, —SO$_2$—, —C(O)—, —C(O)O—, —($C_{1-4}$-alkyl)-C(O)—, —($C_{1-4}$-alkyl)-O—, —($C_{1-4}$-alkyl)-C(O)O—, —($C_{2-4}$alkyl)-NR$^A$, —($C_{1-4}$-alkyl)-SO$_2$—, —C(O)—($C_{1-4}$-alkyl)-, —O—($C_{1-4}$-alkyl), —C(O)O—($C_{1-4}$-alkyl)-, —NR$^A$—($C_{1-4}$-alkyl)-, —($C_{1-4}$-alkyl)-O—($C_{1-4}$ alkyl)-, —($C_{1-4}$-alkyl)-C(O)—($C_{1-4}$-alkyl)-, —(C$_{1-4}$-alkyl)-OC(O)—(C$_{1-4}$-alkyl)-, —(C$_{1-4}$-alkyl)-C(O)O—(C$_{1-4}$-alkyl)-, —(C$_{2-4}$alkyl)-NR$^A$—(C$_{1-4}$-alkyl)-, —(C$_{1-4}$-alkyl)-SO$_2$—(C$_{1-4}$-alkyl)-, —C(O)—NR$^A$—, —C(O)—NR$^A$—(C$_{1-4}$-alkyl)-, —NR$^A$—C(O)— and —NR$^A$—C(O)—(C$_{1-4}$-alkyl)-;

wherein the —C$_{1-4}$-alkyl- or C$_{2-4}$alkyl, whether alone or as part of a substituent group is optionally substituted with one or more substituents independently selected from the group consisting of hydroxy, C$_{1-4}$-alkoxy, amino, (C$_{1-4}$-alkyl)amino, di(C$_{1-4}$-alkyl)amino, phenyl, SH and S(C$_{1-4}$-alkyl);

wherein R$^A$ is selected from the group consisting of hydrogen, —C$_{1-4}$-alkyl phenyl, —C(O)—(C$_{1-4}$-alkyl), —C(O)-carbocyclyl, —C(O)-heterocyclyl, —SO$_2$—(C$_{1-4}$-alkyl)-SO$_2$-carbocyclyl and —SO$_2$-heterocyclyl;

provided that the chain length of L$^1$, not counting branching, is one to six atoms;

R$^1$ is selected from the group consisting of hydrogen, C$_{1-4}$-alkyl, cycloalkyl, partially unsaturated carbocyclyl, aryl and biphenyl;

wherein the cycloalkyl, partially unsaturated carbocyclyl or aryl, whether alone or as part of a substituent group is optionally substituted with one or more substituents independently selected from the group consisting of halogen, hydroxy, carboxy, oxo, C$_{1-4}$-alkyl, C$_{1-4}$alkoxy, halogenated C$_{1-4}$-alkyl, halogenated C$_{1-4}$-alkoxy, hydroxy substituted C$_{1-4}$-alkyl, cyano, nitro, amino, C$_{1-4}$-alkylamino, di(C$_{1-4}$-alkyl)amino, [1,3]dioxolanyl, alkoxy-C(O)—, NR$^B$R$^C$—C(O)— and —SO$_2$—NR$^B$R$^C$;

wherein R$^B$ and R$^C$ are each independently selected from the group consisting of hydrogen and C$_{1-4}$-alkyl;

b is an integer from 0 to 1;

L$^2$ is selected from the group consisting of —C$_{1-4}$-alkyl-, —CH$_2$—C$_{2-4}$-alkenyl-, —CH$_2$—C$_{2-4}$alkynyl-, —SO$_2$—, —C(O)—, —C(O)O—, —(C$_{1-4}$-alkyl)-C(O)—, —(C$_{1-4}$-alkyl)-O—, —(C$_{1-4}$-alkyl)-C(O)O—, —(C$_{2-4}$alkyl)-NR$^D$, —(C$_{1-4}$-alkyl)-SO$_2$—, —C(O)—(C$_{1-4}$-alkyl)-, —O—(C$_{1-4}$-alkyl), —C(O)O—(C$_{1-4}$-alkyl)-, —NR$^D$—(C$_{1-4}$-alkyl)-, —(C$_{1-4}$-alkyl)-O—(C$_{1-4}$ alkyl)-, —(C$_{1-4}$-alkyl)-C(O)—(C$_{1-4}$-alkyl)-, —(C$_{1-4}$-alkyl)-OC(O)—(C$_{1-4}$-alkyl)-, —(C$_{1-4}$-alkyl)-C(O)O—(C$_{1-4}$-alkyl)-, —(C$_{2-4}$alkyl)-NR$^D$—(C$_{1-4}$-alkyl)-, —(C$_{1-4}$-alkyl)-SO$_2$—(C$_{1-4}$-alkyl)-, —C(O)—NR$^D$—, —C(O)—NR$^D$—(C$_{1-4}$-alkyl)-, —NR$^D$—C(O)— and —NR$^D$—C(O)—(C$_{1-4}$-alkyl)-;

wherein the —C$_{1-4}$-alkyl- or C$_{2-4}$alkyl, whether alone or as part of a substituent group is optionally substituted with one or more substituents independently selected from the group consisting of hydroxy, C$_{1-4}$-alkoxy, amino, (C$_{1-4}$-alkyl)amino, di(C$_{1-4}$-alkyl)amino, phenyl, SH and S(C$_{1-4}$-alkyl);

wherein R$^D$ is selected from the group consisting of hydrogen, —C$_{1-4}$-alkyl phenyl, —C(O)—(C$_{1-4}$-alkyl), —C(O)-carbocyclyl, —C(O)-heterocyclyl, —SO$_2$—(C$_{1-4}$-alkyl)-SO$_2$-carbocyclyl and —SO$_2$-heterocyclyl;

provided that the chain length of L$^2$, not counting branching, is one to six atoms;

R$^2$ is selected from the group consisting of hydrogen, C$_{1-4}$-alkyl, cycloalkyl, partially unsaturated carbocyclyl, aryl, biphenyl, heteroaryl and heterocycloalkyl;

wherein the partially unsaturated carbocyclyl, aryl, heteroaryl or heterocycloalkyl, whether alone or as part of a substituent group is optionally substituted with one or more substituents independently selected from the group consisting of halogen, hydroxy, carboxy, oxo, C$_{1-4}$-alkyl, C$_{1-4}$-alkoxy, halogenated C$_{1-4}$-alkyl, halogenated C$_{1-4}$-alkoxy, hydroxy substituted C$_{1-4}$-alkyl, cyano, nitro, amino, C$_{1-4}$-alkylamino, di(C$_{1-4}$alkyl)amino, [1,3]dioxolanyl, —C$_{1-4}$-alkoxy-C(O)—, NR$^E$R$^F$—C(O)— and —SO$_2$—NR$^E$R$^F$;

wherein R$^E$ and R$^F$ are each independently selected from the group consisting of hydrogen and C$_{1-4}$-alkyl;

provided that the chain length of L$^1$, not counting branching, plus the chain length of L$^2$, not counting branching, is not greater than about 12 atom;

provided further that when a is 0 and b is 0 then R$^1$ and R$^2$ are not each hydrogen;

provided further than when ⚌ is a double bond, X and Y are each ═O, a is 0, R$^1$ is hydrogen, b is 1 and L$^2$ is —CH$_2$—, then R$^2$ is other than 2,4-dimethoxyphenyl;

provided further than when ⚌ is a double bond, X and Y are each ═O, a is 1, L$^1$ is —CH$_2$—, b is 0 and R$^2$ is hydrogen, then R$^1$ is other than 2,4-dimethoxyphenyl;

provided further than when ⚌ is a single bond, X and Y are each ═O, a is 1, L$^1$ is —CH(CH$_3$)—, b is 1 and L$^2$ is —CH(CH$_3$)—, then R$^1$ and R$^2$ are not each phenyl;

or a pharmaceutically acceptable salt thereof.

15. A compound selected from the group consisting of the compound of formula (CV)

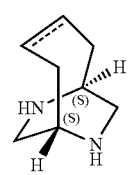

(CV)

and the compound of formula (CVI)

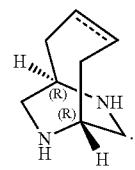

(CVI)

16. A pharmaceutical composition comprising a pharmaceutically acceptable carrier and a compound of claim 1.

17. A pharmaceutical composition made by mixing a compound of claim 1 and a pharmaceutically acceptable carrier.

18. A process for making a pharmaceutical composition comprising mixing a compound of claim 1 and a pharmaceutically acceptable carrier.

* * * * *